(12) United States Patent
Yang

(10) Patent No.: US 10,750,744 B2
(45) Date of Patent: Aug. 25, 2020

(54) PROCESS FOR THE PREPARATION OF ISOXAZOLINE COMPOUNDS

(71) Applicant: BOEHRINGER INGELHEIM ANIMAL HEALTH USA INC., Duluth, GA (US)

(72) Inventor: Chunhua Yang, Belle Mead, NJ (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 16/182,838

(22) Filed: Nov. 7, 2018

(65) Prior Publication Data

US 2019/0133129 A1    May 9, 2019

Related U.S. Application Data

(62) Division of application No. 15/480,316, filed on Apr. 5, 2017, now Pat. No. 10,433,552.

(60) Provisional application No. 62/319,207, filed on Apr. 6, 2016.

(51) Int. Cl.
| | | |
|---|---|---|
| *C07D 453/04* | (2006.01) | |
| *C07D 261/04* | (2006.01) | |
| *A01N 43/80* | (2006.01) | |
| *A01N 43/42* | (2006.01) | |
| *A61K 31/42* | (2006.01) | |

(52) U.S. Cl.
CPC ............. *A01N 43/80* (2013.01); *A01N 43/42* (2013.01); *A61K 31/42* (2013.01); *C07D 261/04* (2013.01); *C07D 453/04* (2013.01)

(58) Field of Classification Search
CPC ............................ C07D 261/04; C07D 453/04
See application file for complete search history.

(56) References Cited

U.S. PATENT DOCUMENTS

| | | | | |
|---|---|---|---|---|
| 2014/0127165 A1* | 5/2014 | Lahm | ............... | C07D 261/04 424/93.4 |
| 2014/0350261 A1 | 11/2014 | Toyama | | |

FOREIGN PATENT DOCUMENTS

| | | |
|---|---|---|
| WO | 2009/002809 A2 | 12/2008 |
| WO | 2009063910 A1 | 5/2009 |
| WO | 2011067272 A1 | 6/2011 |
| WO | 2011104089 A1 | 9/2011 |
| WO | 2011154434 A1 | 12/2011 |
| WO | 2012120399 A1 | 9/2012 |
| WO | 2013116236 A1 | 8/2013 |
| WO | 2014081800 A1 | 5/2014 |
| WO | 2014090918 A1 | 6/2014 |

OTHER PUBLICATIONS

"Enantioselective Synthesis of Trifluoromethyl-Substituted 2-Isoxazolines: Asymmetric Hydroxylamine/Enone Cascade Reaction", Matoba et al., Angewandte Chemie International Edition, 2010, vol. 49, No. 33, pp. 5762-5766.
"Organocatalytic Asymmetric Synthesis of [beta]-Aryl- [beta]-isocyano Esters", Morana et al., Advanced Synthesis and Catalysis, 2012, vol. 354, No. 11-12, pp. 2199-2210.
"Unexpected metal base-dependent inversion of the enantioselectivity in the asymmetric synthesis of alpha-amino acids using phase-transfer catalysts derived from cinchonidine", Mazon et al., Tetrahedron Asymmetry, 2002, vol. 13, No. 20, pp. 2181-2185.
"Preparation of Chiral Isoxazolines by Chiral Phase-Transfer-Catalyzed Addition of Hydroxylamine to Chalcones", anonymous author, IP.com, IP.com No. IPCOM000187185D, Sep. 1, 2009.
"Enantioselective Synthesis of 5-Trifluoromethyl-2-isoxazolines and Their N-Oxides by [Hydroxy(tosyloxy)iodo] benzene-Mediated Oxidative N—O Coupling", Kawai et al., European Journal of Organic Chemistry, 2013, pp. 6506-6509.
"High-Throughput Screening by Using a Blue-Fluorescent Antibody Sensor", M. Matsushita et al., Angewandte Chemi International Edition, 2003, vol. 42, No. 48, pp. 5984-5987.
"Organocatalytic regioselective Michael additions of cyclic enones via asymmetric phase transfer catalysis", R. Ceccarelli et al., Organic & Biomolecular Chemistry, 2006, vol. 4, No. 23, pp. 4281-4284.
Dendrimer Disassembly in the Gas Phase: a Cascade Fragmentation Reaction of Frechet Dendrons, B. Baytekin et al., Chemistry—a European Journal, 2009, vol. 15, No. 29, pp. 7139-7149.
"Chiral Quaternary Ammonium Aryloxide/N,O-Bis(trimethylsilyl)acetamide Combination as Efficient Organocatalytic System for the Direct Vinylogous Aldol Reaction of (5H)-Furan-2-one Derivatives", Advanced Cynthesis & Catalysis, 2013, vol. 355, No. 5, pp. 841-846.

\* cited by examiner

*Primary Examiner* — Shawquia Jackson
(74) *Attorney, Agent, or Firm* — Judy Jarecki-Black; John Ezcurra

(57) ABSTRACT

This invention relates to processes for the preparation of antiparasitic isoxazoline compounds enriched in an enantiomer using quinine-based chiral phase transfer catalyst. The invention also relates to novel quinine-based phase transfer catalysts and to a toluene solvent form of the isoxazoline compound of the invention.

31 Claims, 7 Drawing Sheets

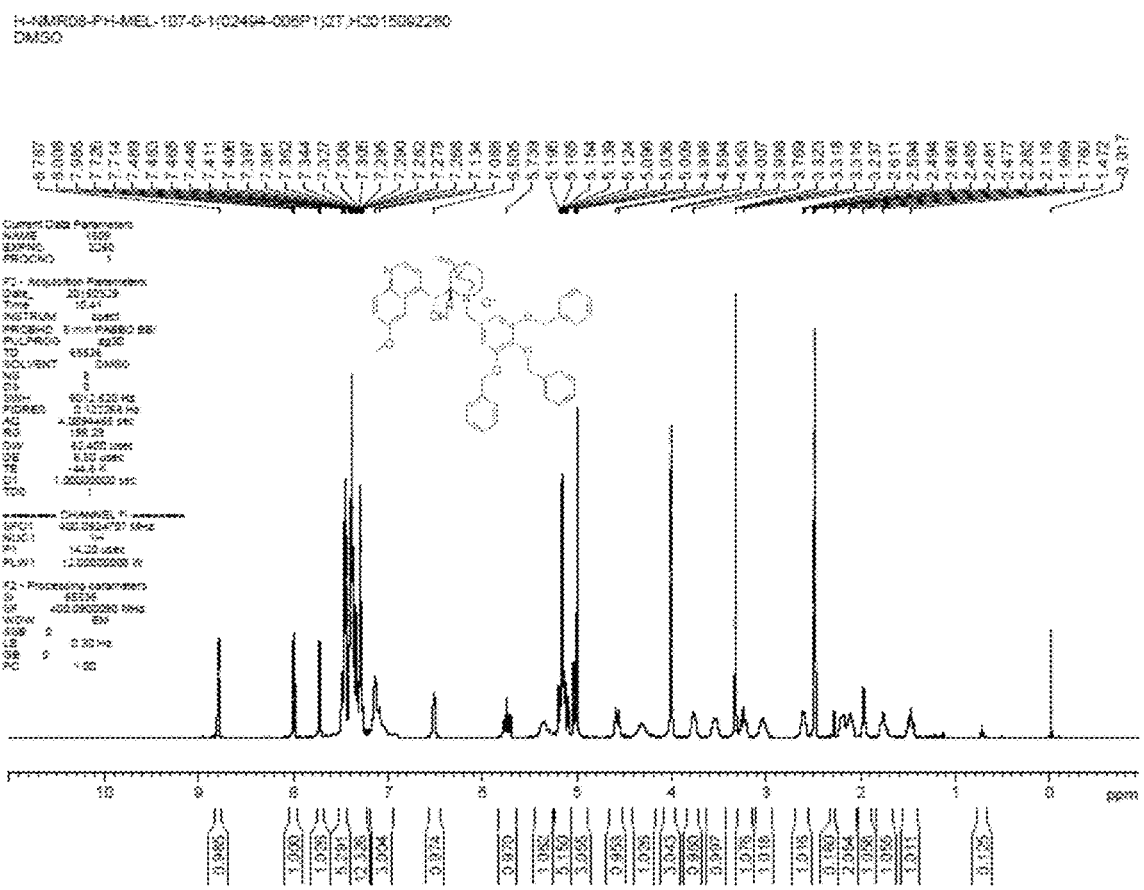
Figure 1: $^1$H NMR spectra of chiral phase transfer catalyst (IIIa-13-1) prepared in Example 1 in DMSO-d$_6$.

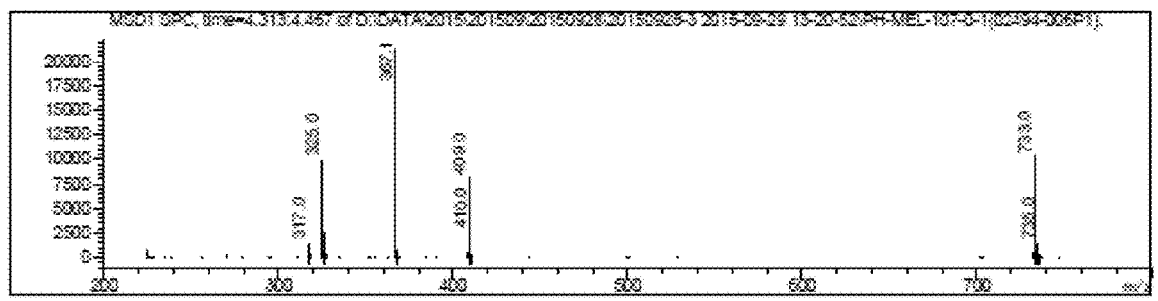
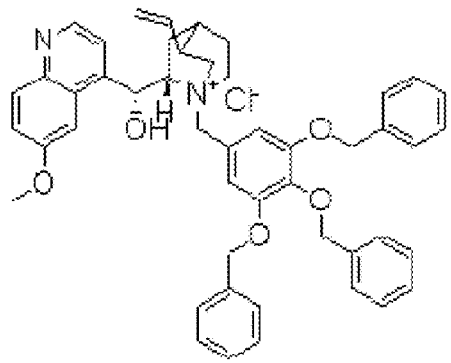
Figure 2: LCMS spectra of chiral phase transfer catalyst (IIIa-13-1) prepared in Example 1.

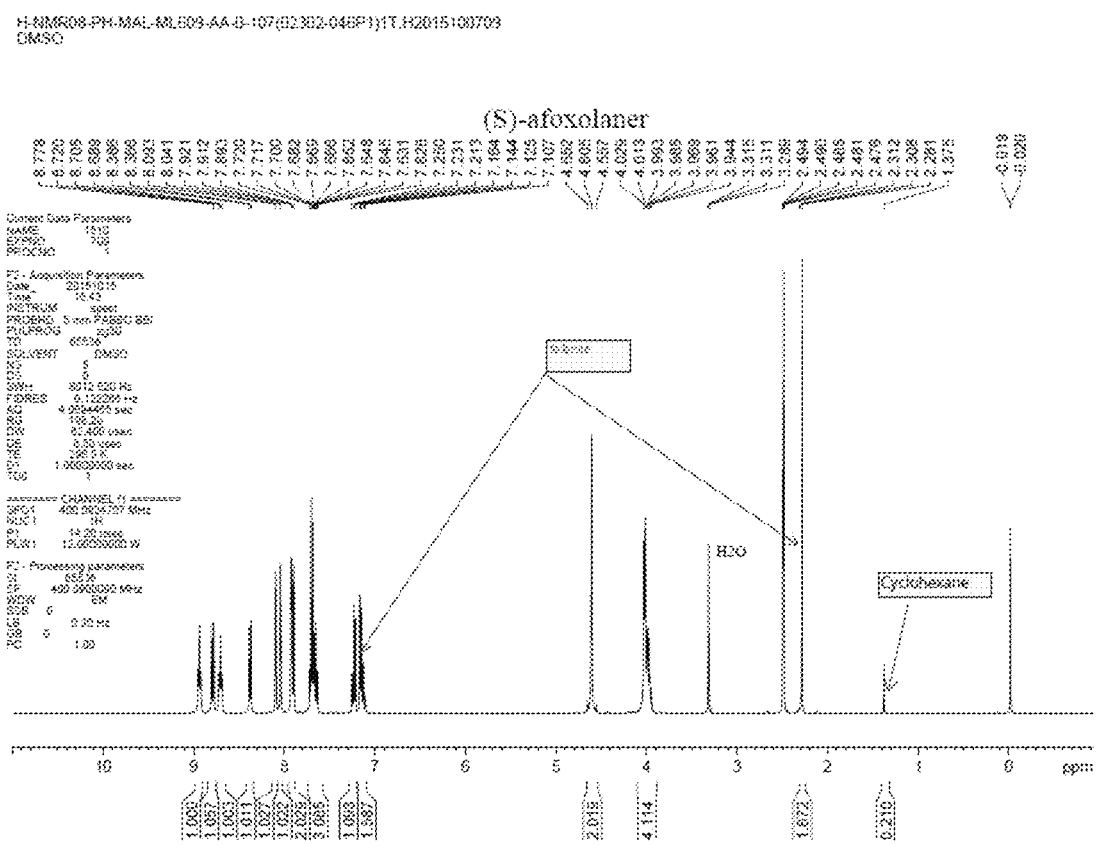
Figure 3: ¹H NMR of (S)-afoxolaner in DMSO-d₆ prepared in Example 7

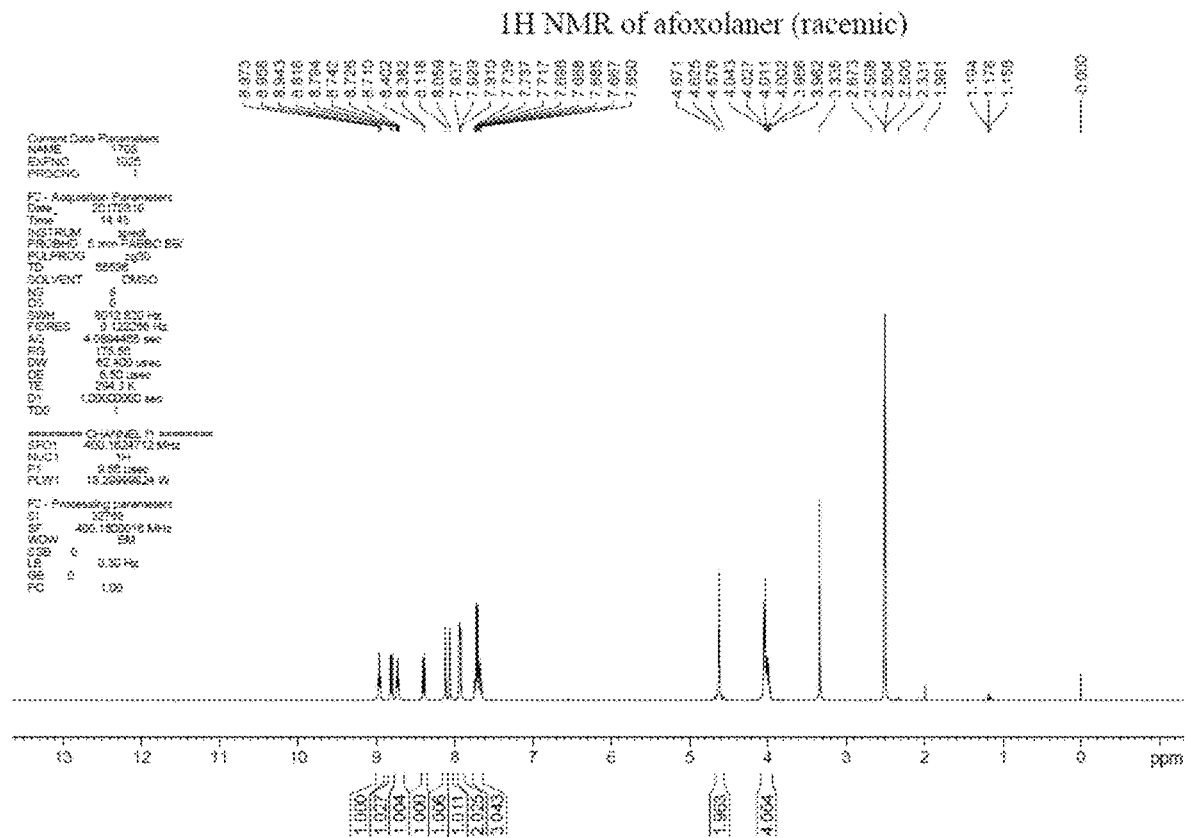
Figure 4: $^1$H NMR of afoxolaner (racemic) in DMSO-$d_6$.

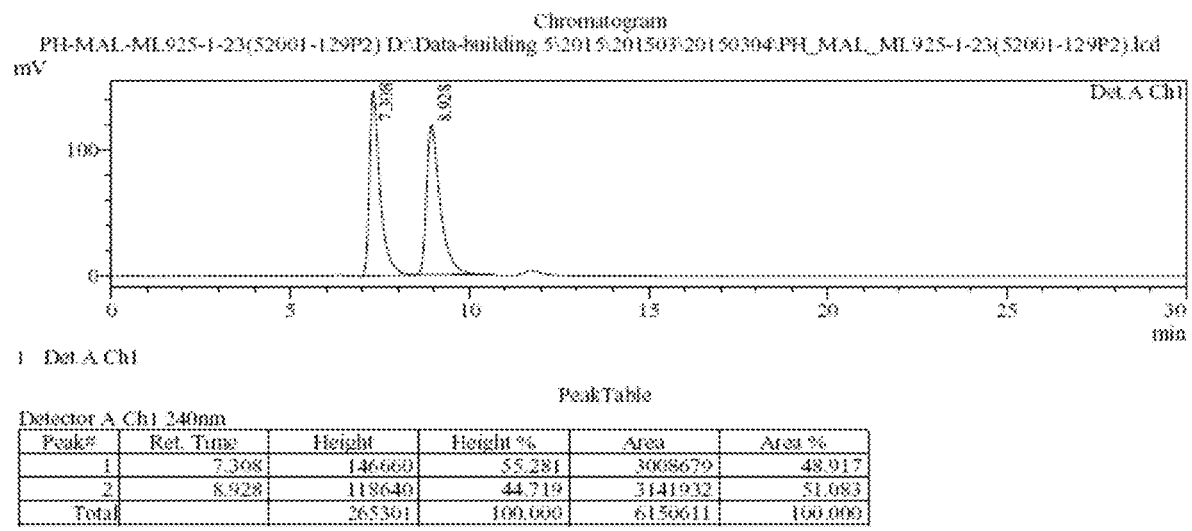
Figure 5: chiral HPLC of afoxolaner (racemic) using HPLC method of Example 3.
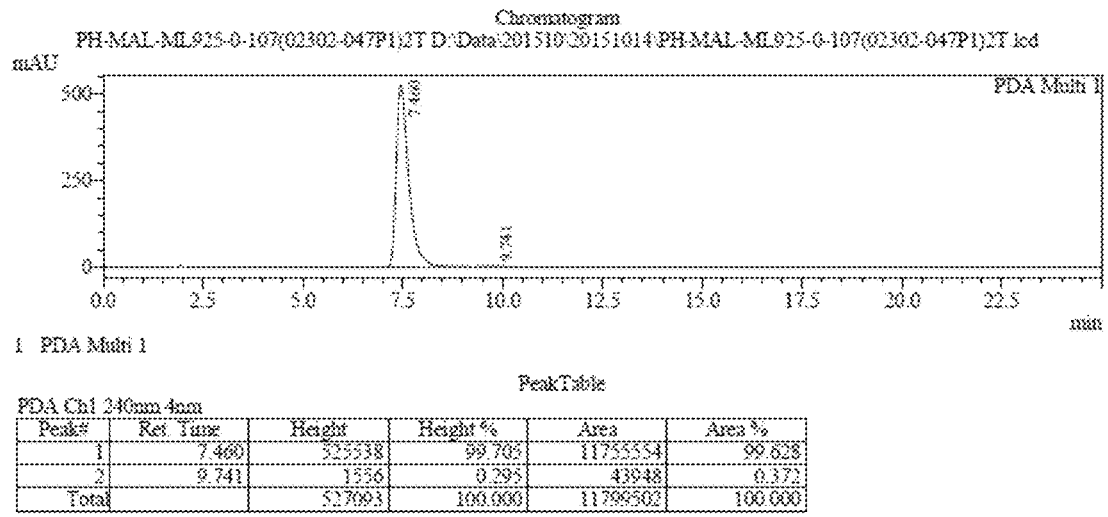
Figure 6: chiral HPLC of (S)-afoxolaner using HPLC method of Example 3.

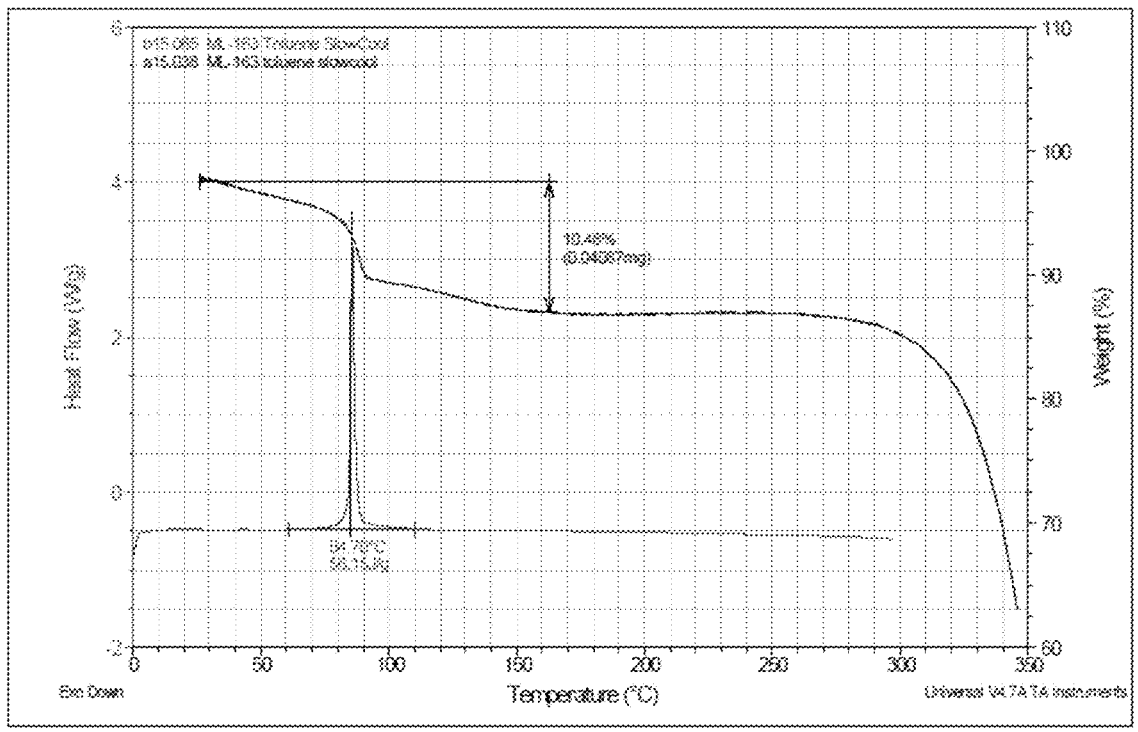
Figure 7: TGA and DSC of toluene solvate of (S)-afoxolaner from Example 12
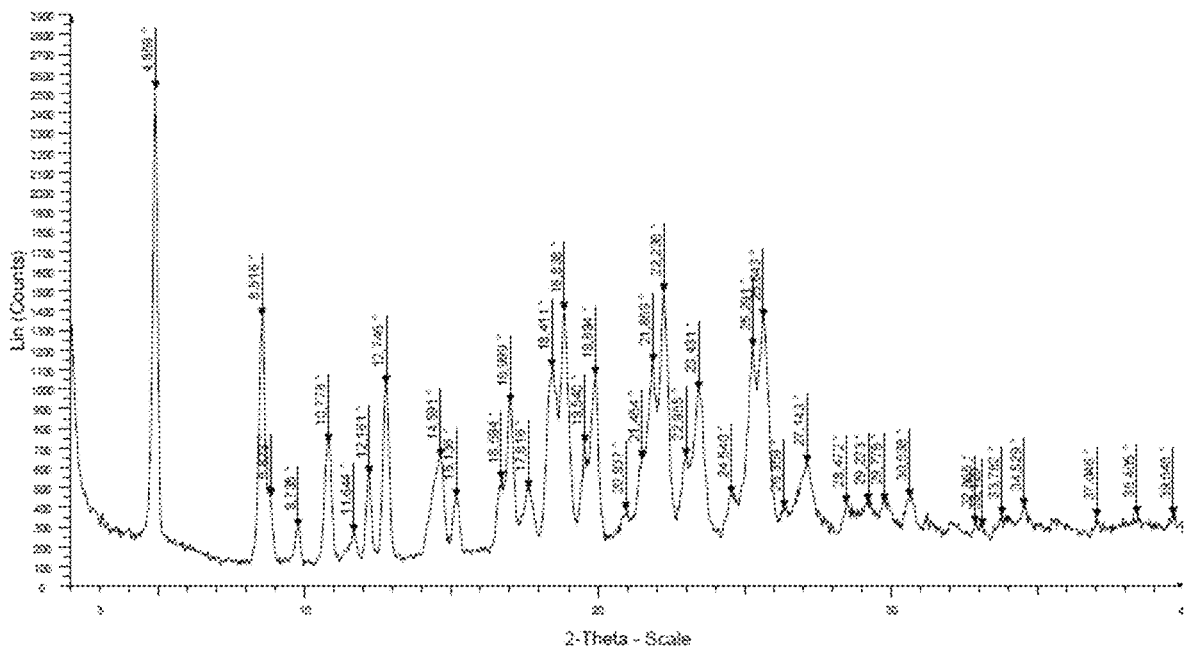
Figure 8: X-Ray Powder Diffraction of toluene solvate of (S)-afoxolaner from Example 12

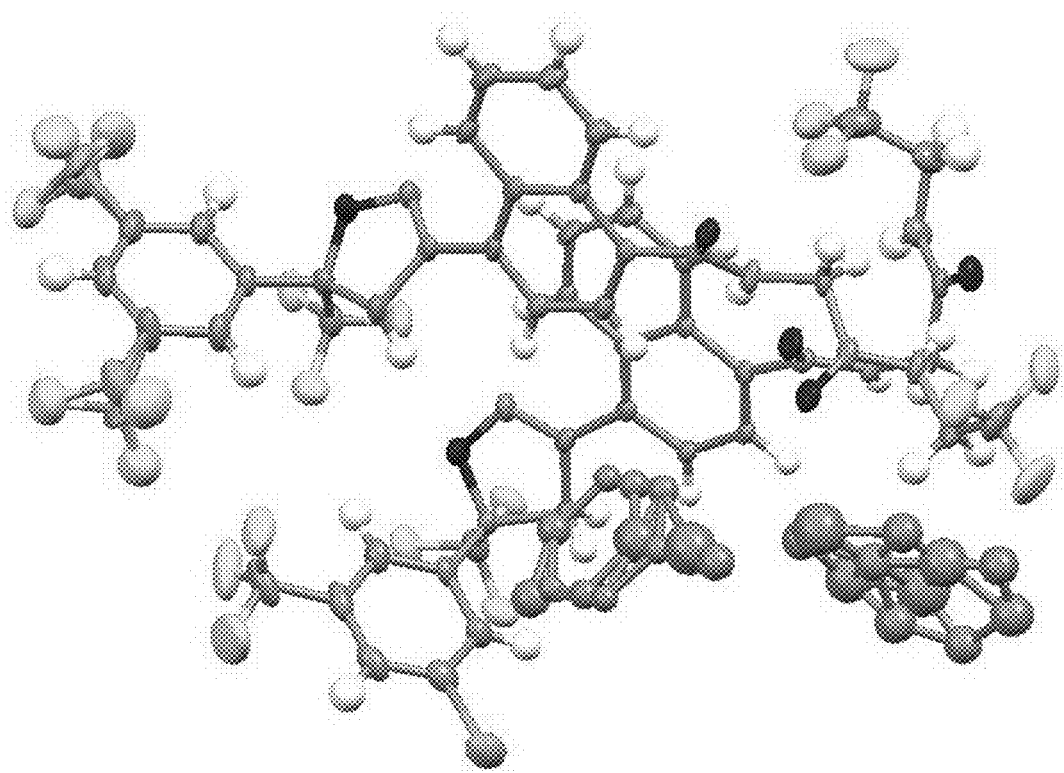
Figure 9: (*S*)-afoxolaner single crystal structure
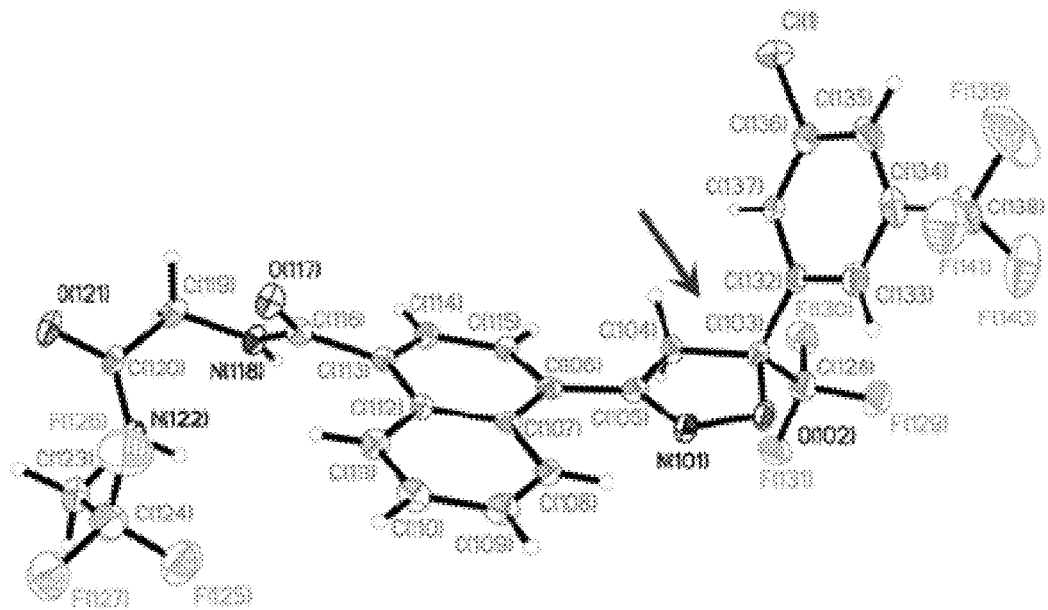
Figure 10: Molecular Structure of (*S*)-afoxolaner from Cerius 2 software

PROCESS FOR THE PREPARATION OF ISOXAZOLINE COMPOUNDS

CROSS REFERENCE TO RELATED APPLICATIONS

This application is a divisional application of U.S. patent application Ser. No. 15/480,316 filed on Apr. 5, 2017, which claims the benefit of priority to U.S. Provisional Application No. 62/319,207, filed Apr. 6, 2016, both of which are incorporated herein by reference in their entirety.

FIELD OF THE INVENTION

The present invention provides stereoselective processes for the preparation of isoxazoline compounds enriched in an enantiomer. Also provided is a novel crystalline toluene solvate of (S)-afoxolaner prepared by the processes of the invention. The invention also provides novel quinine-based chiral phase transfer catalysts and processes to prepare the novel catalysts.

BACKGROUND OF THE INVENTION

Animals such as mammals and birds are often susceptible to parasite infestations/infections. These parasites may be ectoparasites, such as insects, and endoparasites such as filariae and other worms. Domesticated animals, such as cats and dogs, are often infested with one or more of the following ectoparasites:

- fleas (e.g. *Ctenocephalides* spp., such as *Ctenocephalides felis* and the like);
- ticks (e.g. *Rhipicephalus* spp., *Ixodes* spp., *Dermacentor* spp., *Amblyomma* spp., and the like);
- mites (e.g. *Demodex* spp., *Sarcoptes* spp., *Otodectes* spp., and the like);
- lice (e.g. *Trichodectes* spp., *Cheyletiella* spp., *Linognathus* spp. and the like);
- mosquitoes (*Aedes* spp., *Culex* spp., *Anopheles* spp. and the like); and
- flies (*Haematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas are also vectors of pathogenic agents in animals and humans, such as dog tapeworm (*Dipylidium caninum*).

Similarly, ticks are also harmful to the physical and psychological health of the animal or human. However, the most serious problem associated with ticks is that they are the vector of pathogenic agents in both humans and animals. Major diseases which are caused by ticks include borreliosis (Lyme disease caused by *Borrelia burgdorferi*), babesiosis (or piroplasmosis caused by *Babesia* spp.) and rickettsioses (also known as Rocky Mountain spotted fever). Ticks also release toxins which cause inflammation or paralysis in the host. Occasionally, these toxins are fatal to the host.

Likewise, farm animals are also susceptible to parasite infestations. For example, cattle are affected by a large number of parasites. A parasite which is very prevalent among farm animals is the tick genus *Rhipicephalus* (*Boophilus*), especially those of the species *microplus* (cattle tick), *decoloratus* and *annulatus*. Ticks, such as *Rhipicephalus* (*Boophilus*) *microplus*, are particularly difficult to control because they live in the pasture where farm animals graze.

Animals and humans also suffer from endoparasitic infections including, for example, helminthiasis which is most frequently caused by a group of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides, Toxocara* and *Trichinella*.

Recently, isoxazole and isoxazoline-containing compounds have been demonstrated to be effective against parasites that harm animals. For example, U.S. Pat. Nos. 7,964,204 and 8,410,153 (to DuPont, both incorporated herein by reference) disclose isoxazoline compounds according to Formula (I) below, which are active against ectoparasites and.

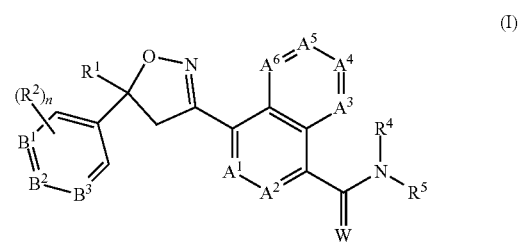

A particularly active isoxazoline compound, 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide, is known by the nonproprietary name afoxolaner. Afoxolaner has the following chemical structure:

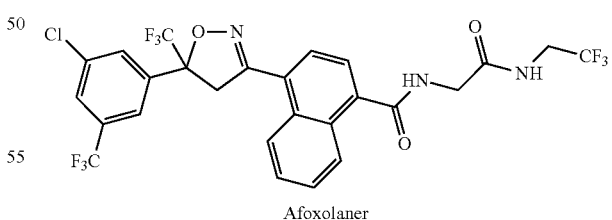

Afoxolaner

Other isoxazoline compounds that have been found to be highly active against parasitic insects and arachnids are known by the nonproprietary names fluralaner (see U.S. Pat. No. 7,662,972, which is incorporated herein by reference), sarolaner (see U.S. Pat. No. 8,466,15, incorporated herein by reference) and lotilaner (see, for example U.S. Pat. No. 8,383,659, incorporated herein by reference). The structures of these compounds are shown below:

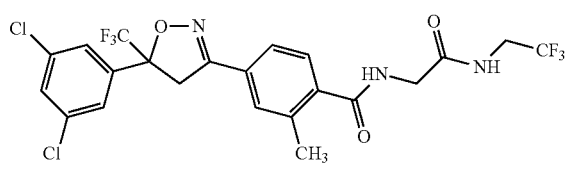

Fluralaner

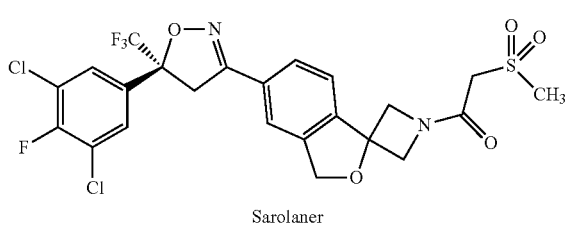

Sarolaner

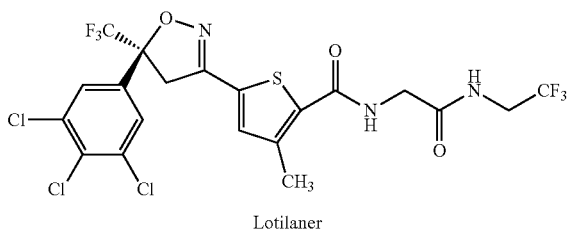

Lotilaner

In addition, published patent application nos. US 2010/0254960 A1, WO 2007/070606 A2, WO 2007/123855 A2, WO 2010/003923 A1, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1 and WO 2007/075459 A2 and U.S. Pat. No. 7,951,828 (all incorporated herein by reference) describe various other parasiticidal isoxazoline compounds.

It is known in the field that isoxazoline compounds having a chiral quaternary carbon atom such as the carbon atom adjacent to the oxygen on the isoxazoline ring of the compounds described above have at least two optical isomer (enantiomers) that are mirror images of each other. Furthermore, it is sometimes the case with biologically active compounds that one of the enantiomers is more active than the other enantiomer. In addition, it is sometimes the case that one enantiomer of a biologically active compound is less toxic than the other enantiomer. Therefore, with optically active compounds it is desirable to utilize the enantiomer that is most active and less toxic (eutomer). However, isolating the most active enantiomer from a mixture can be costly and result in waste of up to half of the racemic mixture prepared.

Processes to prepare certain isoxazoline compounds enriched in an enantiomer using some cinchona alkaloid-derived phase transfer catalysts have been described. For example, US 2014/0206633 A1, US 2014/0350261 A1, WO 2013/116236 A1 and WO 2014/081800 A1 (incorporated herein by reference) describe the synthesis of certain isoxazoline active agents enriched in an enantiomer using cinchona alkaloid-based chiral phase transfer catalysts. Further, Matoba et al., Angew. Chem. 2010, 122, 5898-5902 describes the chiral synthesis of certain pesticidal isoxazoline active agents. However, these documents do not describe the processes and certain catalysts described herein.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention relates to processes for the preparation of enantiomerically enriched antiparasitic isoxazoline compounds and to novel phase transfer catalysts useful for these processes. In one embodiment, the invention provides a process for the preparation of an isoxazoline compound of formula (I) below, which is enriched in one enantiomer:

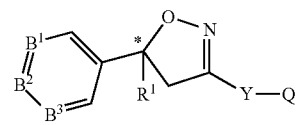

wherein $B^1$, $B^2$, $B^3$, $R^1$, Y and Q are defined herein and wherein the asterisk represents that the carbon atom is a chiral quaternary carbon atom;

comprising reacting a compound of formula (II):

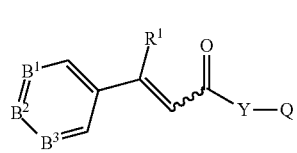

wherein $B^1$, $B^2$, $B^3$, $R^1$, Y and Q are as defined for formula (I), with hydroxylamine in the presence of water, a base and a chiral phase transfer catalyst of formula (IIIa) or (IIIb):

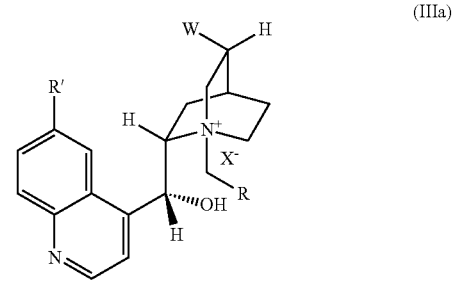

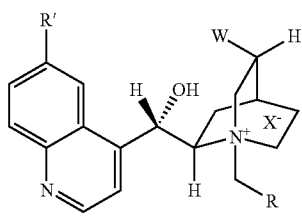

(IIIb)

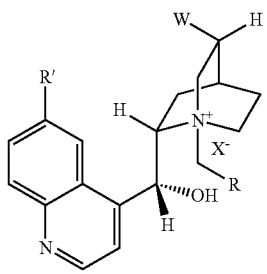

(IIIa)

wherein R is aryl or heteroaryl substituted with one or more aralkoxy, amino, alkylamino or dialkylamino groups, R' is hydrogen or $C_1$-$C_3$alkoxy, W is ethyl or vinyl and $X^-$ is a counter ion including halogen, mesylate, tosylate, triflate, brosylate, nonylate, tresylate, and the like.

The (S)-enantiomer of antiparasitic compounds of formula (I) have been shown to be more active against ectoparasites (e.g. fleas and ticks) than the (R)-enantiomer. The (S)-enantiomer of the compounds is produced as the major product when a phase transfer catalyst of formula (IIIa) is used and the (R)-enantiomer is produced as the major product when (IIIb) is used.

In another embodiment of the invention, the invention provides a process for the preparation of an isoxazoline compound of Formula IA, wherein $X^1$, $X^2$ and $X^3$ are each independently H, halogen, $C_1$-$C_3$alkyl or $C_1$-$C_3$haloalkyl, which is enriched in the (S)-enantiomer:

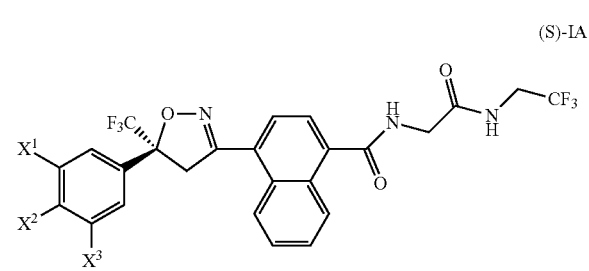

(S)-IA comprising reacting a compound of formula (IIA):

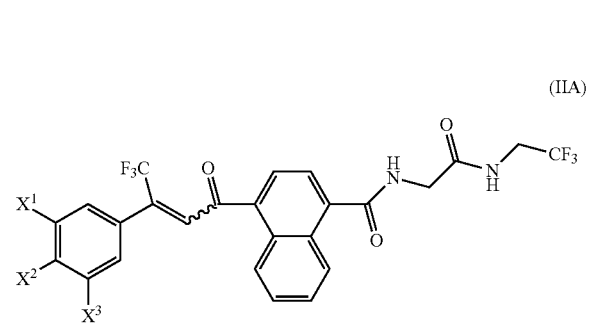

(IIA)

wherein $X^1$, $X^2$ and $X^3$ have the meanings described above for Formula IA, with hydroxylamine in the presence of water, an organic solvent that is not miscible with water, a base and a chiral phase transfer catalyst of formula (IIIa):

wherein R is aryl or heteroaryl optionally substituted with one or more $C_1$-$C_3$alkoxy, amino, alkylamino, dialkylamino or aralkoxy groups, R' is hydrogen or $C_1$-$C_3$alkoxy, W is ethyl or vinyl and $X^-$ is an anion.

In other embodiments, the invention provides processes for the preparation of the following compounds enriched in the (S)-enantiomer using a chiral phase transfer catalyst of formula (IIIa):

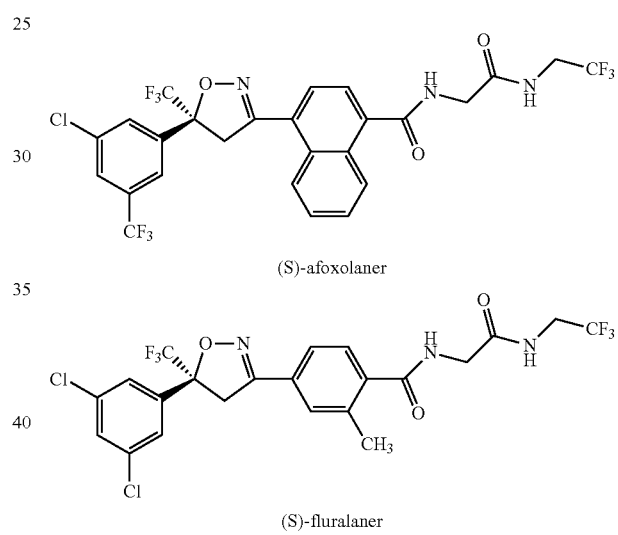

(S)-afoxolaner (S)-fluralaner sarolaner

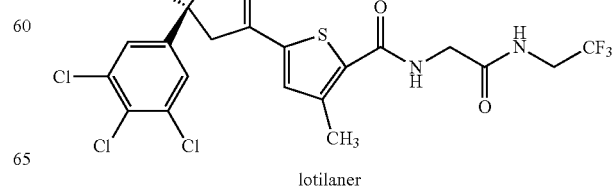

lotilaner

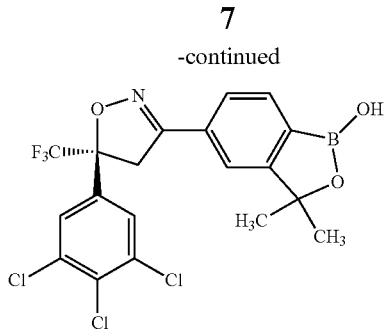

(S)-ID-1

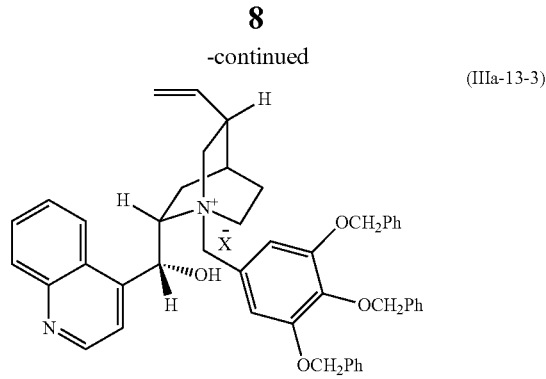

(IIIa-13-3)

(IIIa-13-4)

In another embodiment of the invention, the isoxazoline compounds of formula (I) enriched in the (S)-enantiomer, which are prepared using the chiral phase transfer catalyst of formula (IIIa), are purified and further enriched in the (S)-enantiomer by crystallization using an aromatic solvent including, but not limited to, toluene, ethylbenzene, xylenes, chlorobenzene, o-dichlorobenzene, fluorobenzene, anisole and mesitylene.

In another embodiment, the invention provides a crystalline toluene solvate form of (S)-afoxolaner prepared by crystallization of the compound from toluene or a solvent mixture containing toluene. Other solvates of the (S)-enantiomers of the isoxazoline compounds of formula (I) of the invention with aromatic solvents such as ethylbenzene, xylenes, chlorobenzene, o-dichlorobenzene, fluorobenzene, anisole and mesitylene are also envisioned.

In other embodiments, the invention provides parasiticidal veterinary compositions comprising the compounds of formula (I) enriched in the (S)-enantiomer and methods and uses of the compounds and compositions for treating and preventing parasitic infestations or infections in animals. Also included are agricultural compositions, methods and uses comprising the compounds of formula (I) enriched in the (S)-enantiomer for combating animal pests and protecting crops and plants from these pests.

In another embodiment, the invention provides a novel and inventive phase transfer catalyst of formula (IIIa-13-1), formula (IIIa-13-2), formula (IIIa-13-3) or formula (IIIa-13-4), or a mixture of any of these catalysts:

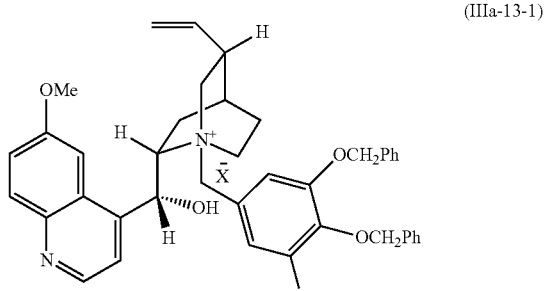

(IIIa-13-1)

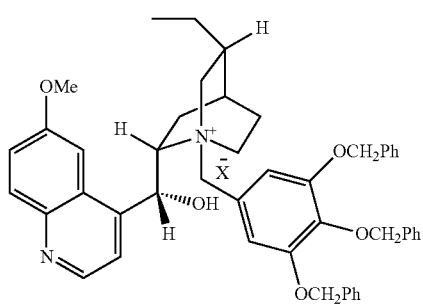

(IIIa-13-2)

wherein X⁻ is a counter ion. In one embodiment of formula (IIIa-13-1), (IIIa-13-2), (IIIa-13-3) or (IIIa-13-4), X⁻ is a halogen counter ion such as chloride.

In yet another embodiment, the invention provides novel and inventive processes for the preparation of the chiral phase transfer catalysts described herein.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 is the $^1$H NMR spectra of chiral phase transfer catalyst (IIIa-13-1) prepared in Example 1.

FIG. 2 is the LCMS (HPLC-Mass Spectra) spectra of chiral phase transfer catalyst (IIIa-13-1) prepared in Example 1.

FIG. 3 is the $^1$H NMR spectra of (S)-afoxolaner-toluene solvate prepared in Example 7 in DMSO-$d_6$.

FIG. 4 is the $^1$H NMR spectra of afoxolaner (racemic) in DMSO-$d_6$.

FIG. 5 is the chiral HPLC chromatogram of afoxolaner using the HPLC method described in Example 3.

FIG. 6 is the chiral HPLC chromatogram of (S)-afoxolaner prepared in Example 7 using the HPLC method described in Example 3.

FIG. 7 shows the combined TGA and DSC profiles of crystalline (S)-afoxolaner toluene solvate as described in Example 12.

FIG. 8 shows the X-Ray Powder Diffraction pattern of the crystalline toluene solvate of (S)-afoxolaner as described in Example 12.

FIG. 9 shows an X-ray single-crystal structure of crystalline (S)-afoxolaner toluene solvate.

FIG. 10 shows the molecular structure of (S)-afoxolaner determined using Cerius 2 software.

DETAILED DESCRIPTION

In a first aspect, the present invention provides a process for the preparation of an isoxazoline compound of formula (I) below, which is enriched in one enantiomer:

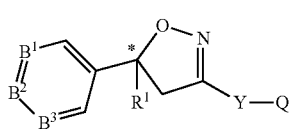

(I)

wherein:

$B^1$, $B^2$, $B^3$, are each independently C—R or N;

each R is independently H, halogen, cyano, —$NO_2$, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino or alkoxycarbonyl;

$R^1$ is $C_1$-$C_3$alkyl or $C_1$-$C_3$haloalkyl;

Y is an optionally substituted phenylene, naphthylene, indanylene, a 5- or 6-membered heteroarylene or an 8-10-membered fused heterobicyclylene, wherein the optional substituents are selected from the group consisting of halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN or —$NO_2$ and $NH_2$—C(=S)—;

Q is T-$NR^2R^3$, the group (—$CH_2$—)(—$CH_2$—)N—$R^3$, OH, $NH_2$, alkoxy, haloalkoxy, alkylamino, haloalkylamino, dialkylamino, halodialkylamino, thiol, alkylthio, haloalkylthio, alkylsulfinyl, haloalkylsulfinyl, alkylsulfonyl, haloalkylsulfonyl, or an optionally substituted 5- or 6-membered carbocyclyl, heterocyclyl or heteroaryl ring;

T is $(CH_2)_n$, $CH(CH_3)$, $CH(CN)$, C(=O) or C(=S);

$R^2$ is H, alkyl, alkenyl, alkynyl, cycloalkyl, alkylcycloalkyl, cycloalkylalkyl, alkylcarbonyl or alkoxycarbonyl;

$R^3$ is H, $OR^7$, $NR^8R^9$ or $Q^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from $R^4$; or $R^2$ and $R^3$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;

each $R^4$ is independently halogen; alkyl, cycloalkyl, alkoxy, alkylthio, haloalkylthio, alkylsulfinyl, haloalkylsulfinyl, alkylsulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —$NH_2$, —CN or —$NO_2$; or $Q^2$;

each $R^5$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —CN or —$NO_2$;

each $R^6$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN, —$NO_2$, phenyl or pyridinyl;

$R^7$ is H; or alkyl, alkenyl, alkynyl, cycloalkyl, alkylcycloalkyl or cycloalkylalkyl, each optionally substituted with one of more halogen;

$R^8$ is H, alkyl, alkenyl, alkynyl, cycloalkyl, alkylcycloalkyl, cycloalkylalkyl, alkylcarbonyl or alkoxycarbonyl;

$R^9$ is H; $Q^3$; or alkyl, alkenyl, alkynyl, cycloalkyl, alkylcycloalkyl or cycloalkylalkyl, each optionally substituted with one or more substituents independently selected from $R^4$; or $R^8$ and $R^9$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^5$;

$Q^2$ is independently a phenyl ring or a 5- or 6-membered heterocyclic ring, each ring optionally substituted with one or more substituents independently selected from $R^6$;

$Q^3$ is a phenyl ring or a 5- or 6-membered heterocyclic ring, each ring optionally substituted with one or more substituents independently selected from $R^6$; and n is 1, 2 or 3;

wherein the asterisk represents that the carbon atom is a quaternary carbon atom;

comprising reacting a compound of formula (II):

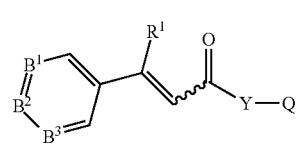

(II)

wherein $B^1$, $B^2$, $B^3$, $R^1$, Y and Q are as defined for formula (I), with hydroxylamine in the presence of water, a base and a chiral phase transfer catalyst of formula (IIIa) or (IIIb):

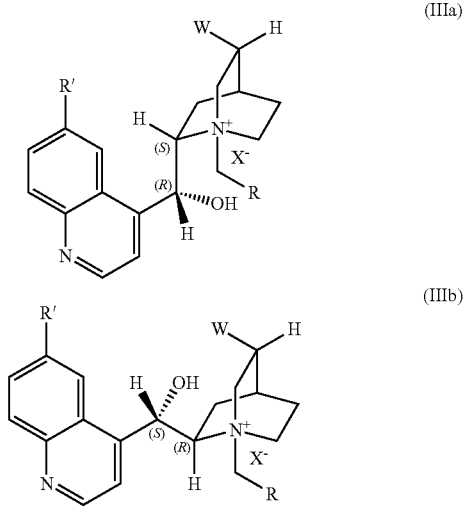

wherein R is aryl or heteroaryl substituted with one or more aralkoxy, amino, alkylamino or dialkylamino groups, R' is hydrogen or $C_1$-$C_3$alkoxy, W is ethyl or vinyl and $X^-$ is an anion. In the structures of (IIIa) and (IIIb) shown above, the stereochemistry is shown for clarity. In one embodiment, $X^-$ is a halogen counter ion. In another embodiment, $X^-$ is chloride or bromide. In another embodiment, $X^-$ is a tosylate, mesylate, triflate, brosylate, nosylate or tresylate counter ion, and the like.

In an embodiment, the invention provides a process for the preparation of an isoxazoline compound of formula (I) shown above, which is enriched in one enantiomer, which comprises reacting the compound of formula (II) as defined above with hydroxylamine in the presence of water, a base and a chiral phase transfer catalyst of formula (IIIa) or (IIIb); and isolating the product by crystallization.

In another embodiment, the invention provides a process for the preparation of an isoxazoline compound of formula (I) shown above, which is enriched in one enantiomer, which comprises reacting the compound of formula (II) as defined above with hydroxylamine in the presence of water, a base and a chiral phase transfer catalyst of formula (IIIa) or (IIIb); and isolating the product by crystallization from an aromatic solvent or a solvent mixture comprising an aromatic solvent.

In yet another embodiment, the invention provides a process for the preparation of an isoxazoline compound of formula (I) shown above, which is enriched in one enantiomer, which comprises reacting the compound of formula (II) as defined above with hydroxylamine in the presence of water, a base and a chiral phase transfer catalyst of formula (IIIa) or (IIIb); and isolating the product by crystallization from toluene, ethylbenzene, xylenes, chlorobenzene, o-dichlorobenzene, fluorobenzene, anisole or mesitylene, or a combination thereof, or a solvent mixture comprising one or more of these solvents.

The chiral phase transfer of formula (IIIa) or (IIIb) used in the process is a very important factor for achieving the best possible enrichment of the desired enantiomer. It has been surprisingly found that when R in formula (IIIa) or (IIIb) is a substituted aryl group, including a phenyl group, the type of substituent and the extent of substitution has a pronounced effect on the stereoselectivity of the reaction. Although quinine phase transfer catalysts are known and have been used for the preparation of chiral isoxazoline compounds (see, for example, WO 2011/104089 A1, which is incorporated herein by reference), it has surprisingly been discovered that certain substituents unexpectedly improve the selectivity of the reaction. It has been found that electron-donating substituents, such as alkoxy groups, on the aryl or heteroaryl group R improve the selectivity for the (S)-enantiomer if (IIIa) is used. In addition, multiple substitution of the aryl or heteroaryl group R with electron donating groups further improves the selectivity of the reaction for the (S)-enantiomer. Of course, if the stereochemistry of the chiral catalyst is reversed and (IIIb) is used, the selectivity is for the (R)-enantiomer.

Skilled persons in the art will understand that in some circumstances mixtures of the phase transfer catalysts described herein may be used to achieve the enantiomerically enriched isoxazoline compounds. Further, it will be understood that a given catalyst (for example, Formula (IIIa-13-1) may contain small amounts of other catalyst having a different group W (ethyl or vinyl) or R' (e.g. methoxy or hydrogen). Nevertheless, the presence of small amounts of catalysts substituted with other groups W and R' will still be useful for preparing the enantiomerically enriched isoxazoline compounds describe herein.

It has been found that using a quinine phase transfer catalyst of formula (IIIa) or (IIIb), wherein R is a phenyl group tri-substituted with aralkoxy groups, a surprisingly high selectivity for the formation of chiral isoxazoline compounds compared with known quinine phase transfer catalysts is achieved, even superior to quinine catalysts where the group corresponding to R is an aryl group substituted with one or more alkoxy groups. Thus, phase transfer catalysts of formula (IIIa) or (IIIb) wherein R is a phenyl group substituted by 1, 2, 3, 4 or 5 aralkoxy groups have been found to provide surprising selectivity in the formation of chiral isoxazoline compounds of formula (I) compared with known quinine phase transfer catalysts. In one preferred embodiment, the chiral quinine phase transfer catalysts are substituted with 1, 2, 3, 4 or 5 benzyloxy groups (—$OCH_2$Ph). In a particularly preferred embodiment, the invention provides chiral quinine phase transfer catalysts of formula (IIIa) wherein W is ethyl or vinyl, R' is methoxy or hydrogen and R is 3,4,5-tris(benzyloxy)phenyl3,4,5-tris(benzyloxy)phenyl. These catalysts have been shown to provide surprisingly improved selectivity in the reaction to prepare isoxazoline compounds of formula (I) enriched in the (S)-enantiomers.

Accordingly, in one embodiment, the invention provides a process for the enantioselective synthesis of an antiparasitic isoxazoline compound of formula (I) enriched in an enantiomer:

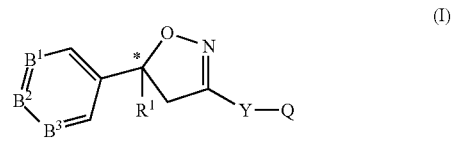

wherein $B^1$, $B^2$, B, $R^1$, Y and Q are as defined above, comprising reacting a compound of formula (II):

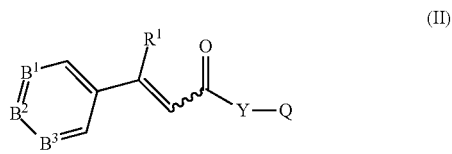

wherein B¹, B², B³, R¹, Y and Q are as defined for formula (I), with hydroxylamine in the presence of water, an organic solvent that is not miscible with water, a base and a chiral phase transfer catalyst of formula (IIIa) or (IIIb):

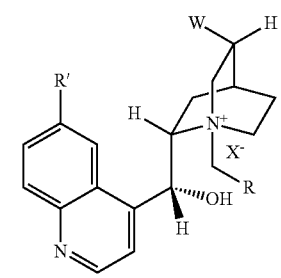

(IIIa)

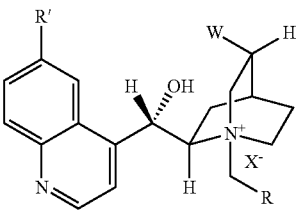

(IIIb)

wherein R is aryl or heteroaryl that is substituted with one or more aralkoxy, amino, alkylamino or dialkylamino groups, R' is hydrogen or $C_1$-$C_3$alkoxy, W is ethyl or vinyl and $X^-$ is an anion; and isolating the compound. In one embodiment, $X^-$ is a halide anion. In another embodiment, $X^-$ is chloride or bromide. In another embodiment, $X^-$ is a tosylate, mesylate, triflate, brosylate, nosylate or tresylate counter ion, or the like. In a preferred embodiment, the compound of formula (I) is isolated by crystallization from an aromatic solvent or a solvent mixture comprising an aromatic solvent. In one embodiment, the compound of formula (I) is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the compound of formula (I) is crystallized from toluene or a solvent mixture comprising toluene.

In another embodiment, the invention provides a process for the preparation of a mixture of isoxazoline compounds of the formula (S)-I and (R)-I below:

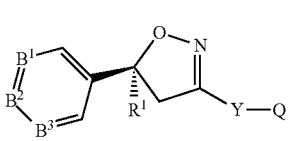

(S)-I

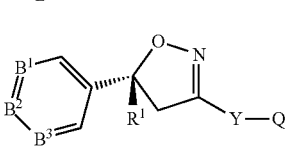

(R)-I wherein the mixture is enriched in (S)-I; and

B¹, B², B³, R¹, Y and Q have the same meanings as for formula (I) above;

comprising reacting a compound of formula (II):

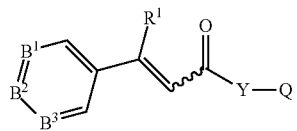

(II)

wherein B¹, B², B³, R¹, Y and Q are as defined for formula (I), with hydroxylamine in the presence of water, an organic solvent that is not miscible with water, a base and a chiral phase transfer catalyst of formula (IIIa):

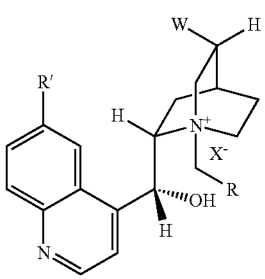

(IIIa)

wherein R is aryl or heteroaryl substituted with one or more aralkoxy, amino, alkylamino or dialkylamino groups, R' is hydrogen or $C_1$-$C_3$alkoxy, W is ethyl or vinyl and $X^-$ is an anion; and isolating the compound. In a preferred embodiment, the compound of formula (I) enriched in the (S)-enantiomer is isolated by crystallization from an aromatic solvent or a solvent mixture comprising an aromatic solvent. In one embodiment, the compound of formula (I) enriched in the (S)-enantiomer is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the compound of formula (I) enriched in the (S)-enantiomer is crystallized from toluene or a solvent mixture comprising toluene.

In another embodiment, the invention provides a process for the preparation of a mixture of isoxazoline compounds of the formula (S)-I and (R)-I below:

(S)-I (R)-I wherein the mixture is enriched in (R)-I; and

B¹, B², B³, R¹, Y and Q have the same meanings as for formula (I) above;

comprising reacting a compound of formula (II):

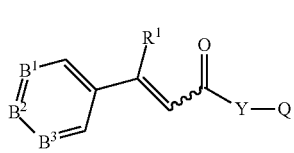
(II)

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIb):

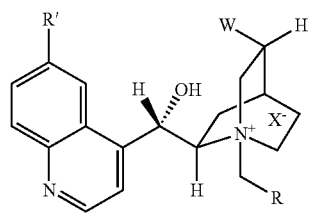
(IIIb)

wherein R is aryl or heteroaryl substituted with one or more aralkoxy, amino, alkylamino or dialkylamino groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment, the invention provides a process for the preparation of a mixture of isoxazoline compounds of the formula (S)-I and (R)-I below:

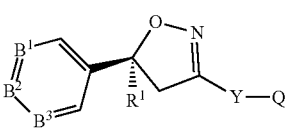
(S)-I

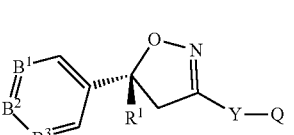
(R)-I wherein the mixture is enriched in (S)-I; and $B^1$, $B^2$, $B^3$, $R^1$, Y and Q have the same meanings as for formula (I) above;

comprising reacting a compound of formula (II):

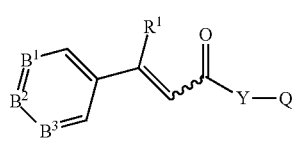
(II)

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

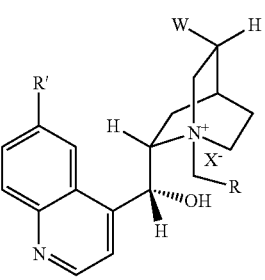
(IIIa)

wherein R is aryl or heteroaryl substituted with one or more benzyloxy groups (—OCH$_2$Ph), amino, $C_1$-$C_3$alkylamino or di-$C_1$-$C_3$-alkyamino groups; R' is hydrogen or $C_1$-$C_3$alkoxy, W is ethyl or vinyl and $X^-$ is an anion; and isolating the compound. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment, the invention provides a process for the synthesis of a mixture of enantiomers of formula (S)-I and (R)-I, wherein the mixture is enriched in an enantiomer in a weight:weight ratio of about 55:45 to about 99.9:0.1, (S)-I to (R)-I. In another embodiment, the invention provides a process for the synthesis of a mixture of enantiomers (S)-I and (R)-I which is enriched in (S)-I in a weight:weight ratio of about 65:35 to about 99:1, (S)-I to (R)-I. In yet another embodiment, the invention provides a process for the synthesis of a mixture of enantiomers (S)-I and (R)-I, wherein the mixture is enriched in (S)-I in a weight:weight ratio of about 70:30 to about 99:1, about 80:20 to about 99:1 or about 90:10 to about 99:1, (S)-I to (R)-I.

In another embodiment, the invention provides a process for the synthesis of a mixture of enantiomers of (S)-I and (R)-I, wherein the mixture is enriched in (S)-I in a weight:weight ratio of about 85:15 to about 95:5, (S)-I to (R)-I. In still another embodiment, the invention provides a process for the synthesis of a mixture of enantiomers of (S)-I and (R)-I, wherein the mixture is enriched in (S)-I a weight:weight ratio of about 87:13 to about 93:7, (S)-I to (R)-I. In another embodiment, the invention provides a process for the synthesis of a mixture of enantiomers (S)-I and (R)-I, wherein the mixture is enriched in (S)-I in a weight:weight ratio of 95:5 to 99:1, (S)-I to (R)-I.

In still another embodiment, the invention provides a process for the preparation of an isoxazoline compound of the formula (S)-I in substantially pure enantiomeric form (≥99:1, (S)-I to (R)-I):

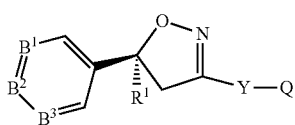
(S)-I wherein $B^1$, $B^2$, $B^3$, $R^1$, Y and Q have the same meanings as for formula (I) above; comprising reacting a compound of formula (II):

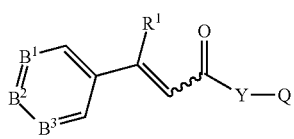
(II)

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

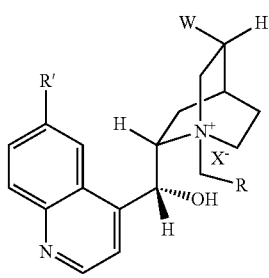
(IIIa)

wherein R is aryl or heteroaryl substituted with one or more benzyloxy (—OCH$_2$Ph) groups, W is ethyl or vinyl, R' is hydrogen or C$_1$-C$_3$alkoxy, and X$^-$ is an anion; and isolating the product by crystallization from an aromatic solvent or a solvent mixture comprising an aromatic solvent. In one embodiment, the compound of formula (S)-I is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the compound of formula (S)-I is crystallized from toluene or a solvent mixture comprising toluene.

In one embodiment, isolation of the product by crystallization from an aromatic solvent results in isolation of a crystalline solvate solid form of the desired enantiomer with the aromatic solvent which results in a surprising purification of the desired enantiomer from the reaction mixture because the racemic compound does not form the solvate form.

In one embodiment of the process, R in formula (IIIa) or (IIIb) is aryl or heteroaryl substituted with one aralkoxy group. In another embodiment, R is aryl or heteroaryl substituted with two aralkoxy groups. In yet another embodiment, R is aryl or heteroaryl substituted with three aralkoxy groups. In still another embodiment, R is aryl or heteroaryl substituted with four aralkoxy groups. In another embodiment, R is aryl or heteroaryl substituted with five aralkoxy groups.

In another embodiment of the process, R in formula (IIIa) or (IIIb) is aryl or heteroaryl substituted with one benzyloxy group (—OCH$_2$Ph) and R' is hydrogen or methoxy. In another embodiment, R is aryl or heteroaryl substituted with two benzyloxy groups and R' is hydrogen or methoxy. In yet another embodiment, R is aryl or heteroaryl substituted with three benzyloxy groups and R' is hydrogen or methoxy. In still another embodiment, R is aryl or heteroaryl substituted with four benzyloxy groups and R' is hydrogen or methoxy. In another embodiment, R is aryl or heteroaryl substituted with five benzyloxy groups and R' is hydrogen or methoxy.

In still another embodiment of the process, R in formula (IIIa) or (IIIb) is phenyl substituted with one aralkoxy group. In another embodiment, R is phenyl substituted with two aralkoxy groups. In yet another embodiment, R is phenyl substituted with three aralkoxy groups.

In still another embodiment, R is phenyl substituted with four aralkoxy groups. In another embodiment, R is phenyl substituted with five aralkoxy groups.

In another embodiment of the process, R in formula (IIIa) or (IIIb) is:

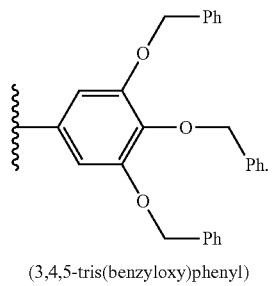 [SMILES: *c1cc(OCc2ccccc2)c(OCc2ccccc2)c(OCc2ccccc2)c1]
(3,4,5-tris(benzyloxy)phenyl)

In another embodiment of the process, R in formula (IIIa) or (IIIb) is phenyl substituted with one benzyloxy group (—OCH$_2$Ph) and R' is hydrogen or methoxy. In another embodiment, R is phenyl substituted with two benzyloxy groups and R' is hydrogen or methoxy. In yet another embodiment, R is phenyl substituted with three benzyloxy groups and R' is hydrogen or methoxy. In still another embodiment, R is phenyl substituted with four benzyloxy groups and R' is hydrogen or methoxy. In another embodiment, R is phenyl substituted with five benzyloxy groups and R' is hydrogen or methoxy.

In still another embodiment of the process, R in formula (IIIa) or (IIIb) is naphthyl substituted with one aralkoxy group. In another embodiment, R is naphthyl substituted with two aralkoxy groups. In yet another embodiment, R is naphthyl substituted with three aralkoxy groups. In still another embodiment, R is naphthyl substituted with four aralkoxy groups. In another embodiment, R is naphthyl substituted with five aralkoxy groups.

In another embodiment of the process, R in formula (IIIa) or (IIIb) is naphthyl substituted with one benzyloxy group (—OCH$_2$Ph) and R' is hydrogen or methoxy. In another embodiment, R is naphthyl substituted with two benzyloxy groups and R' is hydrogen or methoxy. In yet another embodiment, R is naphthyl substituted with three benzyloxy groups and R' is hydrogen or methoxy. In still another embodiment, R is naphthyl substituted with four benzyloxy groups and R' is hydrogen or methoxy. In another embodiment, R is naphthyl substituted with five benzyloxy groups and R' is hydrogen or methoxy.

In still another embodiment of the process, R in formula (IIIa) or (IIIb) is anthracenyl substituted with one aralkoxy group. In another embodiment, R is anthracenyl substituted with two aralkoxy groups. In yet another embodiment, R is anthracenyl substituted with three aralkoxy groups. In still another embodiment, R is anthracenyl substituted with four aralkoxy groups. In another embodiment, R is anthracenyl substituted with five aralkoxy groups.

In another embodiment of the process, R in formula (IIIa) or (IIIb) is anthracenyl substituted with one benzyloxy group (—OCH$_2$Ph) and R' is hydrogen or methoxy. In another embodiment, R is anthracenyl substituted with two benzyloxy groups and R' is hydrogen or methoxy. In yet another embodiment, R is anthracenyl substituted with three benzyloxy groups and R' is hydrogen or methoxy. In still another embodiment, R is anthracenyl substituted with four benzyloxy groups and R' is hydrogen or methoxy. In another embodiment, R is anthracenyl substituted with five benzyloxy groups and R' is hydrogen or methoxy.

In still another embodiment of the process, R in formula (IIIa) or (IIIb) is pyridyl substituted with one aralkoxy group. In another embodiment, R is pyridyl substituted with two aralkoxy groups. In yet another embodiment, R is pyridyl substituted with three aralkoxy groups.

In still another embodiment, R is pyridyl substituted with four aralkoxy groups. In another embodiment, R is pyridyl substituted with five aralkoxy groups.

In another embodiment of the process, R in formula (IIIa) or (IIIb) is pyridyl substituted with one benzyloxy group (—OCH$_2$Ph) and R' is hydrogen or methoxy. In another embodiment, R is pyridyl substituted with two benzyloxy groups and R' is hydrogen or methoxy. In yet another embodiment, R is pyridyl substituted with three benzyloxy groups and R' is hydrogen or methoxy. In still another embodiment, R is pyridyl substituted with four benzyloxy groups and R' is hydrogen or methoxy. In another embodiment, R is pyridyl substituted with five benzyloxy groups and R' is hydrogen or methoxy.

In still another embodiment of the process, R in formula (IIIa) or (IIIb) is pyrimidinyl substituted with one aralkoxy group. In another embodiment, R is pyrimidinyl substituted with two aralkoxy groups. In yet another embodiment, R is pyrimidinyl substituted with three aralkoxy groups. In still another embodiment, R is pyrimidinyl substituted with four aralkoxy groups. In another embodiment, R is pyrimidinyl substituted with five aralkoxy groups.

In another embodiment of the process, R in formula (IIIa) or (IIIb) is pyrimidinyl substituted with one benzyloxy group (—OCH$_2$Ph) and R' is hydrogen or methoxy. In another embodiment, R is pyrimidinyl substituted with two benzyloxy groups and R' is hydrogen or methoxy. In yet another embodiment, R is pyrimidinyl substituted with three benzyloxy groups and R' is hydrogen or methoxy. In still another embodiment, R is pyrimidinyl substituted with four benzyloxy groups and R' is hydrogen or methoxy. In another embodiment, R is pyrimidinyl substituted with five benzyloxy groups and R' is hydrogen or methoxy.

In still another embodiment of the process, R in formula (IIIa) or (IIIb) is quinolinyl substituted with one aralkoxy group. In another embodiment, R is quinolinyl substituted with two aralkoxy groups. In yet another embodiment, R is quinolinyl substituted with three aralkoxy groups. In still another embodiment, R is quinolinyl substituted with four aralkoxy groups. In another embodiment, R is quinolinyl substituted with five aralkoxy groups.

In another embodiment of the process, R in formula (IIIa) or (IIIb) is quinolinyl substituted with one benzyloxy group (—OCH$_2$Ph) and R' is hydrogen or methoxy. In another embodiment, R is quinolinyl substituted with two benzyloxy groups and R' is hydrogen or methoxy. In yet another embodiment, R is quinolinyl substituted with three benzyloxy groups and R' is hydrogen or methoxy. In still another embodiment, R is quinolinyl substituted with four benzyloxy groups and R' is hydrogen or methoxy. In another embodiment, R is quinolinyl substituted with five benzyloxy groups and R' is hydrogen or methoxy.

In still another embodiment of the process, R in formula (IIIa) or (IIIb) is quinolin-4-yl substituted with one aralkoxy group. In another embodiment, R is quinolin-4-yl substituted with two aralkoxy groups. In yet another embodiment, R is quinolin-4-yl substituted with three aralkoxy groups. In still another embodiment, R is quinolin-4-yl substituted with four aralkoxy groups. In another embodiment, R is quinolin-4-yl substituted with five aralkoxy groups.

In another embodiment of the process, R in formula (IIIa) or (IIIb) is quinolin-4-yl substituted with one benzyloxy group (—OCH$_2$Ph) and R' is hydrogen or methoxy. In another embodiment, R is quinolin-4-yl substituted with two benzyloxy groups and R' is hydrogen or methoxy. In yet another embodiment, R is quinolin-4-yl substituted with three benzyloxy groups and R' is hydrogen or methoxy. In still another embodiment, R is quinolin-4-yl substituted with four benzyloxy groups and R' is hydrogen or methoxy. In another embodiment, R is quinolin-4-yl substituted with five benzyloxy groups and R' is hydrogen or methoxy.

In still another embodiment of the process, R in formula (IIIa) or (IIIb) is isoquinolinyl substituted with one aralkoxy group. In another embodiment, R is isoquinolinyl substituted with two aralkoxy groups. In yet another embodiment, R is isoquinolinyl substituted with three aralkoxy groups. In still another embodiment, R is isoquinolinyl substituted with four aralkoxy groups. In another embodiment, R is isoquinolinyl substituted with five aralkoxy groups.

In another embodiment of the process, R in formula (IIIa) or (IIIb) is isoquinolinyl substituted with one benzyloxy group (—OCH$_2$Ph) and R' is hydrogen or methoxy. In another embodiment, R is isoquinolinyl substituted with two benzyloxy groups and R' is hydrogen or methoxy. In yet another embodiment, R is isoquinolinyl substituted with three benzyloxy groups and R' is hydrogen or methoxy. In still another embodiment, R is isoquinolinyl substituted with four benzyloxy groups and R' is hydrogen or methoxy. In another embodiment, R is isoquinolinyl substituted with five benzyloxy groups and R' is hydrogen or methoxy.

In still another embodiment of the process, R in formula (IIIa) or (IIIb) is acridinyl substituted with one aralkoxy group. In another embodiment, R is acridinyl substituted with two aralkoxy groups. In yet another embodiment, R is acridinyl substituted with three aralkoxy groups. In still another embodiment, R is acridinyl substituted with four aralkoxy groups. In another embodiment, R is acridinyl substituted with five aralkoxy groups.

In another embodiment of the process, R in formula (IIIa) or (IIIb) is acridinyl substituted with one benzyloxy group (—OCH$_2$Ph) and R' is hydrogen or methoxy. In another embodiment, R is acridinyl substituted with two benzyloxy groups and R' is hydrogen or methoxy. In yet another embodiment, R is acridinyl substituted with three benzyloxy groups and R' is hydrogen or methoxy. In still another embodiment, R is acridinyl substituted with four benzyloxy groups and R' is hydrogen or methoxy. In another embodiment, R is acridinyl substituted with five benzyloxy groups and R' is hydrogen or methoxy.

In still another embodiment of the process, R in formula (IIIa) or (IIIb) is acridin-9-yl substituted with one aralkoxy group. In another embodiment, R is acridin-9-yl substituted with two aralkoxy groups. In yet another embodiment, R is acridin-9-yl substituted with three aralkoxy groups. In still another embodiment, R is acridin-9-yl substituted with four aralkoxy groups. In another embodiment, R is acridin-9-yl substituted with five aralkoxy groups.

In another embodiment of the process, R in formula (IIIa) or (IIIb) is acridin-9-yl substituted with one benzyloxy group (—OCH$_2$Ph) and R' is hydrogen or methoxy. In another embodiment, R is acridin-9-yl substituted with two benzyloxy groups and R' is hydrogen or methoxy. In yet another embodiment, R is acridin-9-yl substituted with three benzyloxy groups and R' is hydrogen or methoxy. In still another embodiment, R is acridin-9-yl substituted with four benzyloxy groups and R' is hydrogen or methoxy. In another embodiment, R is acridin-9-yl substituted with five benzyloxy groups and R' is hydrogen or methoxy.

In another embodiment of the process, R in formula (IIIa) or (IIIb) is phenyl, naphthyl, anthracenyl, pyridyl, pyrimidinyl, quinolinyl, quinolin-4-yl, isoquinolinyl, acridinyl or acridin-9-yl substituted with one amino, $C_1$-$C_3$alkylamino or di-$C_1$-$C_3$-alkyl amino groups and R' is hydrogen or methoxy. In another embodiment, R is phenyl, naphthyl, anthracenyl, pyridyl, pyrimidinyl, quinolinyl, quinolin-4-yl, isoquinolinyl, acridinyl or acridin-9-yl substituted with two amino, $C_1$-$C_3$alkylamino or di-$C_1$-$C_3$-alkyl amino groups and R' is hydrogen or methoxy. In yet another embodiment, R is phenyl, naphthyl, anthracenyl, pyridyl, pyrimidinyl, quinolinyl, quinolin-4-yl, isoquinolinyl, acridinyl or acridin-9-yl substituted with three amino, $C_1$-$C_3$alkylamino or di-$C_1$-$C_3$-alkyl amino groups and R' is hydrogen or methoxy. In still another embodiment, R is phenyl, naphthyl, anthracenyl, pyridyl, pyrimidinyl, quinolinyl, quinolin-4-yl, isoquinolinyl, acridinyl or acridin-9-yl substituted with four amino, $C_1$-$C_3$alkylamino or di-$C_1$-$C_3$-alkyl amino groups and R' is hydrogen or methoxy. In another embodiment, R is phenyl, naphthyl, anthracenyl, pyridyl, pyrimidinyl, quinolinyl, quinolin-4-yl, isoquinolinyl, acridinyl or acridin-9-yl substituted with five amino, $C_1$-$C_3$alkylamino or di-$C_1$-$C_3$-alkyl amino groups and R' is hydrogen or methoxy.

In another embodiment of the process, R in formula (IIIa) or (IIIb) is phenyl substituted with one amino, $C_1$-$C_3$alkylamino or di-$C_1$-$C_3$-alkyl amino groups and R' is hydrogen or methoxy. In another embodiment, R is phenyl substituted with two amino, $C_1$-$C_3$alkylamino or di-$C_1$-$C_3$-alkyl amino groups and R' is hydrogen or methoxy. In yet another embodiment, R is phenyl substituted with three amino, $C_1$-$C_3$alkylamino or di-$C_1$-$C_3$-alkyl amino groups and R' is hydrogen or methoxy. In still another embodiment, R is phenyl substituted with four amino, $C_1$-$C_3$alkylamino or di-$C_1$-$C_3$-alkyl amino groups and R' is hydrogen or methoxy. In another embodiment, R is phenyl substituted with five amino, $C_1$-$C_3$alkylamino or di-$C_1$-$C_3$-alkyl amino groups and R' is hydrogen or methoxy.

In one embodiment of the invention, $B^1$, $B^2$, $B^3$ in the compounds of Formula (I) or Formula (II) are C—R and each R is independently H, halogen, $C_1$-$C_6$alkyl or $C_1$-$C_6$haloalkyl. In another embodiment, $B^1$, $B^2$, $B^3$ in Formula (I) or Formula (II) are C—R and each R is independently H, halogen, $C_1$-$C_3$alkyl or $C_1$-$C_3$haloalkyl. In one embodiment, $B^1$, $B^2$, $B^3$ in Formula (I) or Formula (II) are C—R and each R is independently H, Cl, F, $C_1$-$C_3$alkyl or $C_1$-$C_3$fluoroalkyl. In another embodiment, $B^1$, $B^2$, $B^3$ in Formula (I) or Formula (II) are C—R and each R is independently H, Cl, F or $CF_3$.

In one embodiment of the invention, Y in formula (I) and formula (II) is optionally substituted phenylene. In another embodiment, Y is optionally substituted naphthylene. In another embodiment, Y is an optionally substituted 5- or 6-membered heteroarylene containing 1, 2 or 3 atoms selected from S, N and O. In yet another embodiment, Y is an optionally substituted bicyclic heteroarylene containing 1, 2 or 3 atoms selected from S, N and O.

In another embodiment of the process of the invention, Y is selected from Y-1, Y-2, Y-3, Y-4 where Z is nitrogen or CH, Y-5 or Y-6:

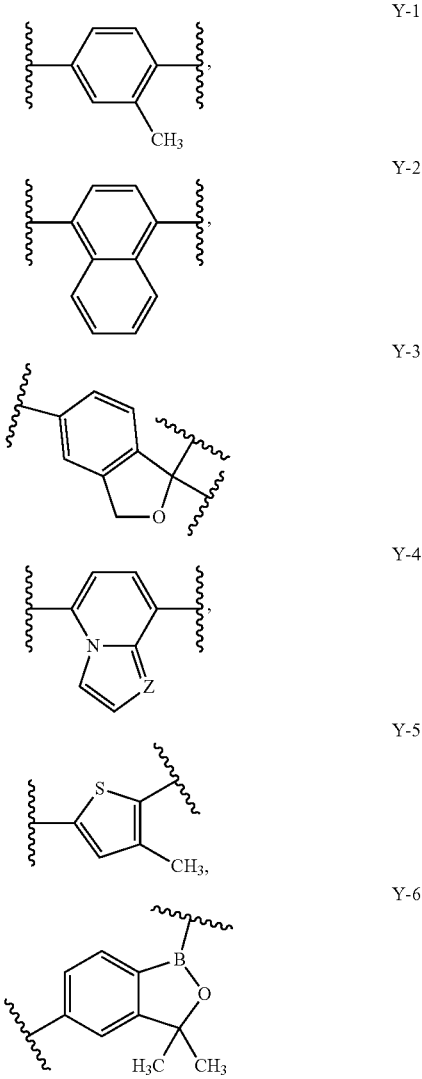

In one embodiment of the invention, the group Q in Formula (I) or Formula (II) is T-$NR^2R^3$. In another embodiment, Q is T-$NR^2R^3$ wherein $R^2$ is H or $C_1$-$C_3$alkyl and $R^3$ is $C_1$-$C_3$alkyl optionally substituted by $R^4$. In yet another embodiment, Q is T-$NR^2R^3$ wherein $R^2$ is H and $R^3$ is $C_1$-$C_3$alkyl optionally substituted by alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl. In another embodiment, Q is T-NR$^2$R$^3$ wherein R$^2$ is H and R$^3$ is C$_1$-C$_3$alkyl optionally substituted by alkylthio, haloalkylthio, alkylaminocarbonyl, dialkylaminocarbonyl, haloalkylaminocarbonyl or dihaloalkylaminocarbonyl. In still another embodiment, Q is —C(O)NHCH$_2$C(O)NHCH$_2$CF$_3$. In yet another embodiment, Q is —C(O)CH$_2$S(O)$_2$CH$_3$. In another embodiment, Q is —C(O)NHCH$_2$CH$_2$SCH$_3$. In another embodiment, Q is the group (—CH$_2$—)(—CH$_2$—)N(CO)CH$_2$S(O)$_2$CH$_3$.

In another embodiment of the invention, a process is provided for the synthesis of a compound of formula (I) enriched in the (S)-enantiomer wherein:

B$^1$ and B$^3$ are independently C—Cl or C—CF$_3$;
B$^2$ is C—H, C—Cl or C—F;
R$^1$ is CF$_3$;
Y is Y-1, Y-2, Y-4 or Y-5; and
Q is —C(O)—NR$^2$R$^3$ wherein R$^2$ is H and R$^3$ is C$_1$-C$_3$alkyl optionally substituted by alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl;

comprising reacting a compound of formula (II):

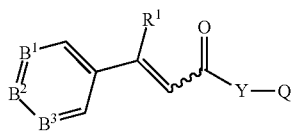

(II)

wherein B$^1$, B$^2$, B$^3$, R$^1$, Y and Q are as defined for formula (I), with hydroxylamine in the presence of water, an organic solvent that is not miscible with water, a base and a chiral phase transfer catalyst of formula (IIIa):

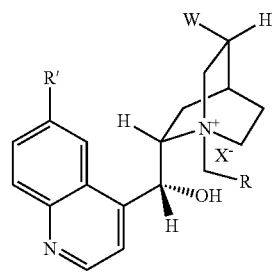

(IIIa)

wherein R is aryl or heteroaryl substituted with one or more benzyloxy (—OCH$_2$Ph) groups, W is ethyl or vinyl, R' is hydrogen or C$_1$-C$_3$alkoxy, and X$^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

B$^1$ and B$^3$ are independently C—Cl or C—CF$_3$;
B$^2$ is C—H, C—Cl or C—F;
R$^1$ is CF$_3$;
Y is Y-1, Y-2, Y-4 or Y-5; and
Q is —C(O)—NR$^2$R$^3$ wherein R$^2$ is H and R$^3$ is C$_1$-C$_3$alkyl optionally substituted by C$_1$-C$_3$alkylthio, C$_1$-C$_3$haloalkylthio, C$_1$-C$_3$alkylsulfinyl, C$_1$-C$_3$haloalkylsulfinyl, C$_1$-C$_3$alkylsulfonyl, C$_1$-C$_3$haloalkylsulfonyl, C$_1$-C$_3$alkylaminocarbonyl, C$_1$-C$_3$dialkylaminocarbonyl, C$_1$-C$_3$haloalkylaminocarbonyl or C$_1$-C$_3$dihaloalkylaminocarbonyl;

comprising reacting a compound of formula (II):

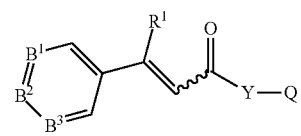

(II)

wherein B$^1$, B$^2$, B$^3$, R$^1$, Y and Q are as defined for formula (I), with hydroxylamine in the presence of water, an organic solvent that is not miscible with water, a base and a chiral phase transfer catalyst of formula (IIIa):

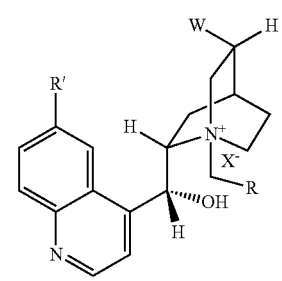

(IIIa)

wherein R is 3,4,5-tris(benzyloxy)phenyl;
W is ethyl or vinyl, R' is hydrogen or C$_1$-C$_3$alkoxy, and X$^-$ is an anion; and isolating the product.

In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

B$^1$ and B$^3$ are independently C—Cl or C—CF$_3$;
B$^2$ is C—H, C—Cl or C—F;
R$^1$ is CF$_3$;
Y is Y-1, Y-2, Y-4 or Y-5; and
Q is —C(O)CH$_2$S(O)$_2$CH$_3$, —C(O)NHCH$_2$CH$_2$SCH$_3$ or —C(O)NHCH$_2$C(O)NHCH$_2$CF$_3$;

comprising reacting a compound of formula (II):

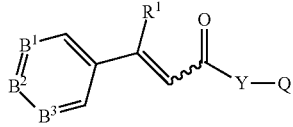

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

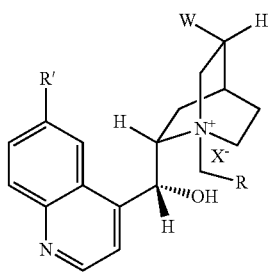

wherein R is aryl or heteroaryl substituted with one or more benzyloxy (—OCH$_2$Ph) groups, W is ethyl or vinyl, R' is hydrogen or $C_1$-$C_3$alkoxy, and X$^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

$B^1$ and $B^3$ are independently C—Cl or C—CF$_3$;
$B^2$ is C—H, C—Cl or C—F;
$R^1$ is CF$_3$;
Y is Y-1, Y-2, Y-4 or Y-5; and
Q is —C(O)CH$_2$S(O)$_2$CH$_3$, —C(O)NHCH$_2$CH$_2$SCH$_3$ or —C(O)NHCH$_2$C(O)NHCH$_2$CF$_3$;
comprising reacting a compound of formula (II):

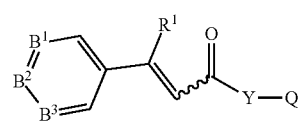

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

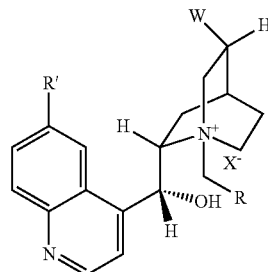

wherein R is 3,4,5-tris(benzyloxy)phenyl;
W is ethyl or vinyl, R' is hydrogen or $C_1$-$C_3$alkoxy, and X$^-$ is an anion; and isolating the product.

In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

$B^1$ and $B^3$ are independently C—Cl or C—CF$_3$; $B^2$ is C—H or C—F;
$R^1$ is CF$_3$;
Y is Y-2; and
Q is —C(O)—NR$^2$R$^3$ wherein R$^2$ is H and R$^3$ is $C_1$-$C_3$alkyl optionally substituted by alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl;
comprising reacting a compound of formula (II):

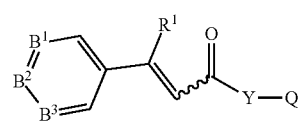

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

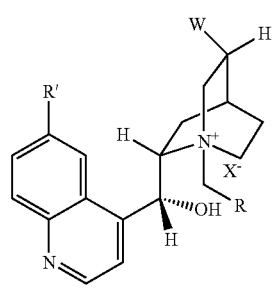

wherein R is aryl or heteroaryl substituted with one or more benzyloxy (—OCH$_2$Ph) groups, W is ethyl or vinyl, R' is hydrogen or C$_1$-C$_3$alkoxy, and X$^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

B$^1$ and B$^3$ are independently C—Cl or C—CF$_3$; B$^2$ is C—H or C—F;

R$^1$ is CF$_3$;

Y is Y-2; and

Q is —C(O)—NR$^2$R$^3$ wherein R$^2$ is H and R$^3$ is C$_1$-C$_3$alkyl optionally substituted by alkylthio, haloalkylthio, alkylsulfinyl, haloalkylsulfinyl, alkylsulfonyl, haloalkylsulfonyl, alkylaminocarbonyl, dialkylaminocarbonyl, haloalkylaminocarbonyl or dihaloalkylaminocarbonyl; comprising reacting a compound of formula (II):

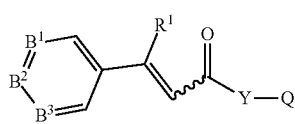

(II)

wherein B$^1$, B$^2$, B$^3$, R$^1$, Y and Q are as defined for formula (I), with hydroxylamine in the presence of water, an organic solvent that is not miscible with water, a base and a chiral phase transfer catalyst of formula (IIIa):

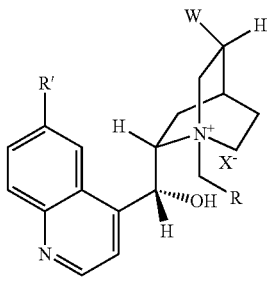

(IIIa)

wherein R is aryl or heteroaryl substituted with one or more C$_1$-C$_3$alkoxy groups, W is ethyl or vinyl, R' is hydrogen or C$_1$-C$_3$alkoxy, and X$^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

B$^1$ and B$^3$ are independently C—Cl or C—CF$_3$; B$^2$ is C—H or C—F;

R$^1$ is CF$_3$;

Y is Y-2; and

Q is —C(O)—NR$^2$R$^3$ wherein R$^2$ is H and R$^3$ is C$_1$-C$_3$alkyl optionally substituted by C$_1$-C$_3$alkylthio, C$_1$-C$_3$haloalkylthio, C$_1$-C$_3$alkylsulfinyl, C$_1$-C$_3$haloalkylsulfinyl, C$_1$-C$_3$alkylsulfonyl, C$_1$-C$_3$haloalkylsulfonyl, C$_1$-C$_3$alkylaminocarbonyl, C$_1$-C$_3$dialkylaminocarbonyl, C$_1$-C$_3$haloalkylaminocarbonyl or C$_1$-C$_3$dihaloalkylaminocarbonyl; comprising reacting a compound of formula (II):

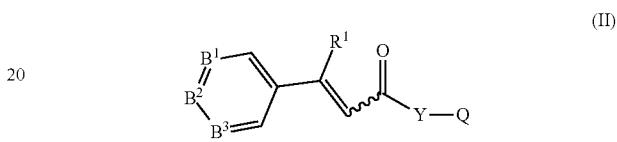

(II)

wherein B$^1$, B$^2$, B$^3$, R$^1$, Y and Q are as defined for formula (I), with hydroxylamine in the presence of water, an organic solvent that is not miscible with water, a base and a chiral phase transfer catalyst of formula (IIIa):

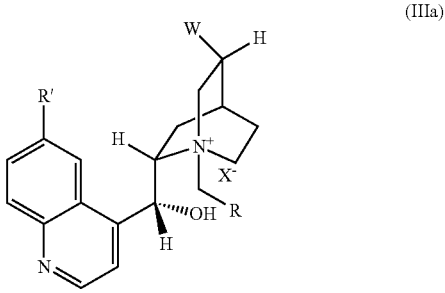

(IIIa)

wherein R is 3,4,5-tris(benzyloxy)phenyl;

W is ethyl or vinyl, R' is hydrogen or C$_1$-C$_3$alkoxy, and X$^-$ is an anion; and isolating the product.

In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

B$^1$ and B$^3$ are independently C—Cl or C—CF$_3$; B$^2$ is C—H or C—F;

R$^1$ is CF$_3$;

Y is Y-2; and

Q is —C(O)—NR$^2$R$^3$ wherein R$^2$ is H and R$^3$ is C$_1$-C$_3$alkyl optionally substituted by C$_1$-C$_3$alkylthio, C$_1$-C$_3$haloalkylthio, C$_1$-C$_3$alkylsulfinyl, C$_1$-C$_3$haloalkylsulfinyl, C$_1$-C$_3$alkylsulfonyl, C$_1$-C$_3$haloalkylsulfonyl, C$_1$-C$_3$alkylaminocarbonyl, $C_1$-$C_3$dialkylaminocarbonyl, $C_1$-$C_3$haloalkylaminocarbonyl or $C_1$-$C_3$dihaloalkylaminocarbonyl;
comprising reacting a compound of formula (II):

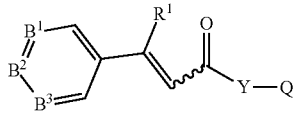
(II)

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

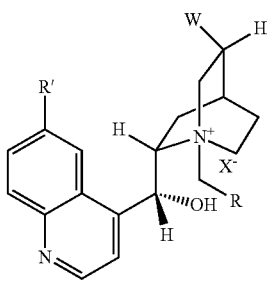
(IIIa)

wherein R is a phenyl ring independently substituted at the 3-, 4- and 5-positions with methoxy, ethoxy or isopropoxy; W is ethyl or vinyl, R' is hydrogen or $C_1$-$C_3$alkoxy, and $X^-$ is an anion; and isolating the product.

In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

$B^1$ and $B^3$ are independently C—Cl or C—$CF_3$; $B^2$ is C—H or C—F;
$R^1$ is $CF_3$;
Y is Y-2; and
Q is —C(O)NHCH$_2$C(O)NHCH$_2$CF$_3$ or —C(O)NHCH$_2$CH$_2$SCH$_3$;
comprising reacting a compound of formula (II):

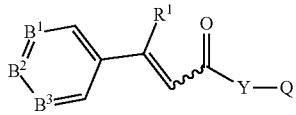
(II)

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

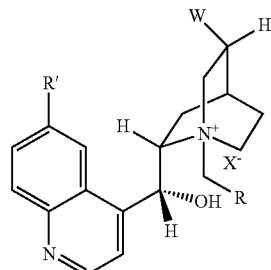
(IIIa)

wherein R is aryl or heteroaryl substituted with one, two or three $C_1$-$C_3$alkoxy groups, W is ethyl or vinyl, R' is hydrogen or $C_1$-$C_3$alkoxy, and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

$B^1$ and $B^3$ are independently C—Cl or C—$CF_3$; $B^2$ is C—H or C—F;
$R^1$ is $CF_3$;
Y is Y-2; and
Q is —C(O)NHCH$_2$C(O)NHCH$_2$CF$_3$ or —C(O)NHCH$_2$CH$_2$SCH$_3$;
comprising reacting a compound of formula (II):

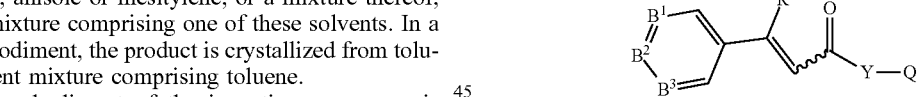
(II)

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

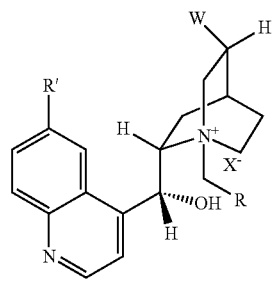
(IIIa)

wherein R is phenyl independently substituted at the 3-, 4- and 5-positions with methoxy, ethoxy or isopropoxy;

W is ethyl or vinyl, R' is hydrogen or $C_1$-$C_3$alkoxy, and $X^-$ is an anion; and isolating the product.

In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

$B^1$ and $B^3$ are independently C—Cl or C—$CF_3$; $B^2$ is C—H or C—F;

$R^1$ is $CF_3$;

Y is Y-2; and

Q is —C(O)NHCH$_2$C(O)NHCH$_2$CF$_3$ or —C(O)NHCH$_2$CH$_2$SCH$_3$;

comprising reacting a compound of formula (II):

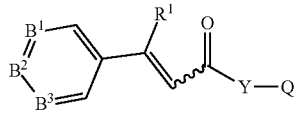

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

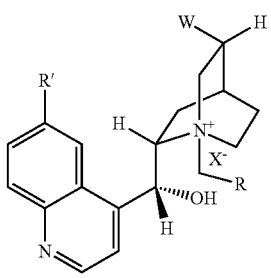

wherein R is aryl or heteroaryl substituted with one, two or three benzyloxy (—OCH$_2$Ph) groups, W is ethyl or vinyl, R' is hydrogen or $C_1$-$C_3$alkoxy, and $X^-$ is an anion; and isolating the product.

In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment of the invention, a process is provided for the synthesis of a compound of formula (I) enriched in the (S)-enantiomer wherein:

$B^1$ and $B^3$ are independently C—Cl or C—$CF_3$; $B^2$ is C—H or C—F;

$R^1$ is $CF_3$;

Y is Y-2; and

Q is —C(O)NHCH$_2$C(O)NHCH$_2$CF$_3$ or —C(O)NHCH$_2$CH$_2$SCH$_3$;

comprising reacting a compound of formula (II):

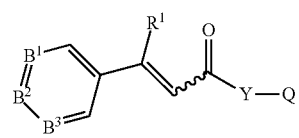

wherein $B^1$, $B^2$, $B^3$, $R^1$, Y and Q are as defined for formula (I), with hydroxylamine in the presence of water, an organic solvent that is not miscible with water, a base and a chiral phase transfer catalyst of formula (IIIa):

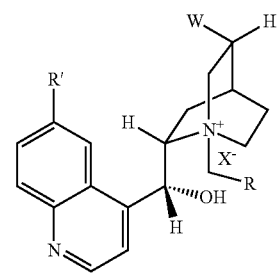

wherein R is 3,4,5-tris(benzyloxy)phenyl;

W is ethyl or vinyl, R' is hydrogen or $C_1$-$C_3$alkoxy, and $X^-$ is an anion; and isolating the product.

In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

As described above, the antiparasitic compounds afoxolaner, fluralaner, sarolaner and lotilaner all have an asymmetric quaternary carbon atom on the isoxazoline ring. One of the enantiomers of each of these compounds is substantially more active against ectoparasites such as fleas and ticks than the other enantiomer. With respect to afoxolaner, the (S)-enantiomer is the more active enantiomer. Saronaler is the pure (S)-enantiomer, lotilaner is the pure (S)-enantiomer, and it is believed that the (S)-enantiomer of fluralaner is also the more active enantiomer.

Thus, in a second aspect, the invention provides a process for the preparation of an isoxazoline compound of Formula IA, wherein $X^1$, $X^2$ and $X^3$ are each independently H, halogen, $C_1$-$C_3$alkyl or $C_1$-$C_3$haloalkyl, which is enriched in the (S)-enantiomer:

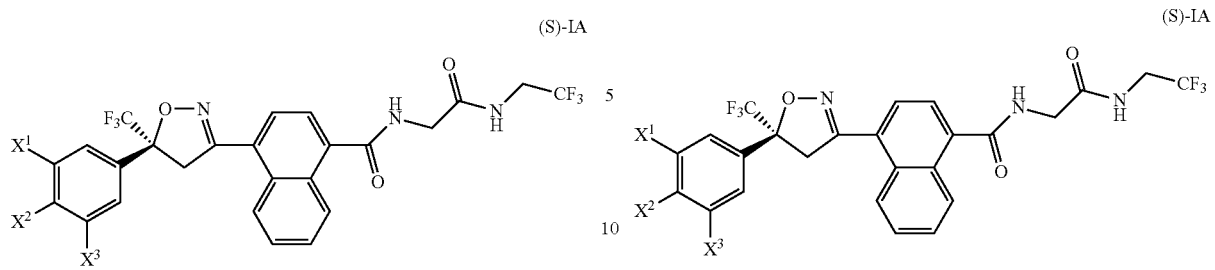

(S)-IA comprising reacting a compound of formula (IIA):

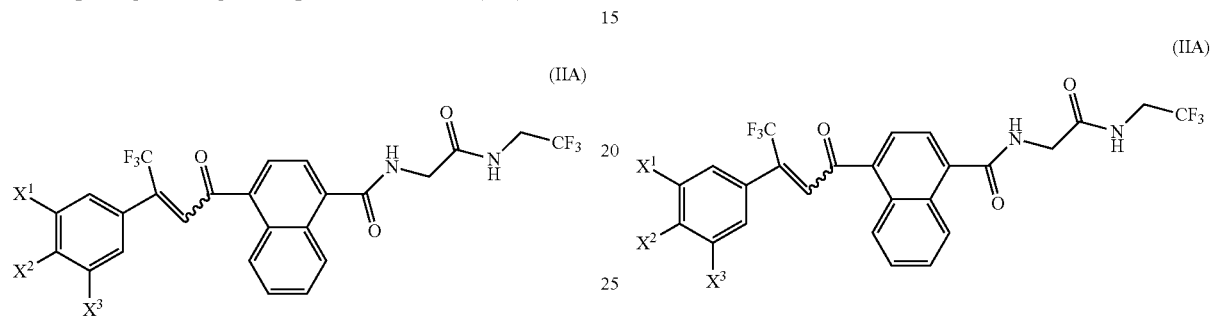

(IIA)

wherein $X^1$, $X^2$ and $X^3$ have the meanings described above for Formula IA, with hydroxylamine in the presence of water, an organic solvent that is not miscible with water, a base and a chiral phase transfer catalyst of formula (IIIa):

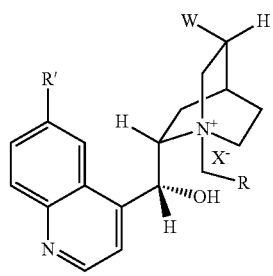

(IIIa)

wherein R is aryl or heteroaryl optionally substituted with one or more $C_1$-$C_3$alkoxy or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In another embodiment, the invention provides a process for the preparation of an isoxazoline compound of Formula IA, wherein $X^1$, $X^2$ and $X^3$ are each independently H, chloro, fluoro or $CF_3$, which is enriched in the (S)-enantiomer:

(S)-IA comprising reacting a compound of formula (IIA):

(IIA)

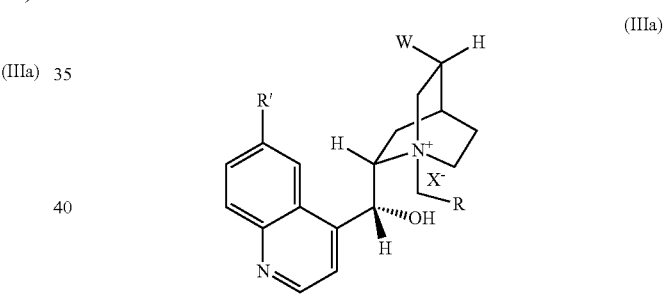

wherein $X^1$, $X^2$ and $X^3$ are H, chloro, fluoro or $CF_3$, with hydroxylamine in the presence of water, an organic solvent that is not miscible with water, a base and a chiral phase transfer catalyst of formula (IIIa):

(IIIa)

wherein R is aryl or heteroaryl optionally substituted with one or more $C_1$-$C_3$alkoxy or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the process for the preparation of (S)-IA, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment of the process for the preparation of Formula IA enriched in the (S)-enantiomer, R in the catalyst of formula (IIIa) is phenyl substituted by 1, 2 or 3 C$_1$-C$_6$alkoxy groups, and R' is hydrogen or methoxy. In another embodiment, R is phenyl substituted by 1, 2 or 3 methoxy, ethoxy or isopropoxy, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy or ethoxy groups, R' is hydrogen and W is ethyl.

In another embodiment of the process for the preparation of Formula IA enriched in the (S)-enantiomer, R in the catalyst of formula (IIIa) is phenyl independently substituted at the 3-, 4- and 5-positions with methoxy, ethoxy or isopropoxy; R' is methoxy and W is vinyl. In another embodiment, R is phenyl independently substituted at the 3-, 4- and 5-positions with methoxy, ethoxy or isopropoxy; R' is hydrogen and W is vinyl. In another embodiment, R is phenyl independently substituted at the 3-, 4- and 5-positions with methoxy, ethoxy or isopropoxy; R' is methoxy and W is ethyl. In another embodiment, R is phenyl independently substituted at the 3-, 4- and 5-positions with methoxy, ethoxy or isopropoxy; R' is hydrogen and W is ethyl.

In yet another embodiment of the process for the preparation of Formula IA enriched in the (S)-enantiomer, R in the catalyst of formula (IIIa) is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl.

In another embodiment of the process for the preparation of Formula IA enriched in the (S)-enantiomer, R in the catalyst of formula (IIIa) is 3,4,5-tris(benzyloxy)phenyl; R' is methoxy and W is vinyl. In another embodiment, R is 3,4,5-tris(benzyloxy)phenyl; R' is hydrogen, and W is vinyl. In yet another embodiment, R is 3,4,5-tris(benzyloxy)phenyl; R' is methoxy and W is ethyl. In still another embodiment, R is 3,4,5-tris(benzyloxy)phenyl; R' is hydrogen and W is ethyl.

In another embodiment, the invention provides a process for the preparation of afoxolaner enriched in the (S)-enantiomer:

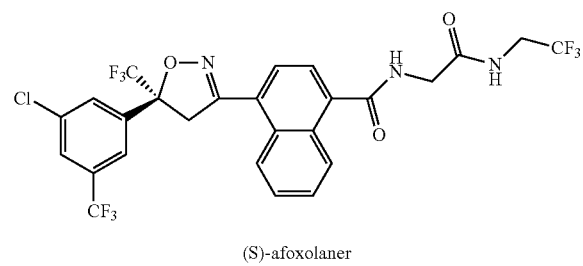 [SMILES: O=C(CNC(=O)c1ccc(C2=NO[C@@](c3cc(Cl)cc(C(F)(F)F)c3)(C(F)(F)F)C2)c2ccccc12)NCC(F)(F)F]

(S)-afoxolaner comprising reacting a compound of formula (IIA-1):

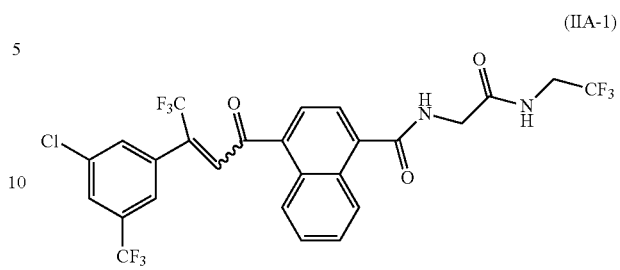

(IIA-1)

with hydroxylamine in the presence of water, an organic solvent that is not miscible with water, a base and a chiral phase transfer catalyst of formula (IIIa):

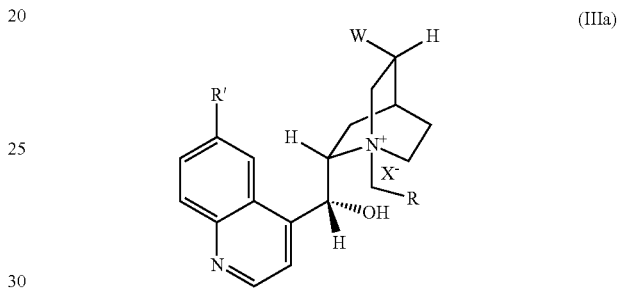

(IIIa)

wherein R is aryl or heteroaryl optionally substituted with one or more C$_1$-C$_3$alkoxy or aralkoxy groups, R' is hydrogen or C$_1$-C$_3$alkoxy, W is ethyl or vinyl and X$^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the synthesis of afoxolaner enriched in the (S)-enantiomer, R in the catalyst of formula (IIIa) is aryl or heteroaryl substituted by one or more C$_1$-C$_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment of the synthesis of afoxolaner enriched in the (S)-enantiomer, R in the catalyst of formula (IIIa) is phenyl substituted by 1, 2 or 3 C$_1$-C$_6$alkoxy groups and R' is hydrogen or methoxy. In another embodiment R is phenyl substituted by 1, 2 or 3 methoxy or ethoxy and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl.

In another embodiment of the synthesis of afoxolaner enriched in the (S)-enantiomer, R in the catalyst of formula (IIIa) is phenyl independently substituted at the 3-, 4- and 5-positions with methoxy, ethoxy or isopropoxy; R' is methoxy and W is vinyl. In another embodiment of the synthesis of afoxolaner enriched in the (S)-enantiomer, R in the catalyst of formula (IIIa) is phenyl independently substituted at the 3-, 4- and 5-positions with methoxy, ethoxy or isopropoxy; R' is hydrogen and W is vinyl. In another embodiment of the synthesis of afoxolaner enriched in the (S)-enantiomer, R in the catalyst of formula (IIIa) is phenyl independently substituted at the 3-, 4- and 5-positions with methoxy, ethoxy or isopropoxy; R' is methoxy and W is ethyl. In another embodiment of the synthesis of afoxolaner enriched in the (S)-enantiomer, R in the catalyst of formula (IIIa) is phenyl independently substituted at the 3-, 4- and 5-positions with methoxy, ethoxy or isopropoxy; R' is hydrogen and W is ethyl.

In yet another embodiment of the synthesis of afoxolaner enriched in the (S)-enantiomer, R in the catalyst of formula (IIIa) is phenyl substituted by 1, 2 or 3 benzyloxy and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl.

In another embodiment of the synthesis of afoxolaner enriched in the (S)-enantiomer, R in the catalyst of formula (IIIa) is 3,4,5-tris(benzyloxy)phenyl; R' is methoxy and W is vinyl. In another embodiment of the synthesis of afoxolaner enriched in the (S)-enantiomer, R in the catalyst of formula (IIIa) is 3,4,5-tris(benzyloxy)phenyl; R' is hydrogen, and W is vinyl. In another embodiment of the synthesis of afoxolaner enriched in the (S)-enantiomer, R in the catalyst of formula (IIIa) is 3,4,5-tris(benzyloxy)phenyl; R' is methoxy and W is ethyl. In another embodiment of the synthesis of afoxolaner enriched in the (S)-enantiomer, R in the catalyst of formula (IIIa) is 3,4,5-tris(benzyloxy)phenyl; R' is hydrogen and W is ethyl.

In another embodiment, the invention provides a process for the preparation of an isoxazoline compound of Formula IB enriched in the (S)-enantiomer:

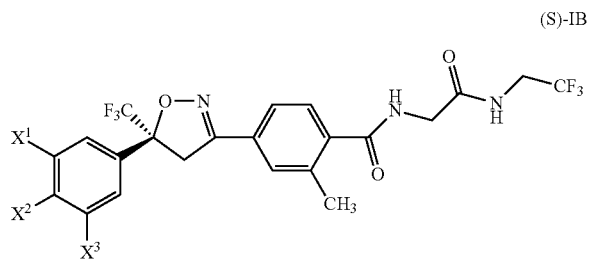

(S)-IB wherein $X^1$, $X^2$ and $X^3$ are each independently H, chloro, fluoro or $CF_3$;

comprising reacting a compound of formula (IIB):

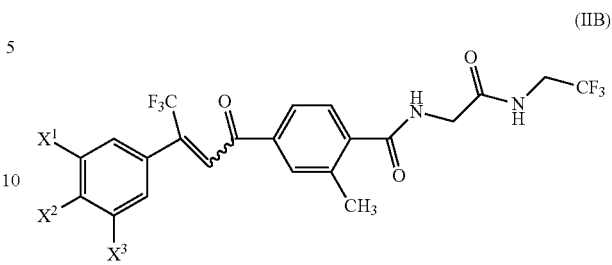

(IIB)

wherein $X^1$, $X^2$ and $X^3$ are H, chloro, fluoro or $CF_3$, with hydroxylamine in the presence of water, an organic solvent that is not miscible with water, a base and a chiral phase transfer catalyst of formula (IIIa):

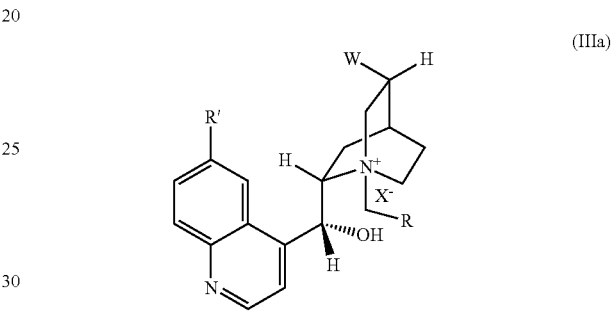

(IIIa)

wherein R is aryl or heteroaryl optionally substituted with one or more $C_1$-$C_3$alkoxy, amino, $C_1$-$C_3$-alkylamino, $C_1$-$C_3$ dialkylamino or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the process for the preparation of (S)-IB, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment of the process for the preparation of (S)-IB, R in the catalyst of formula (IIIa) is phenyl substituted by 1, 2 or 3 $C_1$-$C_6$alkoxy groups, and R' is hydrogen or methoxy. In another embodiment, R is phenyl substituted by 1, 2 or 3 methoxy, ethoxy or isopropoxy, and R' is hydrogen or methoxy, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl. In another embodiment for the preparation of (S)-IB, R in the catalyst of formula (IIIa) is phenyl independently substituted at the 3-, 4- and 5-positions with methoxy, ethoxy or isopropoxy; R' is methoxy or hydrogen; and W is vinyl or ethyl.

In yet another embodiment of the process for the preparation of (S)-IB, R in the catalyst of formula (IIIa) is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl. In another embodiment for the preparation of (S)-IB, R in the catalyst of formula (IIIa) is 3,4,5-tris(benzyloxy)phenyl; R' is methoxy or hydrogen; and W is vinyl or ethyl.

In another embodiment, the invention provides a process for the preparation of fluralaner enriched in the (S)-enantiomer:

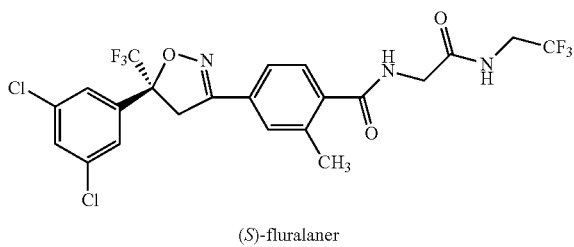 [SMILES: Cc1cc(C2=NO[C@@](c3cc(Cl)cc(Cl)c3)(C(F)(F)F)C2)ccc1C(=O)NCC(=O)NCC(F)(F)F]

(S)-fluralaner comprising reacting a compound of formula (IIB):

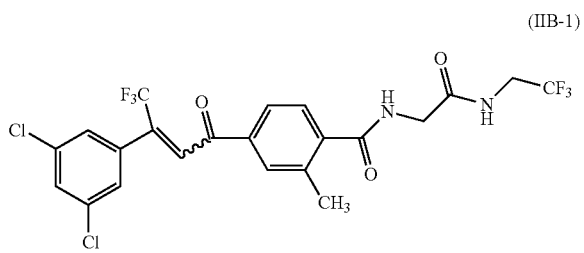 [SMILES: Cc1cc(C(=O)C=C(c2cc(Cl)cc(Cl)c2)C(F)(F)F)ccc1C(=O)NCC(=O)NCC(F)(F)F]

(IIB-1)

with hydroxylamine in the presence of water, an organic solvent that is not miscible with water, a base and a chiral phase transfer catalyst of formula (IIIa):

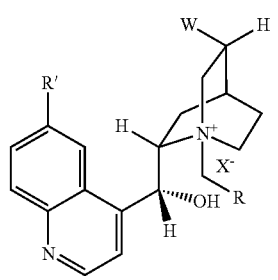

(IIIa)

wherein R is aryl or heteroaryl optionally substituted with one or more $C_1$-$C_3$alkoxy or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the synthesis of fluralaner enriched in the (S)-enantiomer, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment of the process for the preparation of fluralaner enriched in the (S)-enantiomer, R in the catalyst of formula (IIIa) is phenyl substituted by 1, 2 or 3 $C_1$-$C_6$alkoxy groups. In another embodiment, R is phenyl substituted by 1, 2 or 3 methoxy, ethoxy or isopropoxy, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy groups or isopropoxy, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl.

In another embodiment of the synthesis of fluralaner enriched in the (S)-enantiomer, R in the catalyst of formula (IIIa) is phenyl independently substituted at the 3-, 4- and 5-positions with methoxy, ethoxy or isopropoxy; R' is methoxy and W is vinyl. In another embodiment of the synthesis of fluralaner enriched in the (S)-enantiomer, R in the catalyst of formula (IIIa) is phenyl independently substituted at the 3-, 4- and 5-positions with methoxy, ethoxy or isopropoxy; R' is hydrogen and W is vinyl. In another embodiment of the synthesis of fluralaner enriched in the (S)-enantiomer, R in the catalyst of formula (IIIa) is phenyl independently substituted at the 3-, 4- and 5-positions with methoxy, ethoxy or isopropoxy; R' is methoxy and W is ethyl. In another embodiment of the synthesis of fluralaner enriched in the (S)-enantiomer, R in the catalyst of formula (IIIa) is phenyl independently substituted at the 3-, 4- and 5-positions with methoxy, ethoxy or isopropoxy; R' is hydrogen and W is ethyl.

In yet another embodiment of the synthesis of fluralaner enriched in the (S)-enantiomer, R is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl.

In another embodiment of the synthesis of fluralaner enriched in the (S)-enantiomer, R in the catalyst of formula (IIIa) is 3,4,5-tris(benzyloxy)phenyl; R' is methoxy and W is vinyl. In another embodiment of the synthesis of fluralaner enriched in the (S)-enantiomer, R in the catalyst of formula (IIIa) is 3,4,5-tris(benzyloxy)phenyl; R' is hydrogen, and W is vinyl. In another embodiment of the synthesis of fluralaner enriched in the (S)-enantiomer, R in the catalyst of formula (IIIa) is 3,4,5-tris(benzyloxy)phenyl; R' is methoxy and W is ethyl. In another embodiment of the synthesis of fluralaner enriched in the (S)-enantiomer, R in the catalyst of formula (IIIa) is 3,4,5-tris(benzyloxy)phenyl; R' is hydrogen and W is ethyl.

In another embodiment, the invention provides a process for the preparation of an isoxazoline compound of Formula IC, wherein $X^1$, $X^2$ and $X^3$ are each independently H, chloro, fluoro or $CF_3$, which is enriched in the (S)-enantiomer:

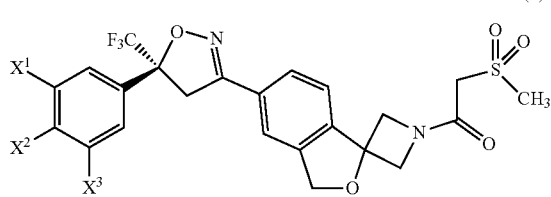

comprising reacting a compound of formula (IIC):

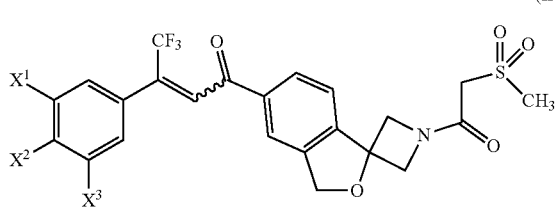

wherein $X^1$, $X^2$ and $X^3$ are H, chloro, fluoro or $CF_3$, with hydroxylamine in the presence of water, an organic solvent that is not miscible with water, a base and a chiral phase transfer catalyst of formula (IIIa):

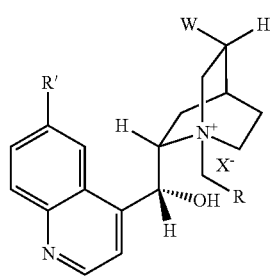

wherein R is aryl or heteroaryl optionally substituted with one or more $C_1$-$C_3$alkoxy or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the process for the preparation of (S)-IC, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment of the process for the preparation of Formula (S)-IC, R in the catalyst of formula (IIIa) is phenyl substituted by 1, 2 or 3 $C_1$-$C_6$alkoxy groups. In another embodiment, R is phenyl substituted by 1, 2 or 3 methoxy, ethoxy or isopropoxy groups, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl. In another embodiment for the preparation of (S)-IC, R in the catalyst of formula (IIIa) is phenyl independently substituted at the 3-, 4- and 5-positions with methoxy, ethoxy or isopropoxy; R' is methoxy or hydrogen; and W is vinyl or ethyl.

In yet another embodiment, R is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl. In another embodiment for the preparation of (S)-IC, R in the catalyst of formula (IIIa) is 3,4,5-tris(benzyloxy)phenyl; R' is methoxy or hydrogen; and W is vinyl or ethyl.

In another embodiment, the invention provides a process for the preparation of sarolaner:

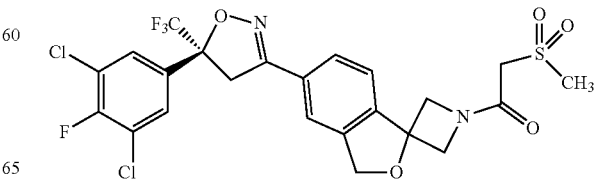

comprising reacting a compound of formula (IIC-1):

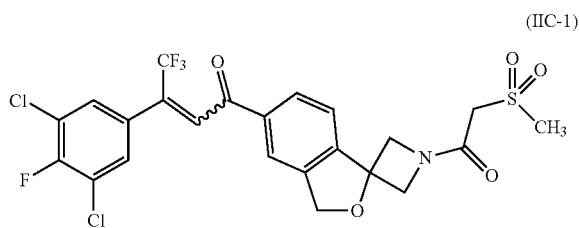

(IIC-1)

with hydroxylamine in the presence of water, a base and a chiral phase transfer catalyst of formula (IIIa):

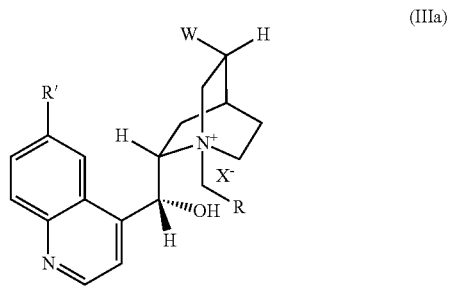

(IIIa)

wherein R is aryl or heteroaryl optionally substituted with one or more $C_1$-$C_3$alkoxy or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the synthesis of sarolaner, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment, R is phenyl substituted by 1, 2 or 3 $C_1$-$C_6$alkoxy groups, and R' is hydrogen or methoxy. In another embodiment, R is phenyl substituted by 1, 2 or 3 methoxy, ethoxy or isopropoxy groups, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl.

In another embodiment of the synthesis of sarolaner, R in the catalyst of formula (IIIa) is phenyl independently substituted at the 3-, 4- and 5-positions with methoxy, ethoxy or isopropoxy or isopropoxy; R' is methoxy and W is vinyl. In another embodiment of the synthesis of sarolaner, R in the catalyst of formula (IIIa) is phenyl independently substituted at the 3-, 4- and 5-positions with methoxy, ethoxy or isopropoxy; R' is hydrogen and W is vinyl. In another embodiment of the synthesis of sarolaner, R in the catalyst of formula (IIIa) is phenyl independently substituted at the 3-, 4- and 5-positions with methoxy, ethoxy or isopropoxy; R' is methoxy and W is ethyl. In another embodiment of the synthesis of sarolaner, R in the catalyst of formula (IIIa) is phenyl independently substituted at the 3-, 4- and 5-positions with methoxy, ethoxy or isopropoxy; R' is hydrogen and W is ethyl.

In yet another embodiment in the synthesis of sarolaner, R in the catalyst of formula (IIIa) is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl.

In another embodiment of the synthesis of sarolaner, R in the catalyst of formula (IIIa) is 3,4,5-tris(benzyloxy)phenyl; R' is methoxy and W is vinyl. In another embodiment of the synthesis of sarolaner, R in the catalyst of formula (IIIa) is 3,4,5-tris(benzyloxy)phenyl; R' is hydrogen, and W is vinyl. In another embodiment of the synthesis of sarolaner, R in the catalyst of formula (IIIa) is 3,4,5-tris(benzyloxy)phenyl; R' is methoxy and W is ethyl. In another embodiment of the synthesis of sarolaner, R in the catalyst of formula (IIIa) is 3,4,5-tris(benzyloxy)phenyl; R' is hydrogen and W is ethyl.

In another embodiment, the invention provides a process for the preparation of an isoxazoline compound of Formula ID, wherein $X^1$, $X^2$ and $X^3$ are each independently H, chloro, fluoro or $CF_3$, which is enriched in the (S)-enantiomer:

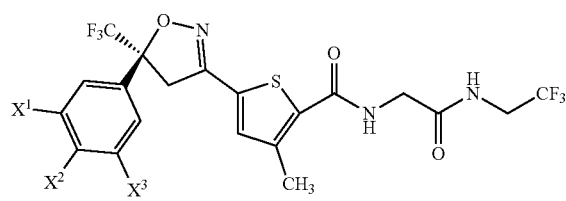

(S)-ID comprising reacting a compound of formula (IID):

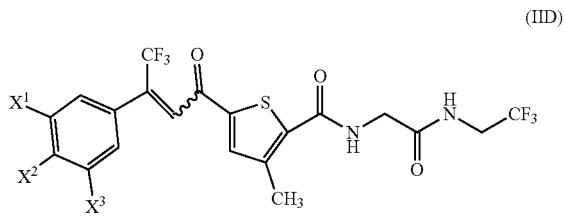

(IID)

wherein $X^1$, $X^2$ and $X^3$ are H, chloro, fluoro or $CF_3$, with hydroxylamine in the presence of water, an organic solvent that is not miscible with water, a base and a chiral phase transfer catalyst of formula (IIIa):

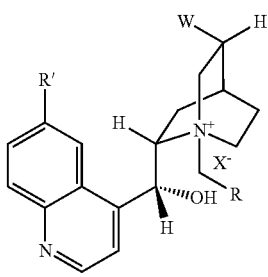

(IIIa)

wherein R is aryl or heteroaryl optionally substituted with one or more $C_1$-$C_3$alkoxy or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the process for the preparation of (S)-ID, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment, R is phenyl substituted by 1, 2 or 3 $C_1$-$C_6$alkoxy groups, and R' is hydrogen or methoxy. In another embodiment, R is phenyl substituted by 1, 2 or 3 methoxy, ethoxy or isopropoxy groups, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl. In another embodiment for the preparation of (S)-ID, R in the catalyst of formula (IIIa) is phenyl independently substituted at the 3-, 4- and 5-positions with methoxy, ethoxy or isopropoxy; R' is methoxy or hydrogen; and W is vinyl or ethyl.

In yet another embodiment of the process for the preparation of Formula ID enriched in the (S)-enantiomer, R in the catalyst of formula (IIIa) is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl. In another embodiment for the preparation of (S)-ID, R in the catalyst of formula (IIIa) is 3,4,5-tris(benzyloxy)phenyl; R' is methoxy or hydrogen; and W is vinyl or ethyl.

In another embodiment, the invention provides a process for the preparation of lotilaner:

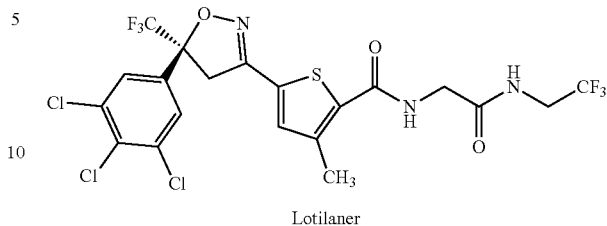

Lotilaner comprising reacting a compound of formula (IID-1):

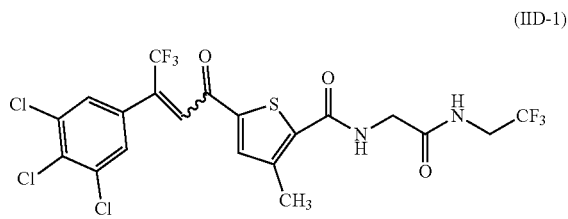 [SMILES: Cc1cc(C(=O)C=C(c2cc(Cl)c(Cl)c(Cl)c2)C(F)(F)F)sc1C(=O)NCC(=O)NCC(F)(F)F]

with hydroxylamine in the presence of water, an organic solvent that is not miscible with water, a base and a chiral phase transfer catalyst of formula (IIIa):

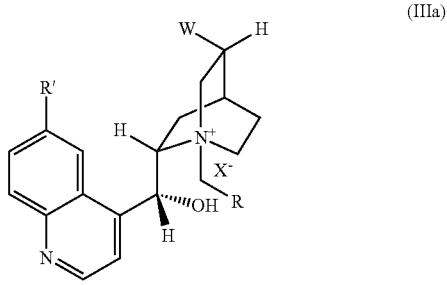

wherein R is aryl or heteroaryl optionally substituted with one or more $C_1$-$C_3$alkoxy or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the process for the preparation of lotilaner, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment of the process for the preparation of lotilaner, R in the catalyst of formula (IIIa) is phenyl substituted by 1, 2 or 3 $C_1$-$C_6$alkoxy groups, and R' is hydrogen or methoxy. In another embodiment, R is phenyl substituted by 1, 2 or 3 methoxy, ethoxy or isopropoxy groups, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl.

In another embodiment of the synthesis of lotilaner, R in the catalyst of formula (IIIa) is phenyl independently substituted at the 3-, 4- and 5-positions with methoxy, ethoxy or isopropoxy; R' is methoxy and W is vinyl. In another embodiment of the synthesis of lotilaner, R in the catalyst of formula (IIIa) is phenyl independently substituted at the 3-, 4- and 5-positions with methoxy, ethoxy or isopropoxy; R' is hydrogen and W is vinyl. In another embodiment of the synthesis of lotilaner, R in the catalyst of formula (IIIa) is phenyl independently substituted at the 3-, 4- and 5-positions with methoxy, ethoxy or isopropoxy; R' is methoxy and W is ethyl. In another embodiment of the synthesis of lotilaner, R in the catalyst of formula (IIIa) is phenyl independently substituted at the 3-, 4- and 5-positions with methoxy, ethoxy or isopropoxy; R' is hydrogen and W is ethyl.

In yet another embodiment of the process for the preparation of lotilaner, R in the catalyst of formula (IIIa) is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl.

In another embodiment of the synthesis of lotilaner, R in the catalyst of formula (IIIa) is 3,4,5-tris(benzyloxy)phenyl; R' is methoxy and W is vinyl. In another embodiment of the synthesis of lotilaner, R in the catalyst of formula (IIIa) is 3,4,5-tris(benzyloxy)phenyl; R' is hydrogen, and W is vinyl. In another embodiment of the synthesis of lotilaner, R in the catalyst of formula (IIIa) is 3,4,5-tris(benzyloxy)phenyl; R' is methoxy and W is ethyl. In another embodiment of the synthesis of lotilaner, R in the catalyst of formula (IIIa) is 3,4,5-tris(benzyloxy)phenyl; R' is hydrogen and W is ethyl. In another embodiment, the invention provides a process for the preparation of an isoxazoline compound of Formula IE, wherein $X^1$, $X^2$ and $X^3$ are each independently H, chloro, fluoro or $CF_3$, which is enriched in the (S)-enantiomer:

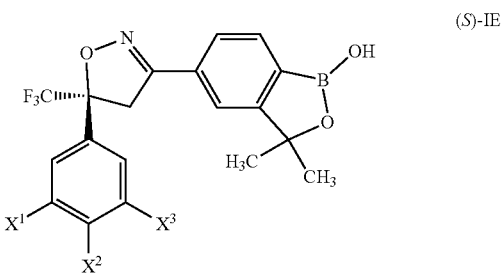

(S)-IE comprising reacting a compound of formula (IIA):

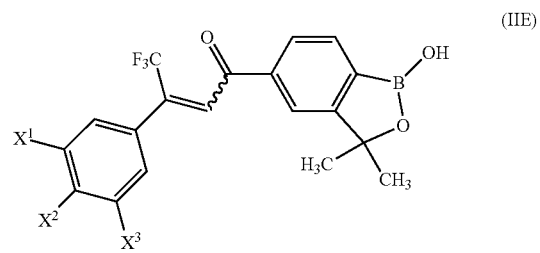

(IIE)

wherein $X^1$, $X^2$ and $X^3$ are H, chloro, fluoro or $CF_3$, with hydroxylamine in the presence of water, an organic solvent that is not miscible with water, a base and a chiral phase transfer catalyst of formula (IIIa):

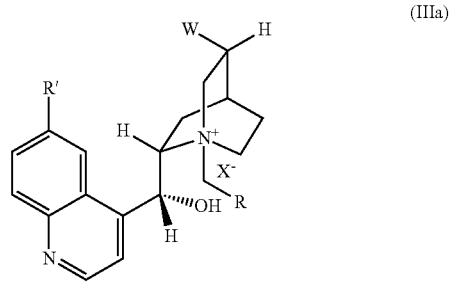

(IIIa)

wherein R is aryl or heteroaryl optionally substituted with one or more $C_1$-$C_3$alkoxy or aralkoxy groups, R' is hydrogen or $C_1$-$C_3$alkoxy, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the process for the preparation of (S)-IE, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment of the process for the preparation of Formula IE enriched in the (S)-enantiomer, R in the catalyst of formula (IIIa) is phenyl substituted by 1, 2 or 3 $C_1$-$C_6$alkoxy groups, and R' is hydrogen or methoxy. In another embodiment, R is phenyl substituted by 1, 2 or 3 methoxy, ethoxy or isopropoxy groups, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl. In another embodiment for the preparation of (S)-IE, R in the catalyst of formula (IIIa) is phenyl independently substituted at the 3-, 4- and 5-positions with methoxy, ethoxy or isopropoxy; R' is methoxy or hydrogen; and W is vinyl or ethyl.

In yet another embodiment of the process for the preparation of Formula IE enriched in the (S)-enantiomer, R in the catalyst of formula (IIIa) is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl. In another embodiment for the preparation of (S)-IE, R in the catalyst of formula (IIIa) is 3,4,5-tris(benzyloxy)phenyl; R' is methoxy or hydrogen; and W is vinyl or ethyl.

In another embodiment, the invention provides a process for the preparation of an isoxazoline compound of Formula IE-1, which is enriched in the (S)-enantiomer:

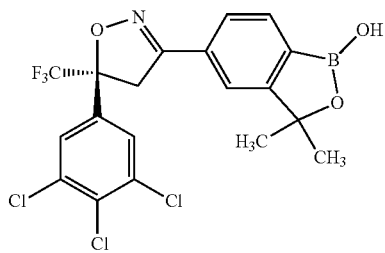
(S)-IE-1 comprising reacting a compound of formula (IIA):

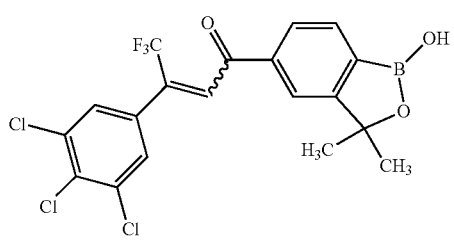
(IIE-1)

with hydroxylamine in the presence of water, an organic solvent that is not miscible with water, a base and a chiral phase transfer catalyst of formula (IIIa):

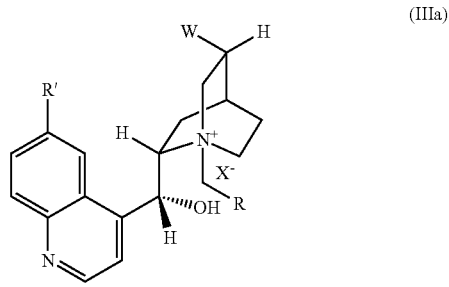
(IIIa)

wherein R is aryl or heteroaryl optionally substituted with one or more $C_1$-$C_3$alkoxy or aralkoxy groups, W is ethyl or vinyl and $X^-$ is an anion; and isolating the product. In a preferred embodiment, the product is isolated by crystallization. In another preferred embodiment, the product is isolated by crystallization from an aromatic solvent or a solvent mixture comprising an aromatic solvent. In one embodiment, the product is crystallized from toluene, ethylbenzene, xylenes, chlorobenzene, o-dichlorobenzene, fluorobenzene, anisole or mesitylene, or a mixture thereof, or a solvent mixture comprising one of these solvents. In a preferred embodiment, the product is crystallized from toluene or a solvent mixture comprising toluene.

In one embodiment of the process for the preparation of (S)-IE-1, R in the catalyst of formula (IIIa) is aryl or heteroaryl substituted by one or more $C_1$-$C_6$alkoxy. In another embodiment, R is aryl or heteroaryl substituted by one or more methoxy, ethoxy, n-propoxy, isopropoxy, n-butoxy, isobutoxy, sec-butoxy or tert-butoxy. In another embodiment, R is aryl or heteroaryl substituted by one or more benzyloxy.

In another embodiment, R is phenyl substituted by 1, 2 or 3 $C_1$-$C_6$alkoxy groups, and R' is hydrogen or methoxy. In another embodiment, R is phenyl substituted by 1, 2 or 3 methoxy, ethoxy or isopropoxy groups, and R' is hydrogen or methoxy. In another embodiment, R is phenyl substituted by 1, 2 or 3 methoxy, ethoxy or isopropoxy groups, R' is methoxy and W is vinyl. I still another embodiment, R is phenyl substituted by 1, 2 or 3 methoxy, ethoxy or isopropoxy groups, R' is hydrogen, and W is vinyl. In another embodiment, R is phenyl substituted by 1, 2 or 3 methoxy, ethoxy or isopropoxy groups, R' is methoxy and W is ethyl. In still another embodiment, R is phenyl substituted by 1, 2 or 3 methoxy, ethoxy or isopropoxy groups, R' is hydrogen and W is ethyl.

In another embodiment of the synthesis of Formula IE-1 enriched in the (S)-enantiomer, R in the catalyst of formula (IIIa) is phenyl independently substituted at the 3-, 4- and 5-positions with methoxy, ethoxy or isopropoxy; R' is methoxy and W is vinyl. In another embodiment of the synthesis of Formula IE-1 enriched in the (S)-enantiomer, R in the catalyst of formula (IIIa) is phenyl independently substituted at the 3-, 4- and 5-positions with methoxy, ethoxy or isopropoxy; R' is hydrogen and W is vinyl. In another embodiment of the synthesis of Formula IE-1 enriched in the (S)-enantiomer, R in the catalyst of formula (IIIa) is phenyl independently substituted at the 3-, 4- and 5-positions with methoxy, ethoxy or isopropoxy; R' is methoxy and W is ethyl. In another embodiment of the synthesis of Formula IE-1 enriched in the (S)-enantiomer, R in the catalyst of formula (IIIa) is phenyl independently substituted at the 3-, 4- and 5-positions with methoxy, ethoxy or isopropoxy; R' is hydrogen and W is ethyl.

In yet another embodiment, R is phenyl substituted by 1, 2 or 3 benzyloxy, and R' is hydrogen or methoxy. In another embodiment, R is phenyl substituted by 1, 2 or 3 benzyloxy groups, R' is methoxy and W is vinyl. I still another embodiment, R is phenyl substituted by 1, 2 or 3 benzyloxy, R' is hydrogen, and W is vinyl. In another embodiment, R is phenyl substituted by 1, 2 or 3 benzyloxy groups, R' is methoxy and W is ethyl. In still another embodiment, R is phenyl substituted by 1, 2 or 3 benzyloxy groups, R' is hydrogen and W is ethyl.

In another embodiment of the synthesis of Formula IE-1 enriched in the (S)-enantiomer, R in the catalyst of formula (IIIa) is 3,4,5-tris(benzyloxy)phenyl; R' is methoxy and W is vinyl. In another embodiment of the synthesis of Formula IE-1 enriched in the (S)-enantiomer, R in the catalyst of formula (IIIa) is 3,4,5-tris(benzyloxy)phenyl;

R' is hydrogen, and W is vinyl. In another embodiment of the synthesis of Formula IE-1 enriched in the (S)-enantiomer, R in the catalyst of formula (IIIa) is 3,4,5-tris(benzyloxy)phenyl; R' is methoxy and W is ethyl. In another embodiment of the synthesis of Formula IE-1 enriched in the (S)-enantiomer, R in the catalyst of formula (IIIa) is 3,4,5-tris(benzyloxy)phenyl; R' is hydrogen and W is ethyl.

In any of the embodiments of the invention described above, the chiral phase transfer catalyst of formula (IIIa) may have the structures of formulae (IIIa-1) to (IIIa-38) in Table 1 below, wherein W is ethyl or vinyl, $X^-$ is a halogen, mesylate, tosylate, triflate, brosylate, nosylate or tresylate counter ion; each R is independently methyl, ethyl, n-propyl, isopropyl, n-butyl, sec-butyl, iso-butyl, tert-butyl or $CH_2Ph$; R' is hydrogen or $C_1$-$C_3$-alkoxy; Z is halogen, $C_1$-$C_3$alkyl or $C_1$-$C_3$haloalkyl; n is 0, 1, 2, 3 or 4; m is 1 or 2; p is 1 or 2; and $R^1$, $R^2$, $R^3$ and $R^4$ are independently H or $C_1$-$C_3$alkyl.

TABLE 1

Chiral phase transfer catalysts of formula (IIIa-1) to (IIIa-38)

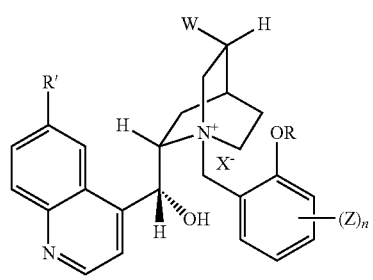
(IIIa-1)

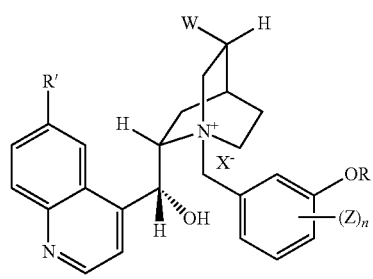
(IIIa-2)

TABLE 1-continued

Chiral phase transfer catalysts of formula (IIIa-1) to (IIIa-38)

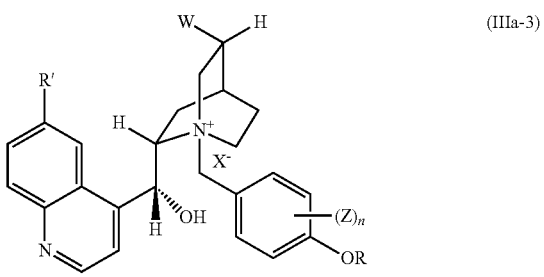
(IIIa-3)

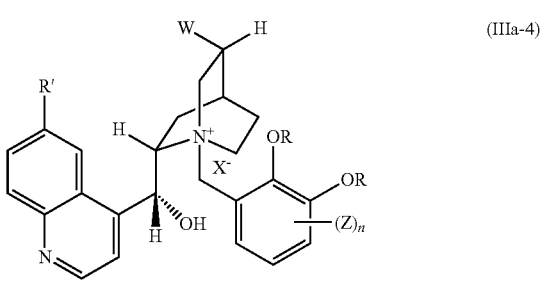
(IIIa-4)

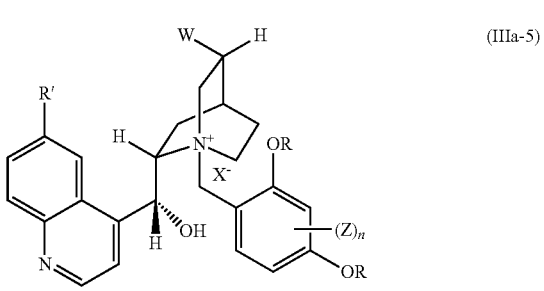
(IIIa-5)

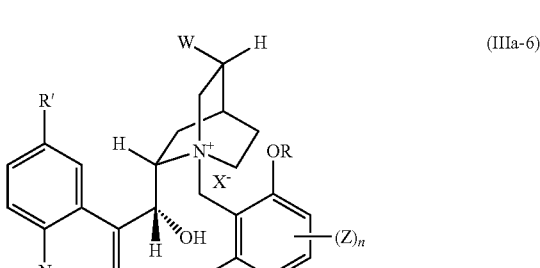
(IIIa-6)

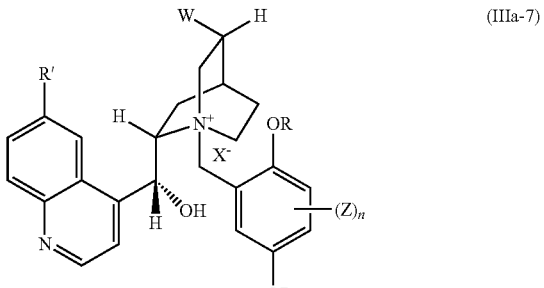
(IIIa-7)

TABLE 1-continued
Chiral phase transfer catalysts of formula (IIIa-1) to (IIIa-38)
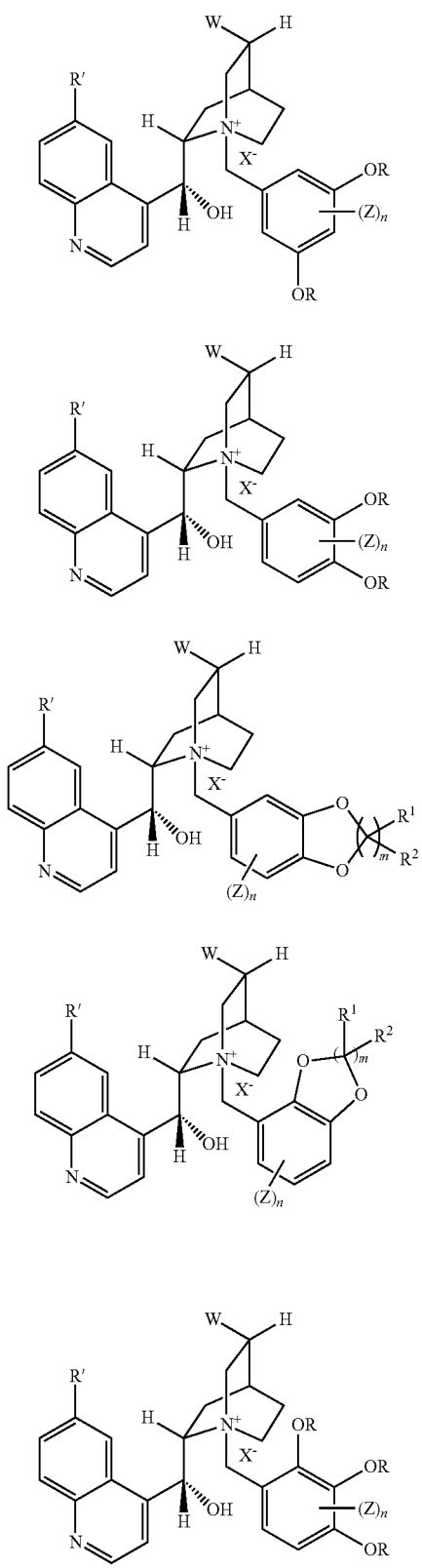
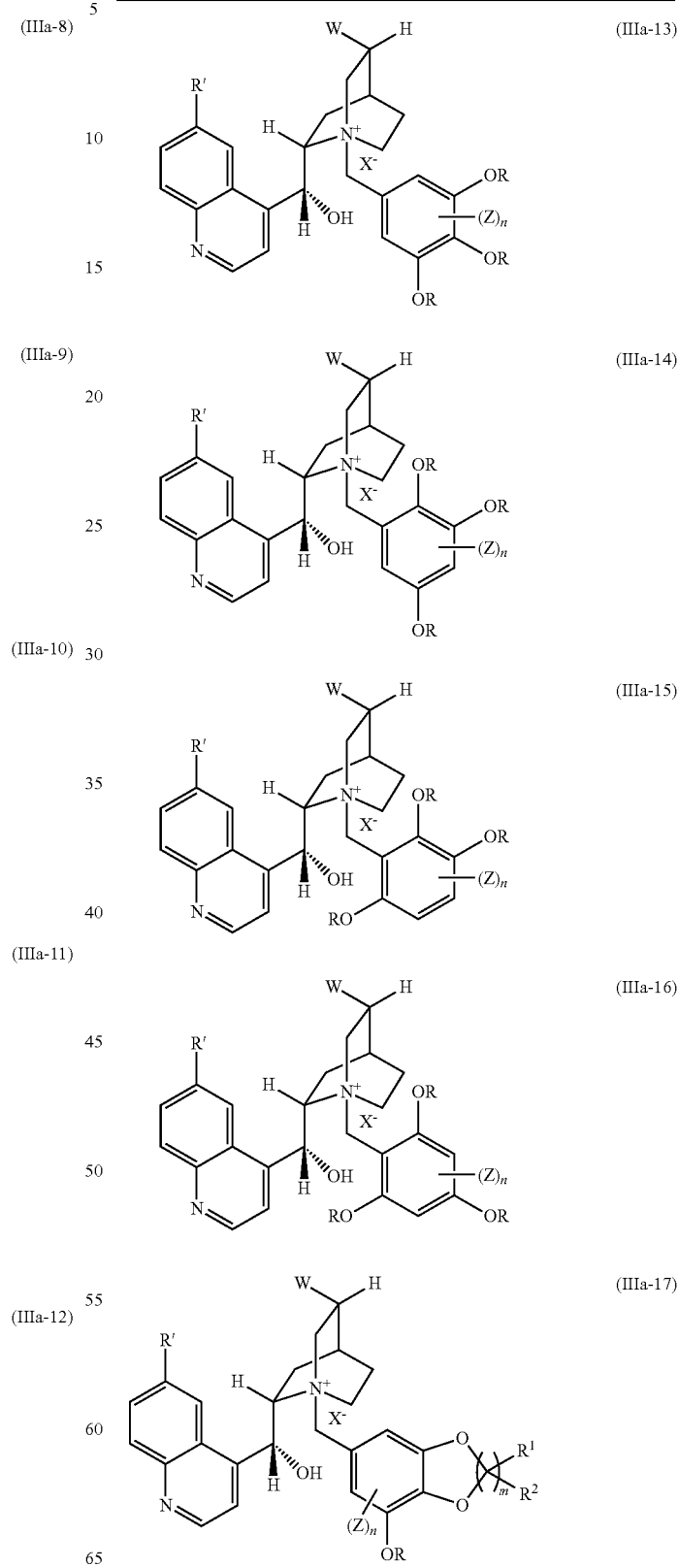

TABLE 1-continued
Chiral phase transfer catalysts of formula (IIIa-1) to (IIIa-38)
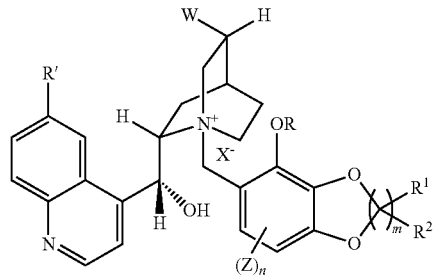 (IIIa-18)
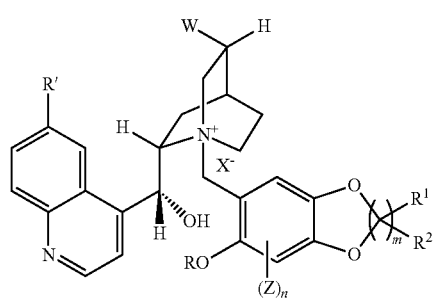 (IIIa-19)
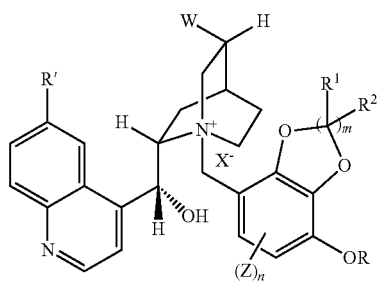 (IIIa-20)
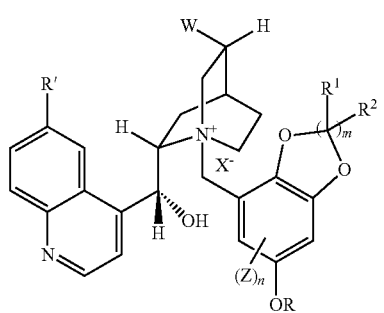 (IIIa-21)
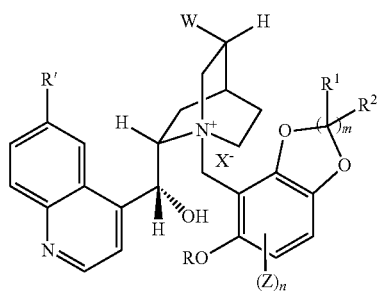 (IIIa-22)
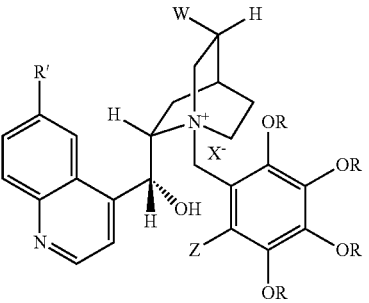 (IIIa-23)
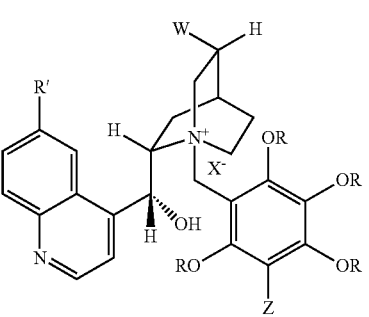 (IIIa-24)
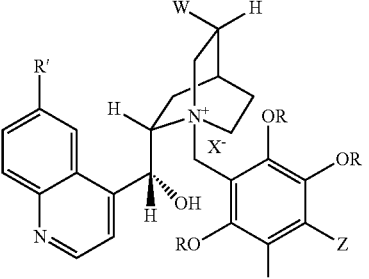 (IIIa-25)
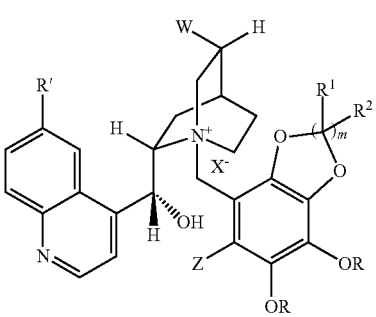 (IIIa-26)
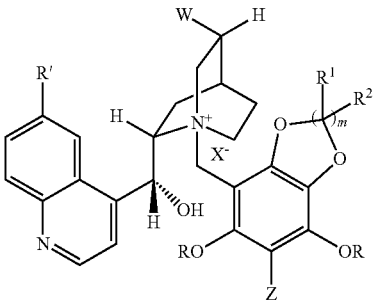 (IIIa-27)

TABLE 1-continued
Chiral phase transfer catalysts of formula (IIIa-1) to (IIIa-38)
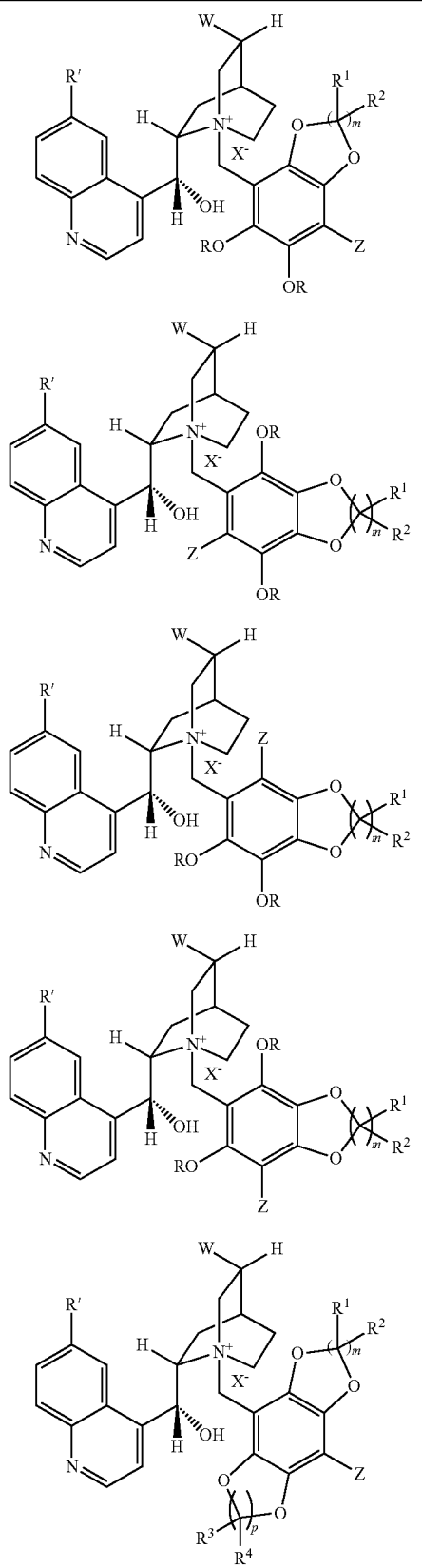
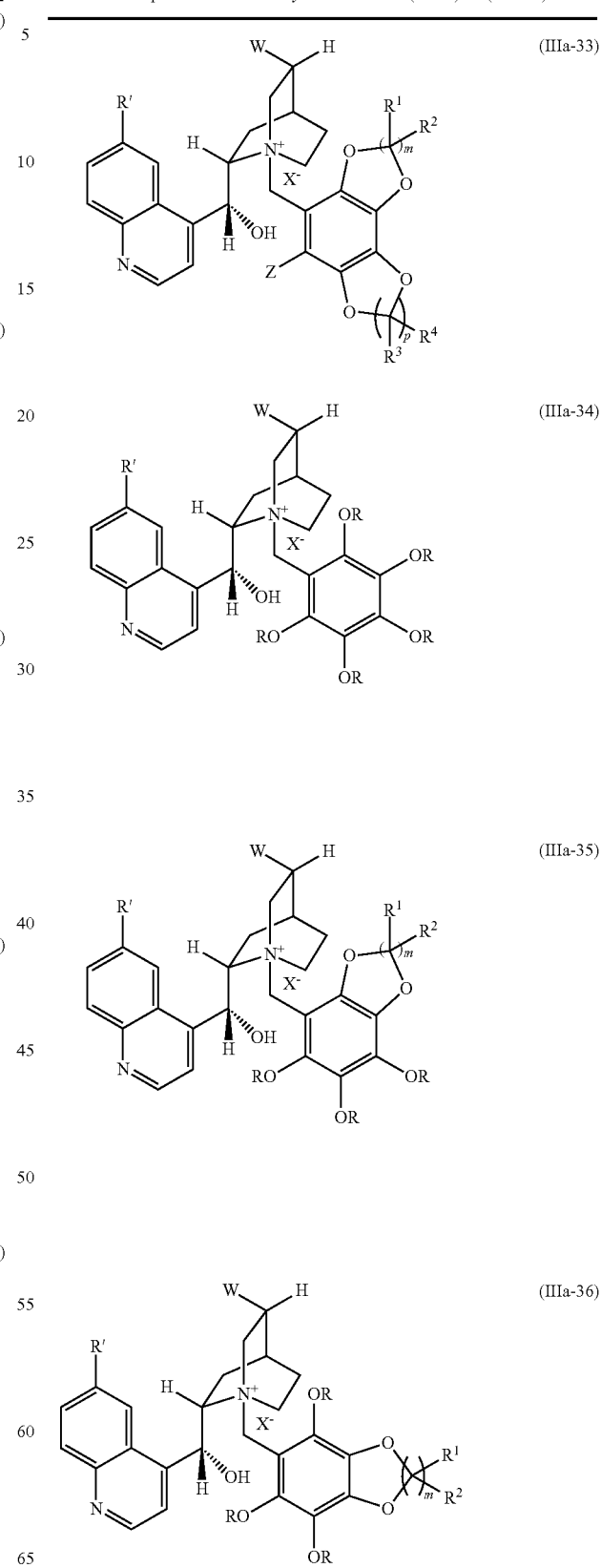

TABLE 1-continued

Chiral phase transfer catalysts of formula (IIIa-1) to (IIIa-38)

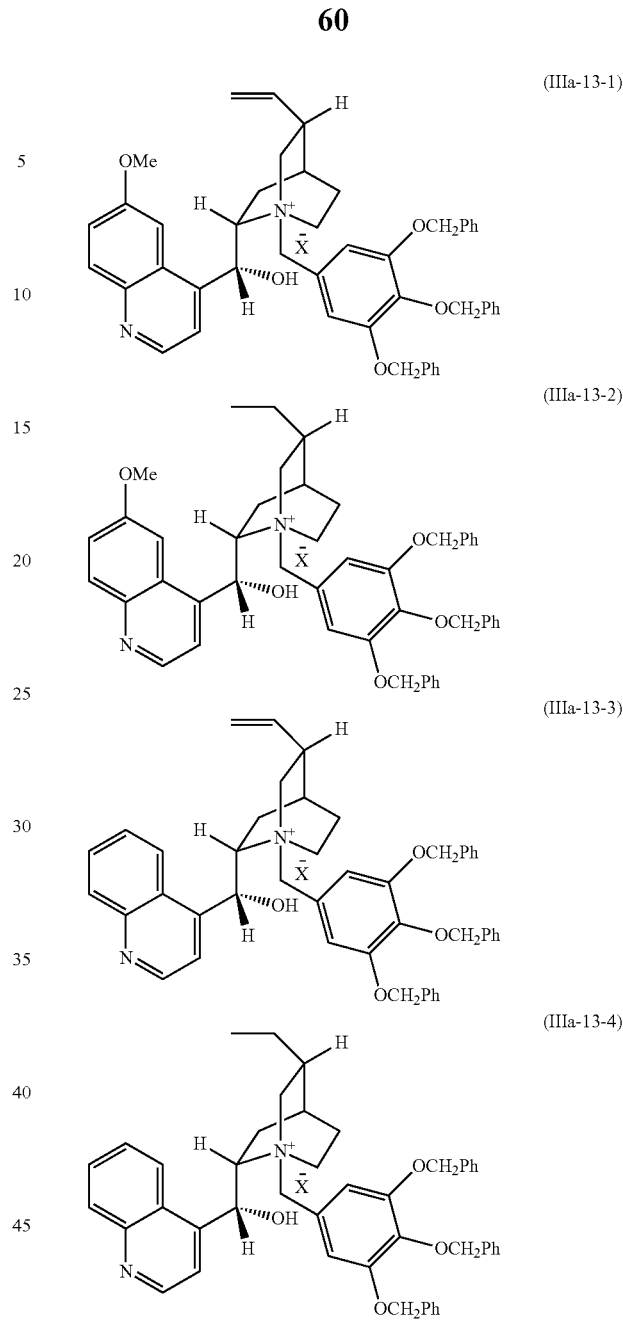

In another embodiment, the invention provides chiral phase transfer catalysts of formula (IIIb-1) to (IIIb-38) wherein the compounds have the structures shown in Table 1 above, with the exception that the compounds have the opposite stereochemistry shown at the carbon atom bearing the hydroxy group and the carbon atom adjacent to the nitrogen atom of the quinuclidine core.

In another embodiment, the invention provides chiral phase transfer catalysts of formula (IIIa-39) to (IIIa-76), wherein the chiral phase transfer catalysts have the formulas of compounds of formula (IIIa-1) to (IIIa-38), except that the groups OR are replaced with the groups —NHR where R has the same meaning.

In another embodiment, the invention provides chiral phase transfer catalysts of formula (IIIa-77) to (IIIa-114), wherein the chiral phase transfer catalysts have the formulas of compounds of formula (IIIa-1) to (IIIa-38), except that the groups OR are replaced with the groups —NR$^a$R$^b$ where R$^a$ and R$^b$ have the same meaning as R in Table 1.

In one embodiment, the invention provides a chiral phase transfer catalyst of the formula (IIIa-13-1), (IIIa-13-2), (IIIa-13-3) or (IIIa-13-4), or a mixture thereof, wherein X$^-$ is a counter ion, or a mixture of two or more of the catalysts:

In another embodiment, the invention provides a chiral phase transfer catalyst of formula (IIIa-13-1), (IIIa-13-2), (IIIa-13-3) or (IIIa-13-4) wherein X$^-$ is a halogen counter ion. In another embodiment, X$^-$ is a chloride counter ion. In yet another embodiment, X$^-$ is a mesylate, tosylate, triflate, brosylate, nosylate or tresylate counter ion. The novel phase transfer catalyst may be used to prepare enantiomerically-enriched antiparasitic isoxazolines as described herein; however, the skilled person will also understand that this catalyst may be used to catalyze other phase transfer reactions to prepare enantiomerically enriched compounds.

Synthesis of Chiral Phase Transfer Catalysts

The chiral phase transfer catalysts of the invention may be prepared by reacting suitably substituted arylmethyl or heteroarylmethyl intermediates having a suitable leaving group on the methyl moiety with quinine or dihydroquinine in a solvent. Representative examples of the reaction to prepare other quinine-based chiral phase transfer catalysts may be found in, for example, US 2014/0206633 A1, US 2014/0350261 A1, both incorporated herein by reference. Additional examples of the preparation and use of quinine-based chiral phase transfer catalysts are found in *Angew. Chem. Int. Ed.* 2007, 46, 4222-4266; *Tetrahedron Letters* 1998, 8775; and *Chem. Commun.* 2009, 7090. For example, chloromethyl-substituted aryl or heteroaryl intermediates may be reacted with quinine to yield the desired catalysts. Scheme 1 below provides an example of the preparation of chiral phase transfer catalysts based on quinine that may be used in the process of the invention, wherein R is $C_1$-$C_3$alkyl or aralkyl and LG is a suitable leaving group such as halogen (e.g. chloride, iodide, etc.), mesylate, tosylate, triflate and the like.

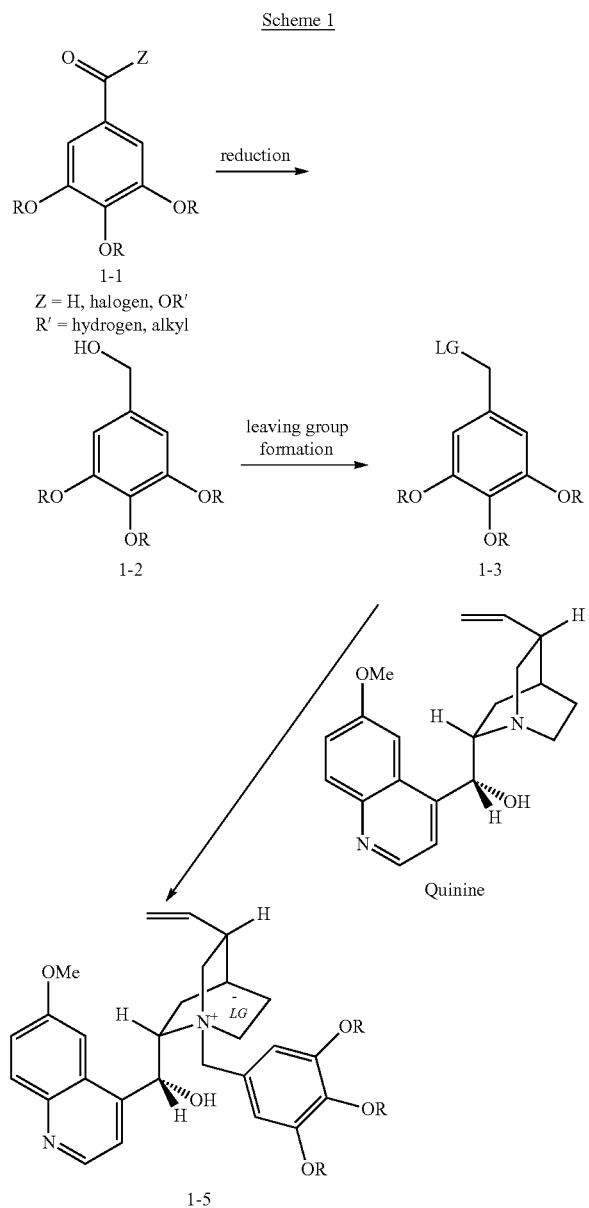

Scheme 1

LG = leaving group such as halogen, mesylate, tosylate, triflate, etc.
R = $C_1$-$C_3$alkyl or aralkyl It will be appreciated by skilled persons in the art that other phase transfer catalysts may be prepared by, for example, reacting other cinchona alkaloids with the intermediate 1-3. Other cinchona alkaloids that may be used include cinchonidine, cinchonine and quinidine. Similarly, dihydroquinine, dihydrocinchonidine, dihydrocinchonine and dihydroquinidine may be reacted with intermediate 1-3 to produce the corresponding chiral phase transfer catalyst 1-5.

Furthermore, skilled persons in the art will understand that reduction of intermediate 1-1 to alcohol 1-2 may be achieved with a variety of suitable reducing agents and reduction conditions known in the art, as this is a very general reaction in organic chemistry. For example, the reduction of 1-1 may be conducted by a variety of reducing agents such as sodium borohydride ($NaBH_4$), sodium triacetoxy borohydride, sodium bis(2-methoxyethoxy)aluminum hydride (Red-Al), lithium aluminum hydride ($LiAlH_4$), and the like. Further, the reduction may be advantageously conducted using a combination of a reducing agent with a Lewis Acid such as $NaBH_4/AlCl_3$, and others (see, for example, Advanced Organic Chemistry, Reactions, Mechanisms and Structure, $3^{rd}$ edition, by Jerry March, John Wiley & Sons, New York, 1985 ("March").

Furthermore, it will be appreciated that the halogenation of alcohols is also a very well-known transformation in organic chemistry (e.g. thionyl chloride ($SOCl_2$), see March) and various reagents and conditions are well known to the skilled person. The reaction of quinine with a halomethyl-substituted aromatic group is achieved by heating the reactants in an inert organic solvent such as toluene at elevated temperatures (see for example US 2014/0206633 A1, US 2014/0350261 A1).

It will also be appreciated by skilled persons in the art that quinine may be reacted with suitably substituted aryl or heteroaryl groups containing other leaving groups on the arylmethyl or heteroarylmethyl group. This includes, for example, tosylates, mesylates, triflates, and the like.

The preparation of compounds of formula (II) is known in the art. For example, in U.S. Pat. Nos. 8,217,180; 8,952,175 and publication nos. US 2014/0206633 and WO 2014/081800 (all incorporated herein by reference), among others, provide methods for the synthesis of these compounds. Furthermore, skilled persons based on the methods taught in these and other publications in combination with the state of the art will be readily able to make further compounds of formula (II) with different substitution patterns.

Preparation of Chiral Isoxazoline Compounds

The preparation of isoxazoline active agents of formula (I) by the reaction of compounds of formula (II) with hydroxylamine and a base in the presence of a chiral phase transfer catalyst of formula (IIIa) or (IIIb) may be conducted in a biphasic mixture of water and a suitable inert organic solvent that is not miscible with water. In some embodiments where the compound of formula (II) forms an immiscible liquid phase with water an organic solvent may not be necessary. In certain other embodiments wherein the reaction may work in a single phase, the reaction may be carried out without water or with a minor amount of water. Preferably, the process is conducted in a biphasic mixture of water an organic solvent that is not miscible with water.

Suitable organic solvents include, but are not limited to, aromatic solvents, aliphatic solvents and halogenated aliphatic solvents, ether solvents, and the like. Preferred solvents will not be miscible with water and will have low solubility in water. In one embodiment, an aromatic solvent will be used in the process of the invention including, but not limited to, toluene, xylenes, fluorobenzene, chlorobenzene, o-dichlorobenzene, anisole and mesitylene. In one preferred embodiment, aliphatic solvents optionally substituted with halogen may be used for the reaction of the compound of formula (II) with hydroxylamine in the presence of a chiral phase transfer catalyst of formula (IIIa) or (IIIb). Aliphatic solvents, optionally substituted with halogen, include, but are not limited to, n-pentane, n-hexane, n-heptane, n-octane, cyclopentane, cyclohexane, dichloromethane, chloroform, and 1,2-dichloroethane and methylcyclohexane. In a preferred embodiment, the reaction of a compound of formula (II) with hydroxyl amine in the presence of a chiral phase transfer catalyst is conducted in a halogenated aliphatic solvent such as dichloromethane or an aromatic solvent such as toluene.

In some embodiments, ether solvents may be used in the process of the to prepare the enantiomerically-enriched isoxazoline compounds including, but not limited to, diethyl ether, diisopropyl ether, di-n-butyl ether, cyclopentyl methyl ether, t-butyl methyl ether and t-butyl ethyl ether. In some embodiments, tetrahydrofuran, dimethoxyethane, dioxane, tetrahydropyran, methyltetrahydrofuran including 2-methyltetrahydrofuran, diethoxymethane, acetonitrile, or a combination thereof may be used. In various embodiments, a combination of solvents described above may be used.

The amount of the organic solvent used in the reaction is not critical and depends on the available equipment used for the process as long as the amount of solvent is sufficient to provide the desired reaction at a reasonable rate. However, it will be appreciated that using smaller volumes of an organic solvent will be beneficial from an economic and environmental point of view. In some embodiments of the invention, the reaction of a compound of formula (II) with a chiral phase transfer catalyst of formula (IIIa) or (IIIb) may use a volume of an organic solvent of between about 1 to about 100 volumes based on the amount of the starting amount of the compound of formula (II) assuming a density of 1 g/mL (excluding water in the reaction medium). For example, if 100 g of the compound of formula (II) is used in the reaction, 10 volumes of solvent would equal 1000 mL. In other embodiments, the reaction may be carried out with between about 1 to about 80 volumes of solvent. In another embodiment, the reaction may be carried out with between about 1 to about 50 volumes of solvent. In yet another embodiment, the reaction may be carried out with between about 1 to about 30 volumes of solvent or between about 1 to about 20 volumes of solvent. In another embodiment, the reaction may be carried out with about 1 to about 15 or about 5 to about 15 volumes of solvent. In another embodiment, the reaction of the compound of formula (II) with hydroxylamine in the presence of a base and a chiral phase transfer catalyst of formula (IIIa) or (IIIb) to form the compound of formula (I) will use about 10 volumes of solvent.

The reaction may be carried out at temperatures of between about −78° C. to about 60° C. depending on the solvents used and other factors. More typically, the reaction to form the isoxazoline compounds of formula (I) is carried out at a temperature of between about −30° C. to about 40° C. In one embodiment, the reaction is carried out between about −20° C. to about 25° C. In another embodiment, the reaction is carried out at a temperature of about −15° C. to about 20° C. In yet another embodiment, the reaction is carried out at a temperature of about −15° C. to about 10° C. or about −15° C. to about 5° C. In another embodiment, the reaction may be carried out at a temperature range of about −15° C. to about −5° C. In another embodiment, the reaction is carried at a temperature of about −15° C. to about 0° C. or about −10° to about 0° C. In yet another embodiment, the reaction is carried out at a temperature of about −13° C. to about 3° C.

Of course, the reaction may take a shorter or longer time depending on the temperature and concentration of the reaction mixture. The extent of the reaction may be monitored by measuring the amount of starting material remaining (e.g. compound of formula (II)) using chromatographic methods such as thin layer chromatography (tlc) or HPLC, and the reaction may be stopped when a suitable conversion is reached. In some embodiments, the reaction will be conducted from about 30 minutes to about 48 hours. In one embodiment, the reaction will be aged for about 1 hour to about 48 hours or about 1 hour to about 24 hours. In other embodiments, the reaction will be aged about 1 hour to about 10 hours. In some embodiments, the reaction is aged for about 1 hour to about 5 hours. In another embodiment, the reaction is aged about 10 to about 30 hours. In another embodiment, the reaction is aged about 15 hours to about 25 hours to obtain the desired reaction conversion.

In some embodiments of the invention, hydroxylamine may be used in excess relative to the compound of formula (II) including between about 1 and about 50 molar equivalents (as a free base). In one embodiment, the amount of hydroxylamine may be between about 1 to about 20 equivalents. In another embodiment, an amount of about 1 to about 15 equivalents of hydroxylamine may be used. In another embodiment, between about 1 to about 10 equivalents of hydroxylamine may be used. In another embodiment, between about 1 to about 5 equivalents or between about 1 to about 6 equivalents of hydroxylamine may be used. In other embodiments, between about 4 to about 8 equivalents of hydroxylamine may be used. In yet another embodiment, between about 5 to about 7 equivalents of hydroxylamine may be used. In another embodiment, about 5 or about 6 equivalents of hydroxylamine may be used. In another embodiment, between about 1 to about 3 molar equivalents of hydroxylamine may be used. In yet another embodiment, between about 1.5 to about 3 or about between about 1.5 to about 2.5 molar equivalents of hydroxylamine per mole of the compound of formula (II) may be used. In a particular embodiment, about 2.2 molar equivalents of hydroxylamine (as free base) per mole of the compound of formula (II) will be used.

The hydroxylamine may be as the free base or may be used as an acid salt such as the hydroxylamine sulfate salt, the hydrochloride salt, phosphate, oxalate, nitrate or acetate. However, because hydroxylamine is hazardous as a free base, it may be beneficial to store and use it as a salt and produce the free base in situ by the addition of a base. Nevertheless, the molar equivalents of hydroxylamine relative to the compound of formula (II) will be calculated as a free base.

In some embodiments, the hydroxylamine reactant will be used as a water solution. The concentration of the hydroxylamine water solution (either as a free base or as a salt) is not limited. However, for safety lower concentrations may be desired including about 50% (w/w) or lower. In some embodiments, the process of the invention will use an aqueous solution of hydroxylamine of between 5 to about 50% (w/w). In another embodiment, the concentration of hydroxylamine used will be between about 10 to about 30% (w/w) or about 15 to about 25% (w/w). In another embodiment, the concentration of hydroxylamine will be between about 15 to about 20% (w/w). In one embodiment, the concentration of the hydroxylamine (free base or as a salt) used will be around 18% (w/w) or about 20% (w/w).

Any suitable base may be used in the reaction including, but not limited to, alkali metal hydroxides or alkoxides, or alkaline earth hydroxides or alkoxides. In some embodiments, alkali metal carbonates or bicarbonates may be used. In one embodiment, the reaction is carried out with an alkali metal hydroxide including, but not limited to, lithium hydroxide, sodium hydroxide, potassium hydroxide or cesium hydroxide. In one embodiment, the base is in the form of an aqueous solution.

In other embodiments, an organic base may be used in the reaction. Organic bases include, but are not limited to, amine bases such as triethylamine, tributylamine, diisopropylethylamine, 1,5,7-Triazabicyclo(4.4.0)dec-5-ene (TBD), 7-Methyl-1,5,7-triazabicyclo(4.4.0)dec-5-ene (MTBD), 1,8-Diazabicyclo[5.4.0]undec-7-ene (DBU), 1,5-Diazabicyclo[4.3.0]non-5-ene (DBN), 1,1,3,3-Tetramethylguanidine (TMG), Quinuclidine, 2,2,6,6-Tetramethylpiperidine (TMP), Pempidine (PMP), 1,4-Diazabicyclo[2.2.2]octan (TED), Collidine, 2,6-Lutidine (2,6-Dimethylpyridine), N, N, N', N'-tetramethyl-1,8-naphthalenediamine (Proton Sponge®), and the like. In another embodiment, phosphazene bases may be used in the process of the invention.

The base may be used in an amount of about 1 and 100 molar equivalents based on the compound of formula (II). Typically, an excess of base is used relative to the hydroxylamine reagent, especially if an acid salt of hydroxylamine is used. In other embodiments, between about 1 and about 50 equivalents of base is used relative to the compound of formula (II). In yet other embodiments, between about 1 to about 30 or between 1 to about 20 equivalents of base is used. More typically, an amount of about 1 to about 10 equivalents of base is used. In yet another embodiment, about 2 to about 8 equivalents of base is used in the reaction. In another embodiment, about 3 to about 6 equivalents of base are used. In another embodiment, about 5 equivalents or 6 equivalents of base are used. In yet another embodiment, between about 3 to about 5 equivalents of base is used. In another embodiment, about 4 to about 5 equivalents of base are used in the process. In yet another embodiment, about 4.4 equivalents of base is used.

In one embodiment, the chiral phase transfer catalyst of formula (III) may be used in an amount of about 0.1 mole % to about 20 mole % per mole of the compound of formula (II) (e.g. 0.001 mole to about 0.2 mole per mole). In another embodiment, the chiral phase transfer catalyst is used in amount of about 0.5 mole % to about 10 mole % per mole of formula (II). In yet another embodiment, the amount of catalyst used is about between 0.5 to about 10 mole % or between about 0.5 mole % to about 5 mole % per mole of the compound of formula (II). In yet another embodiment, the amount of chiral phase transfer catalyst is between about 1 mole % to about 5 mole % per mole of the compound of formula (II). In another embodiment, the amount of chiral phase transfer catalyst is between about 3 mole % to about 7 mole %. In another embodiment, the amount of chiral phase transfer catalyst used is between about 1 mole % to about 3 mole % or between about 2 mole % to about 4 mole % per mole of the compound of formula (II). In another embodiment, the amount of chiral phase transfer catalyst used is about 1 mole %, about 1.5 mole %, about 3 mole %, about 5 mole % or about 10 mole % per mole of the compound of formula (II).

Once the reaction has progressed to a suitable extent, the reaction may be worked up by procedures known by persons skilled in the art. For example, water and an aqueous acid solution may be added to the reaction mixture and the resulting mixture may be warmed slightly with stirring. The addition of a dilute acid solution neutralizes the base to achieve a somewhat neutral mixture (target pH 7-8). Any suitable acid may be used to neutralize the basic reaction mixture including dilute hydrohalides (e.g. HCl), carboxylic acids/carboxylates (e.g. acetic acid, citric acid, formic acid, etc.), ammonium salts (e.g. ammonium chloride), monobasic phosphates (e.g. $KH_2PO_4$), hydrogen bisulfate salts (e.g. $KHSO_4$), and the like. The biphasic mixture may be settled and the organic phase separated and washed with a dilute acid solution (e.g. $KH_2PO_4$ or similar) to further neutralize the mixture. The reaction mixture may be further washed with brine and the two layers allowed to settle and separate. A final wash with water may be done. The organic layer may be collected as a crude product mixture, which may be further purified prior to isolation.

The product may be purified from the crude mixture by methods known in the art. In one embodiment, a solution of the reaction mixture may be crystallized from a suitable solvent to produce the purified product. The pure product may be crystallized or re-crystallized by known methods in the art including, but not limited to, cooling a solution of the crude product in a suitable solvent (or mixture of solvents) until the product begins to crystallize, adding an antisolvent (or mixture of solvents) in which the product has low solubility, and the like. In one embodiment, the product may be crystallized by adding the desired crystallization solvent to the crude product mixture while distilling the mixture, optionally under vacuum, to exchange the reaction solvent for the crystallization solvent until a sufficient amount of the reaction solvent/solvent mixture has been removed and replaced with the desired crystallization solvent (or mixture of solvents). The mixture may then be concentrated further until a suitable concentration is achieved. As known in the art, it is desirable to adjust the concentration of the product in the crystallization solvent/mixture of solvents so that the concentration is above the saturation concentration at the temperature at which the product will be crystallized (e.g. after cooling) but below the saturation concentration at elevated temperature (e.g. in solution). Once the sufficient amount of crystallization solvent is present and the concentration of the product is suitable, crystal seed of the product may be added to the mixture at a suitable temperature to induce crystallization when the mixture is cooled. These processes are well known in the art to skilled persons.

In one embodiment, the product may be crystallized or re-crystallized from an aromatic solvent. Various aromatic solvents may be used to crystallize or re-crystallize the product. These solvents include those aromatic solvents known in the art to be acceptable for use in the manufacturing of pharmaceutical active agents including, but not limited to toluene, ethyl benzene, chlorobenzene, xylenes (mixture of isomers or pure isomers), anisole, and the like. In one preferred embodiment, the product may be crystallized or re-crystallized from toluene. In one embodiment, the product may be crystallized or re-crystallized from ethyl benzene. In yet another embodiment, the product may be crystallized or re-crystallized from chlorobenzene. In another embodiment, the product is crystallized or re-crystallized from anisole. In another embodiment, the product is crystallized or re-crystallized from xylenes. It may also be possible to crystallize the product from benzene, although this is not preferred because of the toxicity issues related to this solvent.

In one embodiment, the product may be crystallized or re-crystallized from solvent mixture comprising a polar solvent in which the product is soluble and a non-polar solvent in which the product is not very soluble. In another embodiment, the product may be crystallized or re-crystallized from hexanes, heptane, cyclohexane and the like. In one embodiment, the re-crystallization of the product isolated as a solvate with an aromatic solvent (e.g. toluene solvate) may be re-crystallized with a polar/non-polar solvent combination to further purify the product and/or to remove the aromatic solvent component of the solvate. In yet another embodiment, the product may be crystallized or re-crystallized from a mixture of solvents including a mixture comprising an aromatic solvent, an aliphatic solvent, an alcohol solvent, an ether solvent, an ester solvent, and the like, or a mixture thereof. Suitable alcohols include, but are not limited to, $C_1$-$C_6$ aliphatic alcohols such as ethanol, isopropanol, 1-propanol, 1-butanol, sec-butanol, and the like.

In one embodiment, the product may be crystallized or re-crystallized from a mixture of an aromatic solvent and an aliphatic solvent. In another embodiment, the product may be crystallized or re-crystallized from a mixture of an aliphatic solvent and an alcohol solvent. In yet another embodiment, the product may be crystallized or re-crystallized from a mixture of an aromatic solvent and an alcohol solvent. In one embodiment, the product may be crystallized or re-crystallized from a mixture of a cycloalkyl solvent and an alcohol solvent. In another embodiment, the product may be crystallized or re-crystallized from a mixture of a cycloalkyl solvent and a $C_1$-$C_6$ alcohol solvent. In one embodiment, the product may be crystallized or re-crystallized from a mixture of hexanes/ethanol, toluene/cyclohexane, toluene/hexanes, toluene/heptane, cyclohexane/ethanol or toluene/ethanol, and the like. It will be apparent to skilled persons in the art that ratio of each solvent in the solvent combinations will be adjusted to obtain a solvent combination in which the product is reasonably soluble at higher temperatures but not very soluble when the mixture is cooled. The solvent ratio can be adjusted to decrease the solubility of the product at the appropriate time. For example, an additional amount of the poorer solvent in a mixture may be added once the solid has dissolved to bring the solution closer to the saturation point. Of course, it will be apparent to the skilled person that the product may be recrystallized one or more times from a suitable solvent/solvent mixture to improve the purity of the product, if necessary.

In one embodiment of the invention, the (S)-enantiomer of afoxolaner prepared by the process of the invention is crystallized from toluene to produce crystals of very high purity. It was surprisingly found that the (S)-enantiomer of afoxolaner forms a crystalline solvate with toluene (see example 12) while racemic afoxolaner does not. Because of this characteristic, the crystallization of the desired (S)-enantiomer from toluene resulted in a significant improvement of the enantiomeric purity of the product compared with the ratio of enantiomers in the completed reaction mixture. The selective crystallization of (S)-afoxolaner with other aromatic solvents has also been achieved (e.g. anisole, chlorobenzene, etc). This is surprising because typically one enantiomer will not be enriched over the other enantiomer unless the crystallization is conducted using a chiral system in which there is a preference for one enantiomer over the other. Crystallizations of this type are known using, for example, chiral bases when the chiral product is an acid. However, it is very surprising that the crystallization of one enantiomer from a non-chiral solvent such as toluene results in not only the purification of the product (e.g. removal of non-chiral reaction impurities and starting material) but also results in the enrichment of the desired enantiomer.

The crystallization of the desired enantiomerically pure isoxazoline compounds of the invention from a suitable solvent including, but not limited to, those described above may be achieved by a solvent switch from the reaction solvent to the solvent used for crystallization at a suitable volume by distillation, optionally under vacuum, as known to those skilled in the art. In one embodiment, the worked-up reaction mixture may be concentrated to a volume such as between about 0.5 to 30 volumes based on the compound of formula (II). More typically, the worked-up reaction mixture may be concentrated to a volume of between about 1 to about 20 or between about 2 and 10 volumes. In other embodiments, the reaction mixture is concentrated to between about 1 to about 5 volumes, about 1 to about 3 volumes or between about 1 to about 2 volumes.

Once a suitable amount of the reaction solvent has been removed, a suitable amount of the crystallization solvent is added and the volume of the mixture is adjusted by distillation (optionally under vacuum) to an appropriate volume (optionally with further addition of crystallization solvent) so that the product will crystallize out of solution upon cooling. In principle, the volume from which the product is not critical; however, having too much solvent in the crystallization may result in higher losses of product in the mother liquors. On the other hand, crystallizing the product from a mixture that is too concentrated may result in poorer quality product. The volume of the pre-crystallization mixture depends on the solubility of the product in the crystallization solvent. In one embodiment, the pre-crystallization volume may be between about 1 volume to about 30 volumes. In some embodiments, the volume of the pre-crystallization mixture may be between about 1 volume and about 20 volumes or between about 1 volume to about 10 volumes. More typically, the volume of the pre-crystallization mixture may be from about 2 volumes to about 10 volumes, about 3 volumes to about 8 volumes or about 4 volumes to about 7 volumes. In one embodiment, the pre-crystallization volume may be about 5-6 volumes before cooling the mixture.

When the pre-crystallization mixture is cooled slowly the desired product will crystallize out of solution and may be isolated by filtration. Since there is always some amount of the undesired enantiomer, it is possible with certain isoxazoline compounds that the undesired enantiomer or the racemic compound may crystallize out of solution faster than the desired enantiomer. For example, it was found that in one embodiment of the invention for the synthesis of (S)-afoxolaner that racemic afoxolaner crystallized out (unsolvated) of solution from toluene faster than the pure (S)-enantiomer. The crystals of the racemic afoxolaner have a higher melting point than the crystals of the (S)-enantiomer solvate. Thus, the crystals of the racemic compound may be removed by adjusting the temperature of the mixture to a temperature where the racemic compound crystallizes out of solution and then filtering off the solid to afford the desired enantiomer in solution. Seed of the undesired enantiomer or racemic compound to induce crystallization of these compounds may be added. Once most of the racemic compound is removed, the volume of the filtrate may be adjusted further (e.g. by distillation or addition of more crystallization solvent) and the solution cooled to induce crystallization of the desired compound.

In one embodiment, the crystallization of the racemic compound may be conducted by seeding with crystals of the racemic compound at a low temperature to induce crystallization of the compound, aging the mixture for a suitable time, heating to dissolve most of the desired enantiomer, aging at the higher temperature and filtering the mixture to remove the solid. In one embodiment, the seeding and crystallization of the racemic compound is conducted at a temperature of between about −10° C. to about 30° C. In other embodiments, the seeding step is conducted between about 0° C. to about 20° C., about 0° C. to about 15° C. or about 5° C. to about 15° C. In another embodiment, the seeding and crystallization is conducted by seeding with the racemic compound at a temperature of about 7° C. to about 13° C. and aging for a suitable time to ensure that most of the racemic compound has crystallized.

The mixture is then heated to a higher temperature to dissolve the desired enantiomer while maintaining the crystals of the racemic compound. In one embodiment, the mixture is heated to a temperature of about 30° C. to about 100° C. More typically, the mixture is heated to about 30° C. to about 80° C. and aged for a suitable time to dissolve the desired enantiomer while keeping the racemic compound in solid form. Even more typically, the mixture is heated to a temperature of between about 40° C. to about 70° C., about 50° C. to about 70° C. or about 55° C. to about 65° C. In yet another embodiment, the mixture is heated to about 57° C. to about 63° C. and aged for a suitable amount of time. The mixture is then filtered to remove the solid comprising the undesired racemic compound.

The resulting filtrate is crystallized by again adjusting the volume to the desired volume using distillation and/or addition of more crystallization solvent and then cooling slowly to a suitable temperature to induce crystallization of the desired enantiomer. In one embodiment, the mixture is cooled to a temperature of about −10° C. to about 30° C. In other embodiments, the seeding step is conducted between about 0° C. to about 20° C., about 0° C. to about 15° C. or about 5° C. to about 15° C. In another embodiment, the mixture is cooled to a temperature of about 7° C. to about 13° C. Once at the desired temperature, the mixture may be seeded with crystals of the desired enantiomer and aged for a suitable time. The product is isolated by filtration or centrifugation and the cake is washed with the crystallization solvent. The resulting solid is then dried, optionally under vacuum.

In some embodiments, the product may be re-crystallized using the same crystallization solvent or an alternate solvent to further purify the material. A similar process as described above may be used with the exception that the pre-crystallization of the undesired enantiomer or racemic compound will not likely be necessary. In one embodiment, the desired enantiomer of the isoxazoline compound may be re-crystallized from a mixture of an aliphatic solvent and an alcohol solvent. In another embodiment, the isoxazoline compound may be re-crystallized from a mixture of an aliphatic solvent and a $C_1$-$C_6$ alcohol solvent. In another embodiment, the isoxazoline compound may be re-crystallized from a mixture of a cycloalkyl solvent and a $C_1$-$C_6$ alcohol solvent. In yet another embodiment, the isoxazoline compound may be re-crystallized from a mixture of cyclohexane/ethanol.

In one embodiment using a solvent combination of an aliphatic and an alcohol solvent, the mixture containing the solid product and the crystallization solvent is heated to dissolve the solid and then cooled to a suitable temperature to seed the solution with seed crystals of the product, if desired. Seeding the crystallization mixture is optional but may be desired to form larger crystal of the desired form. In another embodiment, the product is first dissolved in the solvent in which the compound is more soluble (e.g. alcohol solvent) and the other solvent is added at elevated temperature.

In one embodiment, in which a solvent mixture of an alcohol solvent and an aliphatic solvent is used for crystallization of the product, a volume ratio of about 1:10 to 1:99, volume of alcohol to volume of aliphatic solvent may be used. More typically, a volume ratio of from about 1:5 to about 1:40 or about from about 1:5 to about 1:30, volume of alcohol to volume of aliphatic solvent, may be used. In another embodiment, the volume ratio of an alcohol solvent and aliphatic solvent in a mixture may be from about 1:5 to about 1:15, from about 1:8 to about 1:13 or from about 1:10 to about 1:13, volume of alcohol to volume of aliphatic solvent. In another embodiment, the volume ratio of an alcohol solvent to aliphatic solvent in a solvent mixture may be from about 1:10 to about 1:30 or about 1:15 to about 1:25. In yet another embodiment, the volume ratio of an alcohol solvent to aliphatic solvent in a solvent mixture may be from about 1:20.

The amount of aliphatic solvent used in the crystallization of the isoxazoline compounds of the invention when part of a solvent system with an alcohol solvent will also depend on the specific aliphatic solvent used and the specific isoxazoline compound. In one embodiment, the amount of aliphatic solvent used may be from about 5 to about 30 volumes based on the volume of the product re-crystallized or on the volume of the starting material if crystallized from the synthesis sequence. In other embodiments, from about 5 to about 20 volumes of an aliphatic solvent may be used. More typically, from about 10 to about 20 volumes of an aliphatic solvent may be suitable. In one embodiment, from about 13 to about 16 volumes of an aliphatic solvent may be used.

In one embodiment, the mixture is heated to a temperature of between about 40° C. to about 70° C. to dissolve the solid. More typically, the mixture is heated to a temperature of between about 50° C. to about 70° C. or between about 55° C. to about 65° C. In one embodiment, the mixture is heated to temperature of between about 57° C. to about 63° C. to dissolve the solid.

Once the solid is dissolved, additional solvent may be added to bring the mixture to a point at or just above saturation. Typically, the solvent which is added is one in which the product is less soluble. The resulting mixture may be cooled slightly to bring the mixture to the saturation point and then optionally seeded with crystals of the desired enantiomer. The mixture is then slowly cooled further to a suitable temperature and then aged. The product is isolated by filtration or centrifugation and the product is dried optionally under vacuum.

The temperature at which the crystallization mixture is seeded (if done) depends on the isoxazoline compound and the solvents used for the crystallization. In one embodiment, the seeding of the pre-crystallization mixture is conducted at a temperature of between about 10° C. to about 80° C. or between about 20° C. to about 70° C. In one embodiment, the seeding of the pre-crystallization mixture is done at a temperature of between about 40° C. to about 65° C. In other embodiments, the pre-crystallization mixture is seeded at a temperature of between about 45° C. to about 65° C. or between about 50° C. to about 60° C. In one embodiment, the mixture is seeded with crystals of the desired product at a temperature of about 52° C. to about 58° C. and stirred for a suitable time. In one embodiment, the seeded mixture is heated for at least 30 minutes or at least an hour.

After seeding with seed crystals of the desired product, in some embodiments the mixture may be cooled to an intermediate temperature (e.g. between the final crystallization temperature and the seeding temperature) and aged. The mixture may also be re-heated to a temperature close to or slightly above the temperature at which the mixture was seeded and then re-cooled slowly. This process is conducted in to enable the crystals formed to grow before the final cool-down and crystallization.

The seeded mixture is then finally slowly cooled to a lower temperature to complete the crystallization process. In one embodiment, the seeded mixture is cooled to a temperature below about 30° C. to crystallize the desired product. In one embodiment, the mixture is cooled to a temperature of between about −10° C. to about 30° C. In other embodiments, the seeding step is conducted between about 0° C. to about 20° C., about 0° C. to about 15° C. or about 5° C. to about 15° C. In another embodiment, the mixture is cooled to a temperature of about 7° C. to about 13° C. In another embodiment, the seeded mixture is cooled below about 20° C. or below about 15° C. and aged to complete the crystallization of the product. The mixture is aged and then solid is isolated by filtration or centrifugation. The product is dried, optionally under vacuum, to provide the desired product.

It will be appreciated by those of skill in the art that the rate of cooling is very important in the crystallization process. If the rate of cooling is too rapid, solubility of the compound in the solvent will drop too quickly and the crystals will not be able to grow to produce the product in the desired crystal form and quality. In some embodiments, the crystallization mixture is cooled at a rate of between about 20° C./hour and 1° C./hour to ensure that the crystals of the desired product can grow at a suitable rate to ensure the purity of the product. More typically, the crystallization mixture is cooled at a rate of between about 15° C./hour and 1° C./hour or about 10° C./hour and 5° C./hour. In one embodiment, the crystallization mixture is cooled at a rate of about 8° C./hour and 3° C./hour to the target temperature.

The product is dried at a temperature of between about room temperature and 80° C., optionally under vacuum. In other embodiments, the product is dried at a temperature of between about 30° C. to about 70° C., optionally under vacuum. In yet other embodiments, the product is dried at a temperature of between about 40° C. to about 60° C., optionally under vacuum. In one embodiment, the product is dried at a temperature of about between about 45° C. to about 55° C., optionally under vacuum.

In another embodiment, the crude product mixture may be purified by chromatography to produce the product. Purification methods using chiral stationary phases are well known in the art. For example, the desired enantiomer of the compound of formula (I) may be isolated using preparatory HPLC with a chiral stationary phase such as a Chiralpak® AD column. Other chiral columns and chromatographic methods are well known in the art.

In one embodiment of the invention, the chiral phase transfer catalyst of formula (IIIa) or (IIIb) may be attached to a polymer support so that the catalyst may be easily recovered from the reaction mixture and reused. The catalyst of formula (IIIa) or (IIIb) may be attached to a suitable polymer at several sites including on the aryl or heteroaryl group R, on the group W or on the quinoline group as shown below for formula (IIIa-13):

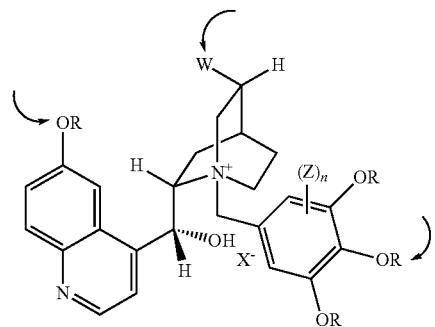

(IIIa-13)

The catalyst may be attached to a suitable polymeric support at the substituted phenyl group, for example, by reacting a hydroxyl group in the catalyst starting material with an electrophile on the catalyst. Other methods for attaching the catalyst include, for example, reacting a quinine-based catalyst where W is a vinyl group using an olefin metathesis reaction or other methods that may react with the vinyl group.

In another embodiment, the catalyst may be anchored to a suitable polymer at the quinoline group by protection of the free hydroxyl group, demethylation and alkylation to the polymer.

In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

It is also noted that in this disclosure and in the claims and/or paragraphs, the compounds of the invention are intended to include all stereoisomers and crystalline forms (which includes hydrated forms, polymorphic forms and amorphous forms.

Definitions

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

The term "aliphatic solvent" as used herein refers to solvents comprised of straight, branched, cyclic, primary, secondary or tertiary hydrocarbons. Common aliphatic solvents include, but are not limited to pentane, hexanes, heptane, octane, cyclopentane, cyclohexane, and the like, and a mixture thereof. As used herein, "aliphatic solvent" does not include aromatic solvents such as toluene.

The term "aromatic solvent" as used herein refers to solvents comprised of hydrocarbon molecules having aromatic character, optionally substituted by halogen. Common aromatic solvents include, but are not limited to, benzene, toluene, o-xylene, p-xylene or a mixture thereof (xylenes), fluorobenzene, chlorobenzene, o-dichlorobenzene, anisole and mesitylene, and a mixture thereof.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl", which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-S(O)$_2$—, wherein alkyl is as defined above. Similarly, the term "haloalkylsulfonyl" refers to haloalkyl-S(O)$_2$— where haloalkyl is as defined above.

The term alkylamino and dialkylamino refer to alkyl-NH— and (alkyl)$_2$N— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl," "haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—$CH_2$-)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, cinnolinyl, quinazolinyl, quinoxalinnyl, phthalazinyl, 1,2,3-benzotriazinyl, 1,2,4-benzotriazinyl, furanyl, thienyl, furyl, pyrrolyl, imidazolyl, oxazolyl, isoxazolyl, isothiazolyl, 1,3,4-thiadazolyl, pyrazolyl benzofuranyl, and benzothienyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$)).

The term "amorphous" as applied to afoxolaner herein refers to a solid state wherein the afoxolaner molecules are present in a disordered arrangement and do not form a distinguishable crystal lattice or unit cell. When subjected to X-ray powder diffraction, amorphous afoxolaner does not produce any characteristic crystalline peaks.

The term "chemical purity" refers to the overall level of a desired product. If a compound is present in enantiomeric forms, "chemical purity" as used herein would include both enantiomeric forms in the calculation of the overall level of the desired product. If a compound is present in solvate forms, "chemical purity" as used herein would include the solvate in the calculation of the overall level of the desired product. Impurities may be in the form of, for example, the presence of unwanted process reagents, process intermediates, degradation products or oxidation products. In particular embodiments the chemical purity is high, that is greater than 90% chemical purity, especially above 92.5%, 95%, 96%, 97%, 98%, 99% and includes 100%. The purity may be measured a variety of techniques, including HPLC analysis.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "enantiomeric excess" or "e.e." as used herein refers to a difference between the amount of one enantiomer and the amount of the other enantiomer that is present in the product mixture. The enantiomeric excess value in each example given below gives an indication of the relative amount of each enantiomer. The value is defined as the difference between the relative percentages for the two enantiomers. Thus, for example, when the percentage of the (S)-enantiomer of the compound of the invention is 97.5% and the percentage for the (R)-enantiomer is 2.5%, the enantiomeric excess for the (S)-enantiomer is 95%.

As used herein, the term "chiral purity" or "enantiomeric purity" refers to the percentage of the HPLC area of subject enantiomer of the compound relative to the HPLC area of the combination of both enantiomers in the mixture measured by chiral HPLC, excluding other compounds or impurities. For example, the chiral purity of the (S)-enantiomer of afoxolaner is calculated by the equation S/(S+R)×100%, with S and R representing peak areas of (S)-afoxolaner and (R)-afoxolaner, respectively, measured by chiral HPLC.

The term "isolated" as used herein, in reference to solid state forms of afoxolaner of the present disclosure corresponds to a solid state form of afoxolaner that is physically separated from the reaction mixture in which it is formed.

The term "non-solvate polymorph" or "non-solvate crystalline form" refers to a crystalline form that does not have a solvent molecule bound in the crystal lattice. However, the crystals may contain trace amount of solvate not bound in the crystal lattice.

The term "polymorph", as used herein, refers to the different crystal structures (of solvated or non-solvated forms) in which a compound can crystallize.

The term "racemic" or "racemate", and other like terms refer to generally equimolar proportions two enantiomers of a compound. For example, afoxolaner is a racemate containing equamolar quantities of the (S)- and (R)-enantiomers of the compound.

The term "seed" as used herein can be used as a noun to describe one or more crystals of a crystalline compound (e.g., racemic afoxolaner) used to induce crystallization of the compound. For example, if it is desired to produce crystalline afoxolaner (racemic), the seed crystals to be used to enhance the crystallization process can be crystals of racemic afoxolaner. The term "seed" or "seeding" can also be used as a verb to describe the act of introducing said one or more crystals of a compound into an environment (including, but not limited to e.g., a solution, a mixture, a suspension, or a dispersion) thereby resulting in the formation of more of the same crystals of the compound (e.g., formation of racemic afoxolaner compound).

The term or "hydrate", "hydrate polymorph" or "hydrate crystalline form" refers to a crystalline form of a compound that has one or more molecules of water bound in the crystal lattice.

The term or "solvate", "solvate polymorph" or "solvate crystalline form" refers to a crystalline form of a compound that has one or more molecules of a solvent bound in the crystal lattice.

Stereoisomers and Polymorphic Forms

As discussed above, it will be appreciated by those of skill in the art that certain compounds may exist and be isolated as optically active and racemic forms. Compounds having one or more chiral centers, such as the isoxazoline active agents of the invention, may be present as single enantiomers or diastereomers or as mixtures of enantiomers and/or diastereomers. Chiral centers in molecules may include a sulfur atom. For example, it is well known in the art that sulfoxide compounds may be optically active and may exist as single enantiomers or racemic mixtures. In addition, compounds of the invention may include other chiral centers in addition to the chiral carbon atom in the isoxazoline ring, which results in a theoretical number of optically active isomers. Where compounds within the compositions of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein.

The compounds within the compositions of present invention may also be present in different solid forms such as different crystalline forms or in the form of an amorphous solid. The present invention encompasses different crystalline forms as well as amorphous forms of the inventive compounds. In addition, the compounds within the compositions of the invention may exist as hydrates or solvates, in which a certain stoichiometric amount of water or a solvent is associated with the molecule in the crystalline form. The compositions of the invention may include hydrates and solvates of the active agents.

In one embodiment, the present invention covers a crystalline solvated solid form of the isoxazoline compounds of formula (I) with an aromatic solvent. In a particularly embodiment, the present invention covers a crystalline solvated solid form of (S)-afoxolaner with an aromatic solvent. In a particularly preferred embodiment, the invention provides a crystalline toluene solvate of (S)-afoxolaner. As discussed above, crystallization of the (S)-enantiomer of afoxolaner from a mixture of the (S)- and (R)-enantiomers of afoxolaner enriched in the (S)-enantiomer obtained from the reaction of compound (IIA-1) with hydroxylamine in the presence of a base and a chiral phase transfer catalyst of formula (IIIa-13-1) results in a surprising purification of the product and enrichment of the desired (S)-enantiomer. Depending upon the intended use of the solid state form of afoxolaner, processing considerations may favor selection of a specific solid state form or a specific combination of such solid state forms. Use of a solvated crystalline form, such as a crystalline toluene solvate form, instead of non-solvated forms in a composition may eliminate a processing step, namely desolvation, for those processes that otherwise would proceed by desolvation of a solvated crystalline form. E. Shefter and T. Higuchi have measured the relative rates of dissolution of several crystalline solvated and non-solvated forms of important pharmaceuticals, J. Pharm. Sci., 52 (8), (1963), 781-91.

The crystalline toluene solvate of (S)-afoxolaner has been found to contain two molecules of the compound and two molecules of toluene as shown in FIG. 9 and described in Example 12. The toluene solvate of (S)-afoxolaner is may be prepared by crystallization of (S)-afoxolaner from pure toluene or from a solvent mixture containing toluene (e.g. cyclohexane/toluene) by methods known in the art, including the processes described in Examples 7, 8 and 12. The crystallization may also be conducted by by dissolving (S)-afoxolaner or a sample of afoxolaner enriched in the (S)-enantiomer in toluene or a solvent mixture containing toluene at a concentration that is a suspension at a temperature at which the compound will be crystallized (e.g. ambient temperature or below) and a solution at elevated temperature and then cooling slowly to the target temperature to induce crystallization of the desired (S)-afoxolaner toluene solvate.

In one embodiment, (S)-afoxolaner is dissolved in toluene (optionally in the presence of a second solvent) at an elevated temperature and then cooled to induce crystallization. In another embodiment, (S)-afoxolaner is dissolved in toluene or a solvent mixture comprising toluene, by heating the combination to a temperature of about 30° C. to the boiling point of the solvent. In another embodiment, (S)-afoxolaner is dissolved in toluene or a solvent mixture comprising toluene, by heating the combination to a temperature of between about 30° C. to about 100° C.

More typically, (S)-afoxolaner is dissolved in toluene or a solvent mixture comprising toluene, by heating the combination to a temperature of between about 30° C. to about 80° C., between about 50° C. to about 80° C., between about 40° C. to about 70° C. or between about 50° C. to about 70° C. In another embodiment, the mixture is heated to a temperature of between about 55° C. to about 65° C. or between about 50° C. to about 60° C. In another embodiment, the mixture is heated to a temperature of between about 30° C. to about 50° C.

Once the mixture of (S)-afoxolaner in toluene or a solvent mixture comprising toluene is in solution, the crystalline toluene solvate of (S)-afoxolaner is obtained by slowly cooling the mixture. In one embodiment, the mixture is cooled to a temperature of less than about 30° C. or less than about 20° C. In other embodiments, the mixture is cooled slowly to less than about 15° C. or less than about 10° C. In yet another embodiment, the mixture is cooled to less than about 5° C.

When the crystallization is conducted in the presence of a second solvent, the ratio of toluene and the second solvent may be from about 20:80 to about 99:1 toluene to the second solvent by volume. In other embodiments, the volume ratio of toluene to the second solvent may be between about 30:70 to about 99:1, between about 40:60 to about 99:1 or between about 50:50 to about 99:1. In other embodiments, the ratio of toluene to the second solvent may be between about 40:60 to about 90:10, between about 50:50 to about 90:10 or between about 50:50 to about 80:20. In other embodiments, the ratio may be between about 40:60 to about 80:20, about 50:50 to about 75:25, toluene to the second solvent, by volume. In one embodiment, the second solvent will be an aliphatic solvent including, but not limited to, pentane, hexanes, heptane, octane, cyclopentane, cyclohexane, and the like.

In some embodiments, the crystalline toluene solvate of (S)-afoxolaner may be prepared by dissolving the compound in toluene or a solvent mixture comprising toluene, and adding a solvent to the mixture in which (S)-afoxolaner has low solubility (e.g. an antisolvent). In one embodiment, crystallization of the crystalline toluene solvate of (S)-afoxolaner may be induced by addition of an aliphatic solvent such as those described above.

Once the crystalline toluene solvate of (S)-afoxolaner is formed, it may be isolated by filtration or other methods known in the art (e.g. centrifugation) and dried, optionally under vacuum, to remove excess solvent.

The source of (S)-afoxolaner for the crystallization may be another solid form of (S)-afoxolaner (e.g. amorphous or other crystalline form) or a solution containing (S)-afoxolaner in another solvent as in Examples 7 and 8. Other methods of crystallization known in the art may be used.

In one embodiment, the invention provides a crystalline toluene solvate of (S)-afoxolaner (structure shown below),

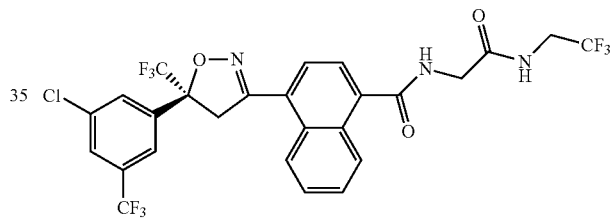

as characterized by X-Ray Powder Diffraction (XRPD) and/or Differential Scanning Calorimetry (DSC) described in Example 12.

In one embodiment, the invention provides a crystalline toluene solvate of (S)-afoxolaner that exhibits one or more of the characteristic peaks expressed in degrees 2-theta (2θ)±0.2 shown in Table 2 below and FIG. 8 as determined by the method described in Example 12.

TABLE 2

|  | Angle 2-Theta ° |
|---|---|
| 1 | 4.859 |
| 2 | 8.516 |
| 3 | 8.823 |
| 4 | 9.735 |
| 5 | 10.778 |
| 6 | 11.644 |
| 7 | 12.161 |
| 8 | 12.746 |
| 9 | 14.591 |
| 10 | 15.136 |
| 11 | 16.694 |
| 12 | 16.999 |
| 13 | 17.616 |
| 14 | 18.411 |
| 15 | 18.838 |

TABLE 2-continued

| | Angle 2-Theta ° |
|---|---|
| 16 | 19.540 |
| 17 | 19.894 |
| 18 | 20.937 |
| 19 | 21.484 |
| 20 | 21.859 |
| 21 | 22.236 |
| 22 | 22.985 |
| 23 | 23.431 |
| 24 | 24.540 |
| 25 | 25.291 |
| 26 | 25.643 |
| 27 | 26.359 |
| 28 | 27.143 |
| 29 | 28.472 |
| 30 | 29.223 |
| 31 | 29.776 |
| 32 | 30.638 |
| 33 | 32.865 |
| 34 | 33.120 |
| 35 | 33.782 |
| 36 | 34.529 |
| 37 | 37.046 |
| 38 | 38.405 |
| 39 | 39.648 |

In another embodiment, the invention provides a crystalline toluene solvate of (S)-afoxolaner that exhibits one or more of the characteristic peaks expressed in degrees 2-theta (2θ)±0.2 shown in Table 3 below and FIG. 8 as determined by the method described in Example 12.

TABLE 3

| | Angle 2-Theta ° |
|---|---|
| 1 | 4.859 |
| 2 | 22.236 |
| 3 | 18.838 |
| 4 | 8.516 |
| 5 | 25.643 |
| 6 | 25.291 |
| 7 | 21.859 |
| 8 | 18.411 |
| 9 | 19.894 |
| 10 | 12.746 |
| 11 | 23.431 |
| 12 | 16.999 |
| 13 | 10.778 |
| 14 | 14.591 |
| 15 | 27.143 |
| 16 | 12.161 |
| 17 | 17.616 |
| 18 | 15.136 |
| 19 | 9.735 |
| 20 | 11.644 |

In another embodiment, the invention provides a crystalline toluene solvate of (S)-afoxolaner that exhibits one or more of the characteristic peaks expressed in degrees 2-theta (2θ)±0.2 shown in Table 4 below and FIG. 8 as determined by the method described in Example 12.

TABLE 4

| | Angle 2-Theta ° |
|---|---|
| 1 | 4.859 |
| 2 | 22.236 |
| 3 | 18.838 |
| 4 | 8.516 |

TABLE 4-continued

| | Angle 2-Theta ° |
|---|---|
| 5 | 25.643 |
| 6 | 25.291 |
| 7 | 21.859 |
| 8 | 18.411 |
| 9 | 19.894 |
| 10 | 12.746 |

In another embodiment, the invention provides a crystalline toluene solvate of (S)-afoxolaner that exhibits at least seven of the characteristic peaks expressed in degrees 2-theta (2θ)±0.2 at one or more of the positions shown in Table 2, Table 3 or Table 4 above and FIG. 8 as determined by the method described in Example 12.

In another embodiment, the invention provides a crystalline toluene solvate of (S)-afoxolaner that exhibits at least five of the characteristic peaks expressed in degrees 2-theta (2θ)±0.2 at one or more of the positions shown in Table 2, Table 3 or Table 4 above and FIG. 8 as determined by the method described in Example 12.

In another embodiment, the invention provides a crystalline toluene solvate of (S)-afoxolaner that exhibits at least three of the characteristic peaks expressed in degrees 2-theta (2θ)±0.2 at one or more of the positions shown in Table 2, Table 3 or Table 4 above and FIG. 8 as determined by the method described in Example 12.

In another embodiment, the invention provides a crystalline toluene solvate of (S)-afoxolaner that exhibits an endotherm between about 70° C. and about 90° C. as described in Example 12 and shown in FIG. 7.

In another embodiment, the invention provides a crystalline toluene solvate of (S)-afoxolaner that exhibits an endotherm between about 75° C. and about 90° C. as described in Example 12 and shown in FIG. 7.

In another embodiment, the invention provides a crystalline toluene solvate of (S)-afoxolaner that exhibits an endotherm between about 80° C. and about 90° C. as described in Example 12 and shown in FIG. 7.

In another embodiment, the invention provides a crystalline toluene solvate of (S)-afoxolaner that exhibits an endotherm between about 83° C. and about 87° C. as described in Example 12 and shown in FIG. 7.

In another embodiment, the invention provides a crystalline toluene solvate of (S)-afoxolaner that exhibits an endotherm about 85° C. as described in Example 12 and shown in FIG. 7.

In another embodiment, the invention provides a crystalline toluene solvate of (S)-afoxolaner that exhibits an endotherm about 84.7° C. as described in Example 12 and shown in FIG. 7.

In another embodiment, the invention provides a crystalline toluene solvate of (S)-afoxolaner, wherein at least 90% of the solid form is a crystalline toluene solvate form.

In another embodiment, the invention provides a crystalline toluene solvate of (S)-afoxolaner, wherein at least 80% of the solid form is a crystalline toluene solvate form.

In another embodiment, the invention provides a crystalline toluene solvate of (S)-afoxolaner, wherein at least 70% of the solid form is a crystalline toluene solvate form.

In another embodiment, the invention provides a crystalline toluene solvate of (S)-afoxolaner, wherein at least 60% of the solid form is a crystalline toluene solvate form.

In another embodiment, the invention provides pesticidal or parasiticidal compositions comprising a crystalline toluene solvate form of (S)-afoxolaner alone, or in combination with other active agents, together with agriculturally or pharmaceutically acceptable carriers or diluents.

In another embodiment, the invention provides pesticidal or parasiticidal compositions comprising a crystalline toluene solvate of (S)-afoxolaner alone, or in combination with one or more additional active agents, and agriculturally or pharmaceutically acceptable carriers or diluents, wherein at least 80% of the solid form of (S)-afoxolaner is a crystalline toluene solvate form of (S)-afoxolaner.

In another embodiment, the invention provides pesticidal or parasiticidal compositions comprising a crystalline toluene solvate of (S)-afoxolaner alone, or in combination with one or more additional active agents, and agriculturally or pharmaceutically acceptable carriers or diluents, wherein at least 70% of the solid form of (S)-afoxolaner is a crystalline toluene solvate form of (S)-afoxolaner.

In another embodiment, the invention provides pesticidal or parasiticidal compositions comprising a crystalline toluene solvate of (S)-afoxolaner alone, or in combination with one or more additional active agents, and agriculturally or pharmaceutically acceptable carriers or diluents, wherein at least 60% of the solid form of (S)-afoxolaner is a crystalline toluene solvate form of (S)-afoxolaner.

Salts

Also contemplated within the scope of the invention are acid or base salts, where applicable, of the compounds of the invention provided for herein.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4$), alkyl- and dialkylammonium salts, and salts of cyclic amines such as the morpholine and piperidine salts.

Veterinary Compositions

The compounds of formula (I) enriched in the (S)-enantiomer and compositions comprising the compounds are useful for the prevention and treatment of parasitic infestations/infections in animals. The compositions of the invention comprise an effective amount of at least one isoxazoline compound of formula (I) enriched in the (S)-enantiomer, or a pharmaceutically acceptable salt thereof, in combination with a pharmaceutically acceptable carrier or diluent and optionally other non-active excipients and optionally in combination with one or more additional active agents. In a preferred embodiment, the veterinary parasiticidal compositions of the invention comprise an effective amount of an isoxazoline of formula IA as described above enriched in the (S)-enantiomer, or a pharmaceutically acceptable salt thereof, wherein $X^1$, $X^2$ and $X^3$ are H, chloro, fluoro or $CF_3$. In another preferred embodiment, the invention provides veterinary parasiticidal compositions comprising afoxolaner enriched in the (S)-enantiomer as described above.

The compositions may be in a variety of solid and liquid forms which are suitable for various forms of application or administration to an animal. For example, the veterinary compositions comprising the inventive compounds may be in compositions suitable for oral administration, injectable administration, including subcutaneous and parenteral administration, and topical administration (e.g. spot-on or pour-on). The compositions are intended to be administered to an animal including, but not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compounds of formula (I) enriched in the (S)-enantiomer to protect companion animals, such as dogs and cats, and livestock animals, such as cattle and sheep, from ectoparasites is particularly useful.

Agricultural Compositions

In another embodiment, the invention provides agricultural compositions comprising the compounds of formula (I), formula IA enriched in the (S)-enantiomer, including (S)-afoxolaner. The compositions may be used for combating pests that damage plants, plant propagation material and crops, or material derived from wood. According to the present invention, the compounds of formula (I) enriched in the (S)-enantiomer can be converted into the customary compositions, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula (I) according to the present invention.

The invention further provides an agricultural composition for combating such animal pests, which comprises such an amount of at least one compound of formula (I), formula IA wherein $X^1$, $X^2$ and $X^3$ are H, chloro, fluoro or $CF_3$ enriched in the (S)-enantiomer, including (S)-afoxolaner, or agriculturally useful salts thereof, and at least one inert liquid and/or solid agriculturally acceptable carrier that has a pesticidal action and, if desired, at least one surfactant. Such a composition may contain a single active compound of formula (I) enriched in the (S)-enantiomer, or a salt thereof, or a mixture of several active compounds of formula (I) enriched in the (S)-enantiomer, or their salts, according to the present invention.

The compositions are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8, all of which are hereby incorporated by reference in their entirety), for example by extending the active compound with auxiliaries suitable for the composition of agrochemicals, such as solvents and/or carriers, if desired emulsifiers, surfactants and dispersants, preservatives, antifoaming agents, anti-freezing agents, for seed treatment composition also optionally colorants and/or binders and/or gelling agents.

Veterinary Uses and Methods

As discussed above, the compounds of formula (I) enriched in the (S)-enantiomer are effective against ectoparasites and may be used to treat and prevent parasitic infestations in or on animals. In one embodiment, the present invention provides a method of treating or preventing an ectoparasite infestation in or on an animal (e.g. a mammal or bird) comprising administering an ectoparasiticidally effective amount of a compound of formula (I) enriched in the (S)-enantiomer, or pharmaceutically acceptable salts thereof, or a composition comprising the compound, to the animal. In another embodiment, the methods of the invention comprise administering an effective amount of a compound of formula IA wherein $X^1$, $X^2$ and $X^3$ are H, chloro, fluoro or $CF_3$ enriched in the (S)-enantiomer, or a pharmaceutically acceptable salt thereof, to the animal. In a preferred embodiment, the methods of the invention comprise administering an effective amount of afoxolaner enriched in the (S)-enantiomer, or a pharmaceutically acceptable salt thereof, to the animal.

In another embodiment when the compounds of formula (I) or IA enriched in the (S)-enantiomers, including (S)-afoxolaner, are administered in combination with other compounds that are active against endoparasites, the invention provides a method for treating or preventing an endoparasitic infection and an ectoparasitic infestation in and on an animal. The method comprises administering a composition comprising an effective amount of a compound of formula (I), IA or afoxolaner enriched in the (S)-enantiomer in combination with an effective amount of at least a second active agent, or pharmaceutically acceptable salts thereof, to the animal.

Mammals which can be treated include but are not limited to humans, cats, dogs, cattle, chickens, cows, bison, deer, goats, horses, llamas, camels, pigs, sheep and yaks. In one embodiment of the invention, the mammals treated are humans, cats or dogs.

In one embodiment of the invention, the compositions of the invention comprising a compound of formula (I) or IA enriched in the (S)-enantiomer in combination with an additional compound that is active against endoparasites are effective against endoparasites that are resistant to active agents of the macrocyclic lactone class. In one embodiment, the compounds and compositions of the invention are effective for controlling *Haemonchus contortus*, *Ostertagia circumcincta* and *Trichostrongylus colubriformis* in mammals or birds.

In another embodiment, the invention provides a method for treating an parasitic infestation and/or infection in an animal, comprising administering an effective amount of a compound of formula (I) or IA enriched in the (S)-enantiomer, including (S)-afoxolaner, in combination with an effective amount of activators of invertebrate GABA receptors, including an avermectin or milbemycin, to the animal in need thereof. Avermectins that may be used in combination with the compounds of the invention include, but are not limited to abamectin, dimadectin, doramectin, emamectin, eprinomectin, ivermectin, latidectin, lepimectin, and selamectin. Milbemycins compounds that may be used in combination with the compounds of the invention include, but are not limited to, milbemectin, milbemycin D, milbemycin oxime, moxidectin and nemadectin. Also included are the 5-oxo and 5-oxime derivatives of said avermectins and milbemycins.

In one embodiment for the treatment against ectoparasites, the ectoparasite is from the genera *Ctenocephalides*, *Rhipicephalus*, *Dermacentor*, *Ixodes*, *Amblyomma*, *Haemaphysalis*, *Hyalomma*, *Sarcoptes*, *Psoroptes*, *Otodectes*, *Chorioptes*, *Hypoderma*, *Damnalinia*, *Linognathus*, *Haematopinus*, *Solenoptes*, *Trichodectes*, and *Felicola*. The ectoparasites treated include but are not limited to fleas, ticks, mites, mosquitoes, flies, lice, blowfly and combinations thereof. Specific examples include but are not limited to cat and dog fleas (*Ctenocephalides felis*, *Ctenocephalides* spp. and the like), ticks (*Rhipicephalus* spp., *Ixodes* spp., *Dermacentor* spp., *Amblyomma* spp. and the like), and mites (*Demodex* spp., *Sarcoptes* spp., *Otodectes* spp. and the like), lice (*Trichodectes* spp., *Cheyletiella* spp., *Linognathus* spp., and the like), mosquitoes (*Aedes* spp., *Culex* spp., *Anopheles* spp., and the like) and flies (*Haematobia* spp., *Musca* spp., *Stomoxys* spp., *Dermatobia* spp., *Cochliomyia* spp., and the like). In yet another embodiment for the treatment against ectoparasites, the ectoparasite is a flea and/or tick.

Additional examples of ectoparasites that may be controlled with the compounds of formula (I) and IA enriched in the (S)-enantiomers, include, but are not limited to, the tick *Rhipicephalus microplus* (cattle tick), *Rhipicephalus decoloratus* and *Rhipicephalus annulatus*; myiasis such as *Dermatobia hominis* and *Cochliomyia hominivorax* (greenbottle); sheep myiasis such as *Lucilia sericata*, *Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In one embodiment, when administered with another compound that is active against endoparasites, the compounds and compositions of the invention may be used for treating or preventing an endoparasitic infection of the following parasite: *Anaplocephala* (*Anoplocephala*), *Ancylostoma*, *Necator*, *Ascaris*, *Brugia*, *Bunostomum*, *Capillaria*, *Chabertia*, *Cooperia*, *Cyathostomum*, *Cylicocyclus*, *Cylicodontophorus*, *Cylicostephanus*, *Craterostomum*, *Dictyocaulus*, *Dipetalonema*, *Dipylidium*, *Dirofilaria*, *Dracunculus*, *Echinococcus*, *Enterobius*, *Fasciola*, *Filaroides*, *Habronema*, *Haemonchus*, *Metastrongylus*, *Moniezia*, *Necator*, *Nematodirus*, *Nippostrongylus*, *Oesophagostomum*, *Onchocerca*, *Ostertagia*, *Oxyuris*, *Parascaris*, *Schistosoma*, *Strongylus*, *Taenia*, *Toxocara*, *Strongyloides*, *Toxascaris*, *Trichinella*, *Trichuris*, *Trichostrongylus*, *Triodontophorus*, *Uncinaria*, *Wuchereria*, and combinations thereof. In another embodiment of the invention, the parasite is *Haemonchus contortus, Ostertagia circumcincta, Trichostrongylus axei, Trichostrongylus colubriformis, Cooperia curticei, Nematodirus battus, Dirofilaria immitis*, and combinations thereof.

Non-Veterinary Uses and Methods

Due to their excellent activity, the compounds of formula (I) enriched in the (S)-enantiomer, and in particular compounds of formula IA wherein $X^1$, $X^2$ and $X^3$ are H, chloro, fluoro or $CF_3$, including (S)-afoxolaner, may be used for controlling pests that harm crops, plants and material made from wood. Accordingly, the present invention also provides a method for controlling animal pests, which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula (I), formula IA wherein $X^1$, $X^2$ and $X^3$ are H, chloro, fluoro or $CF_3$, including (S)-afoxolaner, or a salts thereof, or a composition comprising the compounds.

In one embodiment, the method of the invention serves for protecting plant propagation material (such as seed) and the plant which grows therefrom from animal pest attack or infestation and comprises treating the plant propagation material (such as seed) with a pesticidally effective amount of a compound of formula (I), formula IA wherein $X^1$, $X^2$ and $X^3$ are H, chloro, fluoro or $CF_3$, including (S)-afoxolaner, or an agriculturally acceptable salts thereof as defined above, or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In one embodiment of the present invention related to agricultural applications, "animal pests" refer to arthropods and nematodes, more preferably from harmful insects, arachnids and nematodes, and even more preferably from insects, acarids and nematodes.

EXAMPLES

The invention is further described by the following non-limiting examples which further illustrate the invention, and are not intended, nor should they be interpreted to, limit the scope of the invention.

All temperatures are given in degrees Centigrade; room temperature means 20 to 25° C. Reagents were purchased from commercial sources or prepared following literature procedures. Chiral purity is determined by HPLC analysis using a chiral column. Reference to the volume of a solvent or reagent are based on the volume of the starting material using the density of 1 g/mL.

Bn=benzyl
DCM=dichloromethane
DMF=dimethylformamide
ACN=acetonitrile
eq=molar equivalents
HPLC=high pressure liquid chromatography
PE=petroleum ether
Red-Al=sodium bis(2-methoxyethoxy)aluminum hydride
rt=room temperature
TEA=triethylamine
THF=tetrahydrofuran
min.=minutes
h=hours
vol=volume of solvent relative to the volume of the starting material, calculated assuming a density of 1 gram/milliliter.

Example 1: Preparation of Catalyst

The chiral phase transfer catalyst of formula (IIIa-13-1a) was prepared according to one embodiment shown in scheme 2 below:

Scheme 2

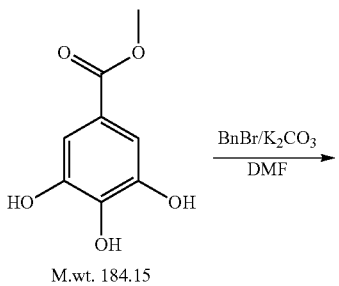

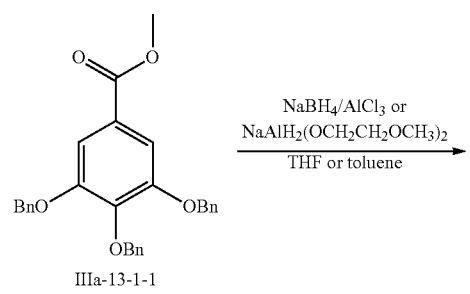

IIIa-13-1-1

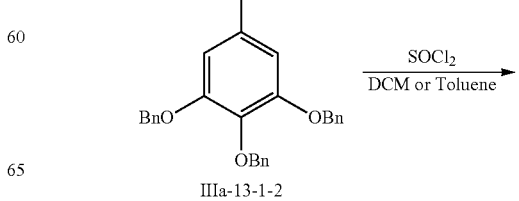

IIIa-13-1-2

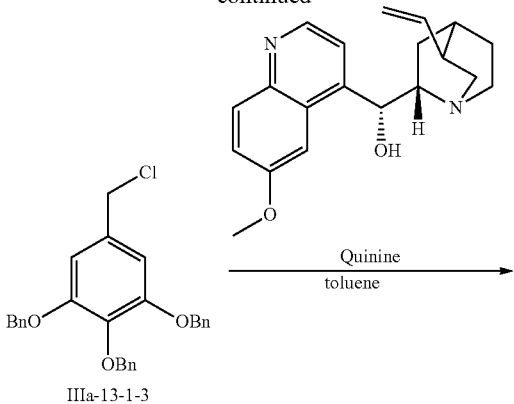

Step 1 Synthesis of IIIa-13-1-1

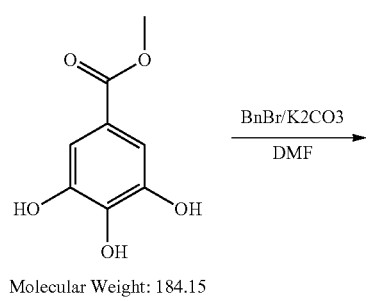

Molecular Weight: 184.15

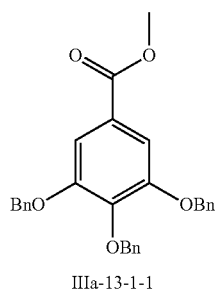

IIIa-13-1-1

1. Charge dimethylformamide (DMF, 7.0 L, 10 volumes) to a 20 liter 4-neck flask.
2. Charge the starting material (700.0 g, 1.0 eq) to the flask.
3. Charge $K_2CO_3$ (2622.9 g, 5.0 eq) to the flask.
4. BnBr (2250.3 g, 3.5 eq) is added dropwise to the mixture at 0~20° C.
5. The reaction mixture is heated to 60±5° C.
6. Stir reaction mixture for 12 hours at 60±5° C.
7. The reaction is monitored until the content of starting material≤0.5%.
8. Pour the reaction mixture to 25.0 L of ice water.
9. Stir for 2 hours at 20±5° C.
10. Filter the product (solid) and wash the filter cake with 5.0 L water.
11. Dry the product under vacuum at 60° C.
12. After drying, 1500 g of the product is obtained. The purity of the product by HPLC is 99.0% and the yield is 88.0%.

Step 2: synthesis of IIIa-13-1-2

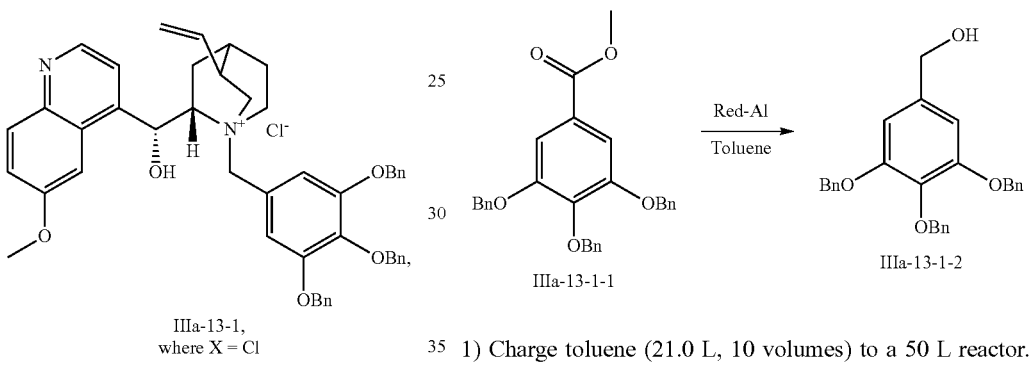

1) Charge toluene (21.0 L, 10 volumes) to a 50 L reactor.
2) Charge IIIa-13-1-1 (2045 g, 1.0 eq.) to the reactor.
3) Cool the mixture to 0~10° C.
4) Sodium bis(2-methoxyethoxy)aluminum hydride (Red-Al, 3000 g, 2.3 eq.) is added dropwise into the mixture at 0~10° C. with stirring.
5) The reaction mixture is stirred for 5 h at 15-20° C.
6) The reaction is monitored by HPLC until the content of starting material≤0.5%.
7) Once the conversion is complete (≤0.5% starting material) the reaction mixture is poured into 20.0 L of 10% NaOH at 10~20° C.
8) The resulting mixture is stirred for 2 h at 10~15° C. and then filtered through a bed of diatomaceous earth (e.g. Celite).
9) The filter cake is washed with 10.0 L ethyl acetate and the washes are combined with the filtrate.
10) The combined organic phase filtrate is washed with water (10 L) and brine (5.0 L) one time each.
11) The organic phase is concentrated to about 2 volumes.
12) The concentrated organic phase is then diluted with petroleum ether (PE, 20 L).
13) The diluted organic phase is re-concentrated to about 2 volumes and then filtered.
14) The filter cake is washed with 5.0 L of PE and then dried under vacuum at 30-40° C. to yield 1660 g of IIIa-13-1-2 (86.0% yield) in a purity of 98.7%.

Step 3 Synthesis of IIIa-13-1-3

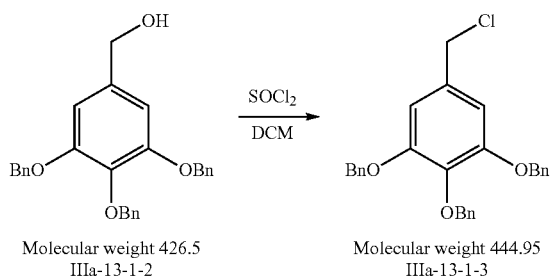

Molecular weight 426.5
IIIa-13-1-2

Molecular weight 444.95
IIIa-13-1-3

1) Charge dichloromethane (DCM, 29.0 L, 10 volumes) to a 50 L reactor.
2) Charge IIIa-13-1-2 (2.9 kg, 1.0 eq.) to the 50 L reactor and cool down to about −5 to 0° C.
3) Charge $SOCl_2$ (900 g, 1.1 eq.) to the reactor at −5~0° C.
4) Stir reaction mixture for 5 h at −5~5° C.
5) The extent of the reaction is monitored by TLC until complete.
6) Concentrate the mixture to 2 volumes.
7) Diluted the residue with PE (20 L).
8) Re-concentrate the mixture to 2 volumes.
9) Diluted the concentrated residue with PE (20 L).
10) Re-concentrate the mixture to 2 volumes.
11) Filter the mixture and wash the filter cake with PE (5.0 L).
12) Dry the filter cake under vacuum at 30-40° C. to obtain 2.9 kg of the product (93.0% yield).

Step 4 Synthesis of IIIa-13-1

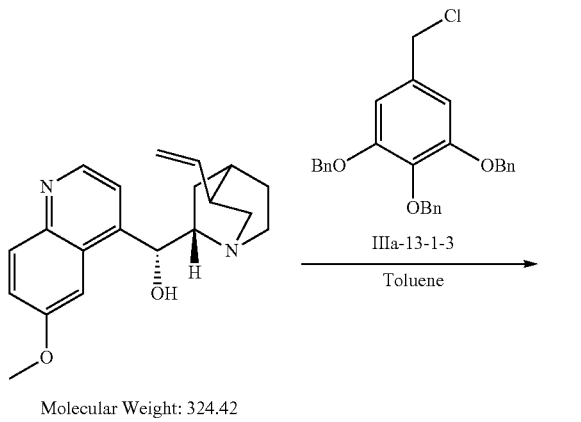

Molecular Weight: 324.42

IIIa-13-1
Molecular Weight: 769.37

1) Charge toluene (15 L, 10 volumes) to a 50 L four-neck flask.
2) Charge quinine (1500 g, 1.0 eq.) to the reactor.
3) Charge IIIa-13-1-3 (2472 g, 1.2 eq.) to the reactor.
4) Stir the reaction mixture for 12 h at 60-65° C.
5) The reaction is monitored by HPLC until the content of starting material is ≤2.0%.
6) Once the reaction is complete by HPLC, cool down the mixture to 25~35° C.
7) Filter the reaction mixture and wash the filter cake with 10.0 L of toluene.
8) Dry the product under vacuum at 40~45° C. to obtain the desired product (2.4 kg, purity 94.9%, 67.5% yield).

The proton NMR spectra and the LCMS of the product are consistent with the structure of IIIa-13-1. FIG. 1 shows the $^1H$ NMR spectra of the product in DMSO-$d_6$ and FIG. 2 shows the LCMS of the product. The purity of the product by HPLC analysis was 94.9% by area and the chiral purity by chiral HPLC was 100% by area.

Example 2: Alternate Process for Preparation of Chiral Phase Transfer Catalyst IIIa-13-1

An alternate process according to Scheme 2 was used to prepare the catalyst of formula IIIa-13-
Step 1 Synthesis of IIIa-13-1-1
1. 3,4,5-trihydroxybenzoate (9.6 kg, 1.0 eq.) and DMF (76.8 liters) are charged to a reactor at 10-25° C.
2. To the reactor is charged $K_2CO_3$ (25.1 kg, 3.5 eq.) at the same temperature.
3. Benzyl bromide (28.4 kg, 3.2 eq.) is then added slowly to the mixture at a temperature of from 20-45° C. and the mixture aged at about 60° C. for about 4 hours.
4. Analysis of the reaction mixture shows that ≤1.0% of the starting material is left.
5. The solids are filtered off and the cake washed with DMF twice (1 vol.).
6. The filtered solution and wash is added to water (115 liters) at 5° C. and the mixture stirred for 2 hours at 5-15° C.
7. The resulting mixture was filtered and the cake washed with water.
8. The isolated solid was dried for 12 hours under vacuum at 45° C. to obtain the product (22.6 kg as an off-white solid.
9. In this alternate process IIIa-13-1-1 is obtained as an off-white solid with 99.4% purity in a 95.4% yield.

Step 2: Synthesis of IIIa-13-1-2
1. Tetrahydrofuran (177.6 liters) is charged to a reactor and $AlCl_3$ (6.5 kg, 1.0 eq.) is charged at 10-15° C.
2. To the resulting mixture is charged compound IIIa-13-1 (22.2 kg, 1.0 eq.) and then $NaBH_4$ (1.78 kg, 1.0 eq.) at 10-25° C.
3. The resulting reaction mixture is aged for 10 hours at 20-30° C. and then additional $NaBH_4$ is charged (1.78 kg, 1.0 eq.) and the mixture stirred for an additional 12 hours.

4. A further 2 equivalents of NaBH$_4$ are charged with subsequent aging of the reaction mixture (12-14 hours) at which time HPLC analysis shows that ≤2.5% of the starting material remains.
5. The reaction mixture is cooled to about 15° C. and water is added slowly (55.5 liters).
6. After addition of water, 2 M HCl is added to the mixture and the resulting mixture stirred for a suitable amount of time at 20° C.
7. The layers are settled, the organic layer is separated and the aqueous layer back-extracted with ethyl acetate.
8. The combined organic layers are washed with 6% NaHCO$_3$ and then 20% brine.
9. The combined organic layer and wash is then concentrated to about 2.5 volumes under vacuum at 40-50° C. and heptane is charged (about 67 liters).
10. The mixture is further concentrated to about 3 volumes under vacuum.
11. The mixture is filtered and the cake washed with heptane.
12. The cake is dried under vacuum at 35-45° C. to obtain 20.1 kg of IIIa-13-1-2 as an off-white sold in 97.5% yield and 96.5% purity.

Step 3 Synthesis of IIIa-13-1 without Isolation of IIIa-13-1-3
1. Toluene (148 liters, 10 vol.) and IIIa-13-1-2 (18.5 kg, 1.0 eq.) are charged to a reactor and cooled to about 15° C.
2. SOCl$_2$ (5.27 kg, 1.03 eq.) is charged and the resulting mixture is stirred for 3 hours.
3. After confirmation that the reaction is complete, water (111 liters, 6 vol.) is added to the reaction mixture slowly.
4. The layers are allowed to settle and the organic layer separated.
5. The organic layer is then washed with NaHCO$_3$ (8%) and then K$_2$HPO$_4$ (5%).
6. The washed organic layer is then washed twice with water and then with 20% brine twice.
7. To the washed organic layer is added Quinine (11.3 kg, 0.8 eq.) at 15-25° C. and the mixture stirred for 24 hours at 60° C., after which HPLC analysis shows ≤5% of Quinine remaining.
8. The mixture is cooled to 10° C. slowly and then stirred further at this temperature for about 2 hours.
9. The mixture is filtered and the solid washed with toluene twice and then dried under vacuum at 40° C. for 12 hours to obtain 20.1 kg of the IIIa-13-1 as an off-white solid in 79.4% yield and 96.6% purity by HPLC.

The $^1$H NMR and LCMS spectra of the product were found to be consistent with the structure of the desired product.

Enantiomerically enriched isoxazoline compounds of Formula (R)-IA and (S)-IA are prepared according to Examples 3 and 4, respectively, as shown in Scheme 3 below. The stereochemistry noted in the title of the compound relates to the orientation of the quaternary carbon in the isoxazoline ring, whether shown in the chemical structure by wedges or not.

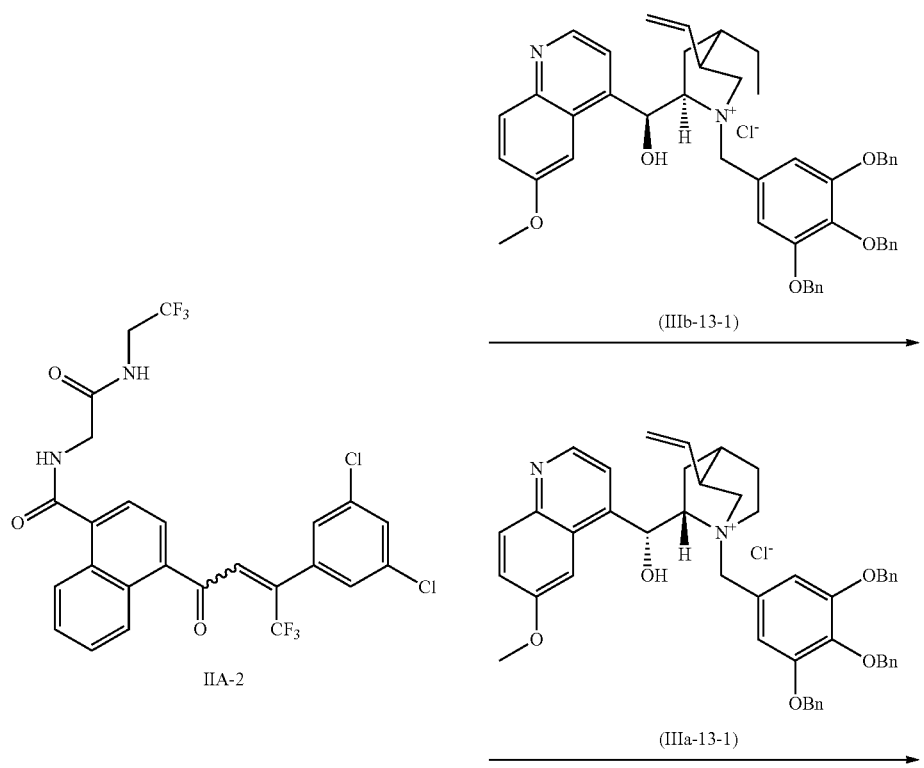

Scheme 3

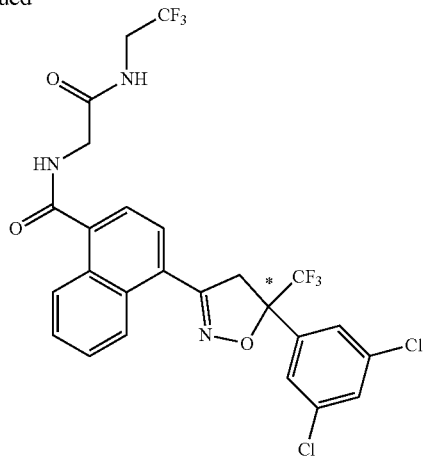
(R)-IA-2
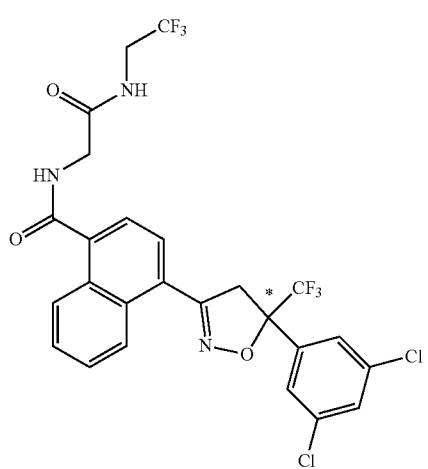
(S)-IA-2
Example 3: Synthesis of (R)-IA-2 in which the Chiral Carbon in the Isoxazoline Ring is in the (R)-Configuration
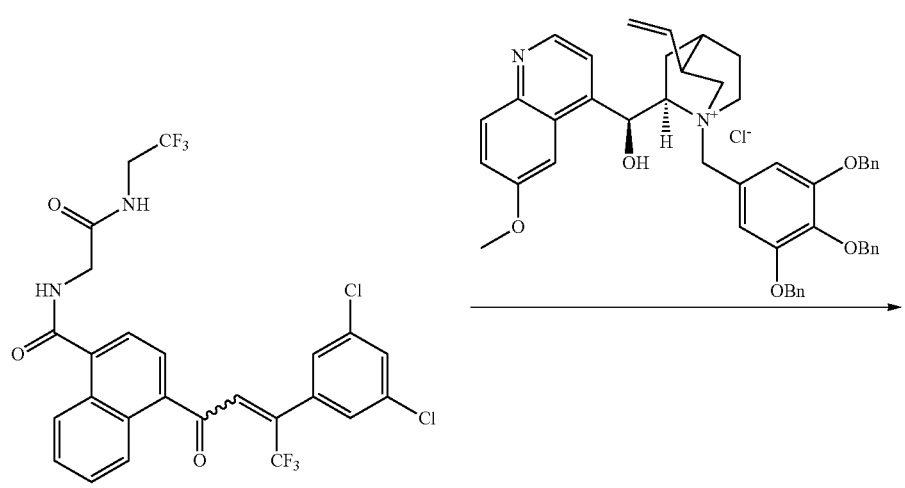

-continued

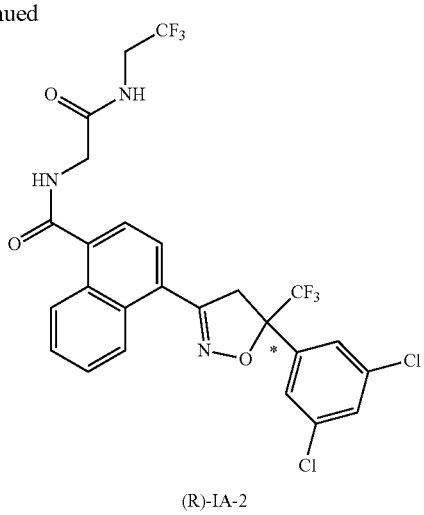

(R)-IA-2

$X^1, X^3 = Cl, X^2 = H$

1) Formula (IIA-2) (45.0 g, 1.0 eq) and dichloromethane (DCM, 1.35 L, 30 volumes) were placed into a 2 L reactor and stirred until the solid was dissolved completely.
2) The mixture was cooled to 0° C.
3) The catalyst (IIIb-13-1) was added (1.8 g, 3% mol) to the mixture.
4) The mixture was cooled to −10° C.
5) Hydroxylamine (25.7 g, 5.0 eq., 50% in water) was added to a solution of NaOH (18.7 g, 6.0 eq., in 5 volumes of water) in another reactor.
6) The solution was stirred for 30 min.
7) The hydroxylamine and NaOH solution was added dropwise to the 2 L reactor in about 4 hours.
8) The resulting mixture was stirred for 16 h at −10° C.
9) The process of the reaction was monitored by HPLC until the content of starting material was ≤1.0%.
10) When the reaction was complete, the mixture was warmed to 10° C.
11) 200 ml of water was added to the mixture and the mixture was stirred for 10 minutes.
12) The organic and aqueous phases were allowed to separate and organic layer was collected.
13) The organic layer was washed with 200 ml of 15% $KH_2PO_4$.
14) The aqueous and organic phases were allowed to separate and organic layer was collected.
15) The organic layer was further washed with 200 ml of brine and the organic layer was collected.
16) The resulting organic layer was concentrated under vacuum at 25~30° C. to about 2 volumes.
17) Toluene (450 ml, 10 volumes) was charged to the vessel and the mixture was concentrated further under vacuum at 45~50° C. to about 3 volumes. Solvent exchange into toluene was repeated twice using this procedure.
18) After exchange of the solvent to toluene, the solution was heated to 55-60° C.
19) The mixture was cooled to 40° C. over 1.5 hours and stirred at 40° C. for 3 hours.
20) The mixture was further cooled to 25° C. over 2 hours and stirred at 25° C. for 3 hours.
21) The mixture was cooled to 5~10° C. over 1 hour and stirred at 8° C. for 12 hours.
22) After aging for 12 hours at 8° C., the solid was filtered off and the cake washed with cold toluene (90 ml, 2 volumes).
23) The resulting solid was dried under vacuum at 85~90° C. for 24 h to yield the product as a white solid (24.0 g, chiral purity 98.4%, chemical purity 99.3%, yield 52.1%).

The $^1$H NMR and LCMS of the product are consistent with the structure of (R)-IA-2. Furthermore, the chiral purity of the product was verified using a chiral HPLC method using a Chiralpak IA 4.6×150 mm, 5 mm column with a mobile phase of n-hexane and isopropanol (90:10) at a temperature of 30° C. with detection at 240 nm. The flow rate is 1.0 mL/min and the sample is prepared at a concentration of 2.0 mg/mL in ethanol.

Example 4: Synthesis of (S)-IA in which the Chiral Carbon in the Isoxazoline Ring is in the (S)-Configuration

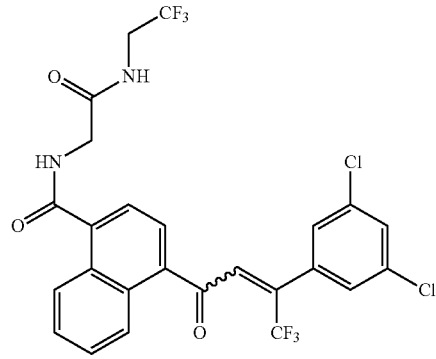

IIA-2

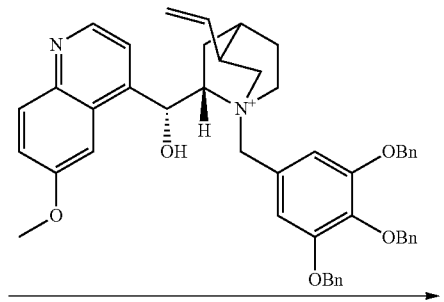

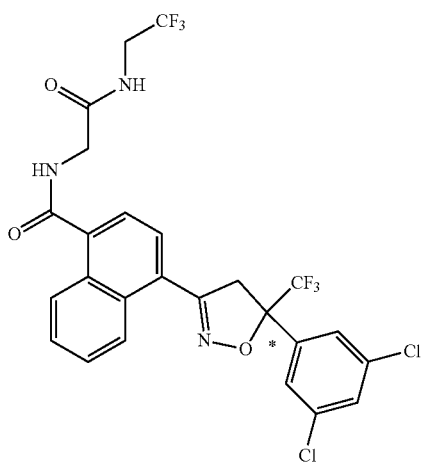

(S)-IA-2

$X^1, X^3 = Cl, X^2 = H$

1) Formula (IIA-2) (23.0 g, 1.0 eq.) and DCM (690 ml, 30 volumes) were placed into a 1 L reactor. The solid was dissolved completely.
2) The mixture was cooled to 0° C., at which time some starting material precipitated out.
3) The catalyst of formula (IIIa-13-1) (0.92 g, 3% mol) was added to the reactor and the mixture was cooled to −10° C.
4) Hydroxylamine (13.15 g, 5.0 eq., 50% in water) was added to a solution of NaOH (9.56 g, 6.0 eq., in 5 volumes of water) in another reactor.
5) The resulting solution was stirred for 30 min.
6) The hydroxylamine and NaOH solution was added drop wise to the 1 L reactor containing Formula (IIA-2) over about 3 hours.
7) The resulting mixture was stirred for 16 h at −10° C.
8) The extent of the reaction is monitored by HPLC until the content of starting material is ≤1.0%.
9) Once the reaction is complete, the mixture was warmed to 10° C. and 100 ml of water was added and the resulting mixture stirred for 10 minutes.
10) The aqueous and organic layers are allowed to separate and the organic layer was collected.
11) The organic layer was the washed with 100 ml of 5% $KH_2PO_4$, the layers allowed to separate and the organic layer collected.
12) The organic layer was washed with 100 ml brine, the layers allowed to separate and the organic layer collected.
13) The organic layer was concentrated under vacuum at 25~30° C. to about 2 volumes.
14) Toluene (230 ml, 10 volumes) was charged to the vessel and concentration under vacuum at 45~50° C. was continued to about 3 volumes. The solvent exchange process was repeated twice more.
15) Once the solvent exchange process was finished, the solution was heated to 55-60° C.
16) The mixture was then cooled to 40° C. over 1.5 hours and stirred at 40° C. for 3 hours.

17) The mixture was then cooled to 25° C. over 2 hours and stirred at 25° C. for 3 hours.
18) The mixture was then further cooled to 5~10° C. over 1 hour and stirred at 8° C. for 12 hours, at which time the solid was filtered.
19) The filter cake was washed with cold toluene (460 ml, 2 volumes) and then dried under vacuum at 85-90° C.

for 24 hours to obtain the product as a white solid (13.0 g, chiral purity: 99.0% using the chiral HPLC method described in Example 3, chemical purity: 98.7% by area (HPLC), yield: 52.1%). The $^1$H NMR and LCMS spectra are consistent with the structure of the product. Examples 5 and 6 describe the preparation of (R)-IA-3 and (S)-IA-3, respectively, as shown in Scheme 4 below.

Scheme 4

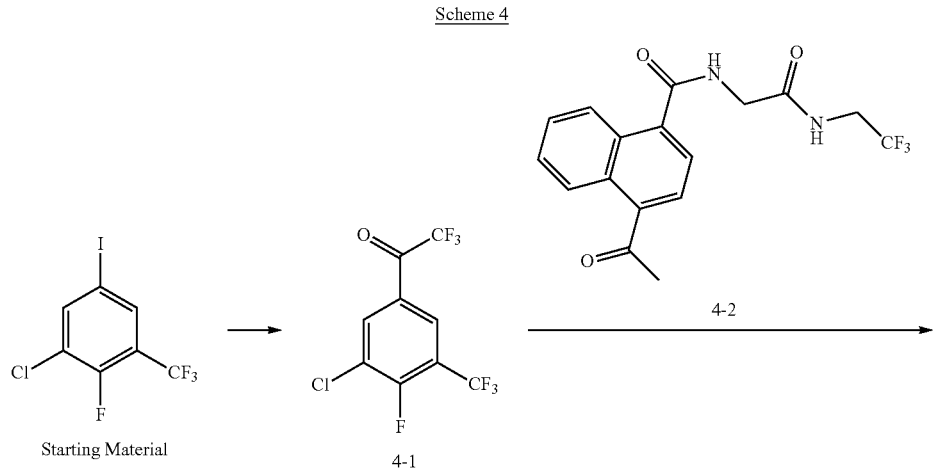

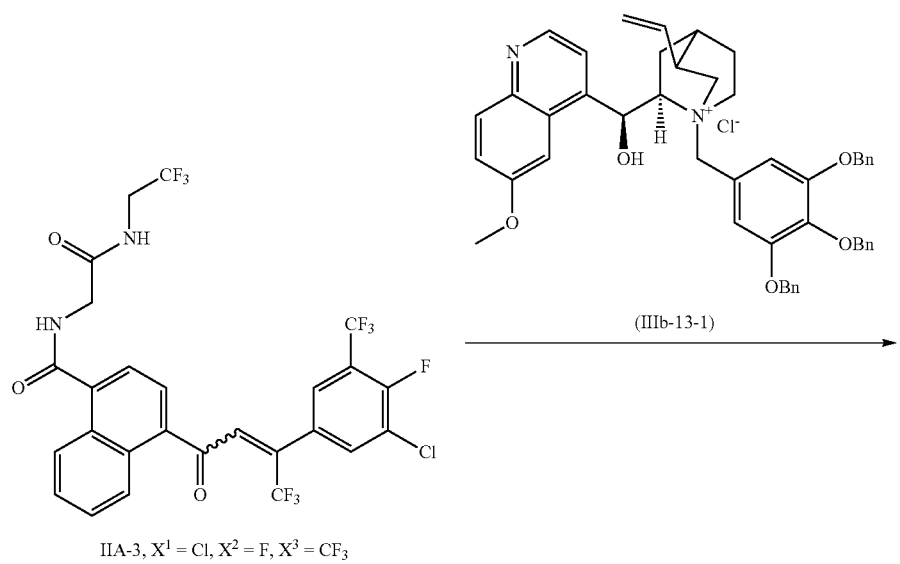

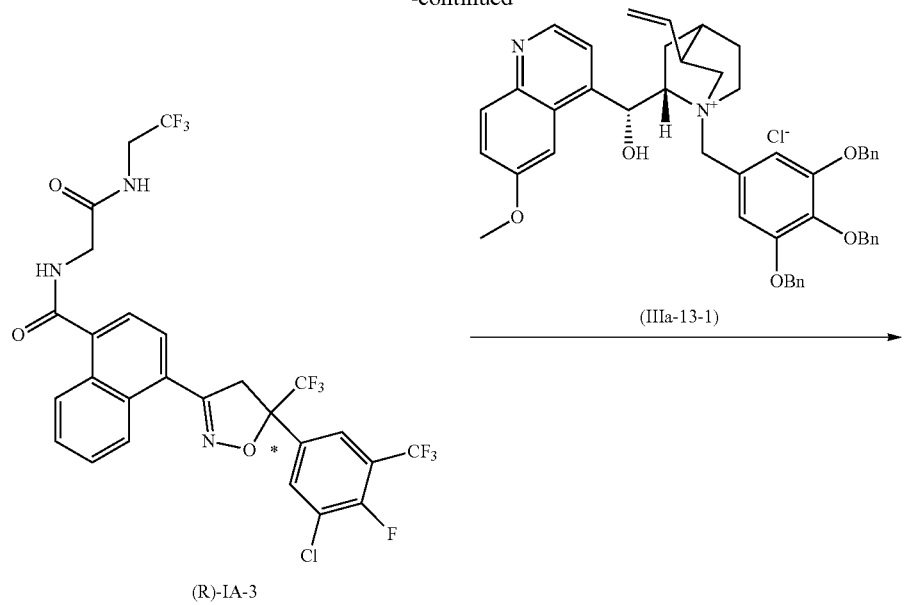
(R)-IA-3
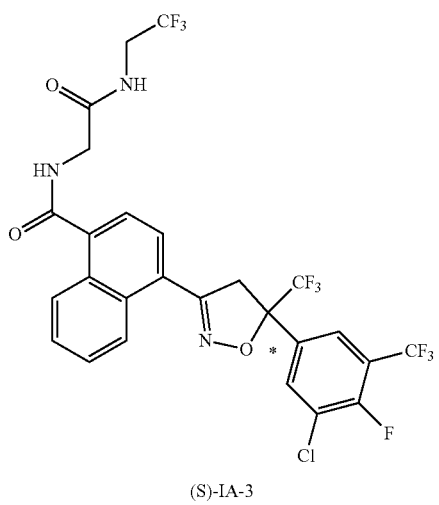 [SMILES: O=C(CNC(=O)c1ccc(C2=NOC(c3cc(Cl)c(F)c(C(F)(F)F)c3)(C(F)(F)F)C2)c2ccccc12)NCC(F)(F)F]
(S)-IA-3
Example 5: Synthesis of (R)-IA-3 Using Chiral Phase Transfer Catalyst (IIIb-13-1)
Step 1: Synthesis of Intermediate 4-2.
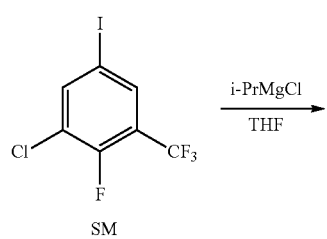
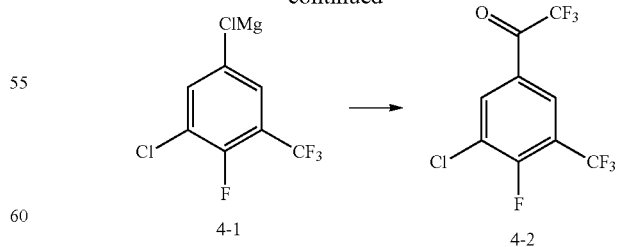
1) The substituted iodobenzene starting material (SM) (200.0 g, 1.0 eq.) and THF (400 ml, 10 volumes) were placed into a 1 L reactor and the mixture was cooled to −10 to −5° C.

2) i-PrMgCl (340 ml, 1.1 eq.) added dropwise over 1.5 hours at −10 to −5° C. to the mixture.
3) After the addition was complete, the mixture was stirred for 1 h at −10 to −5° C.
4) TLC analysis showed the complete consumption of SM (quenching sample with 1 M HCl).
5) CF₃COOMe (94.7 g, 1.2 eq.) was added over an hour at −10~−5° C. to the reaction mixture.
6) The mixture was stirred for another 12 hours −10~−5° C.
7) TLC analysis showed the almost complete consumption of intermediate 4-1 (quench with 1M HCl).
8) 1 M HCl 1000 ml was added dropwise to the reaction mixture slowly at 0~5° C. over 2 hours.
9) The reaction mixture was extracted with hexane twice (1000 ml, 500 ml).
10) Add p-toluenesulfonic acid 1.0 g to the organic layer and then the mixture was refluxed for 30 min.
11) The resulting mixture was then concentrated under vacuum at 20~25° C. to remove the hexane.
12) Sodium bicarbonate (NaHCO₃, 300 mg) was added and the mixture distilled in vacuum to afford compound 4-2 at 80~82° C., as a red liquid (85.0 grams, purity was 92.5% by HPLC, and the yield was 47.0%).

Step 2: Preparation of the Compound of Formula (IIA-3):

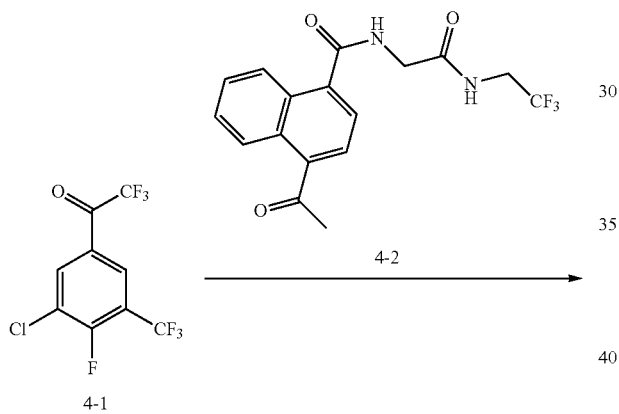

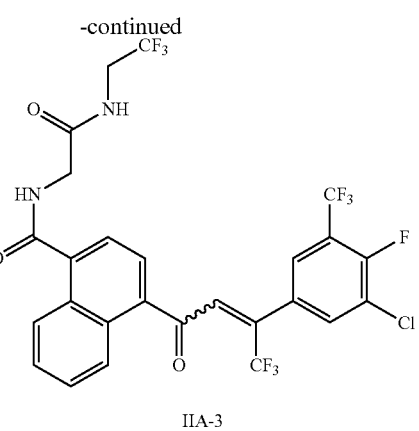

IIA-3

1) Compound 4-2 (70.0 g, 1.0 eq.) and acetonitrile (ACN, 350 ml, 5 volumes) were placed into a 1 L reactor. The solid was dissolved completely.
2) Compound 4-1 (70.2 g, 1.2 eq.) was then added to the mixture, and the mixture was heated to 90-95° C.
3) The ACN/water azeotrope was removed by distillation (b.p. 79° C.).
4) K₂CO₃ (2.0 g, 0.1 eq.) was then added to the mixture.
5) Distillation was continued to remove ACN/water at 90~95° C. for about 6 hours.
6) After this time, about 28% Compound 4-2 remained by HPLC.
7) The mixture was cooled to 15~20° C. over 1.5 hours and solid precipitated.
8) Water (50 ml) was added and then the mixture was cooled further to 0° C. over 40 min.
9) The mixture was then held at 0° C. for 40 minutes.
10) The mixture was filtered and the cake was washed with 100 ml of cold ACN/water (ACN/water, 25:6 v/v) to yield 75.0 g of a yellow solid after drying (purity: 95.1%, yield: 50.0%).

Step 3: Preparation of (R)-IA-3 Using Chiral Phase Transfer Catalyst IIIb-13-1

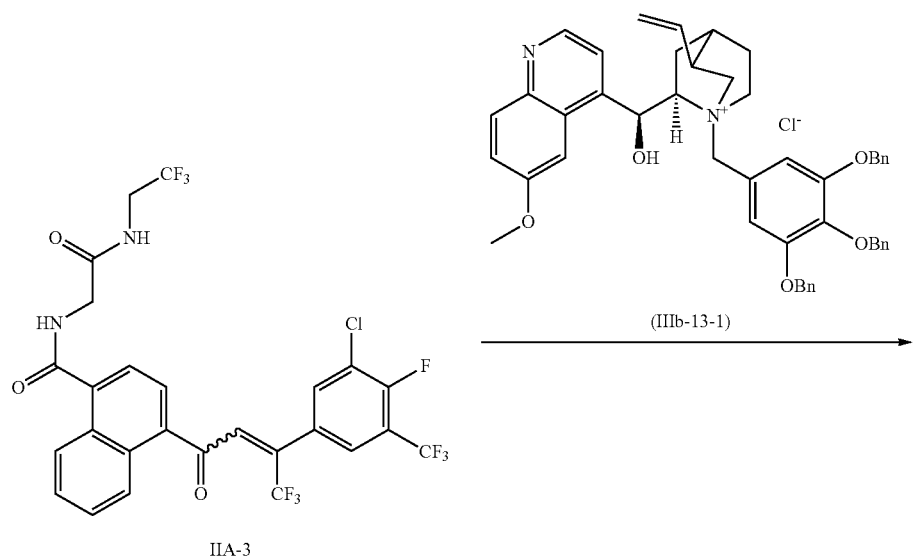

IIA-3

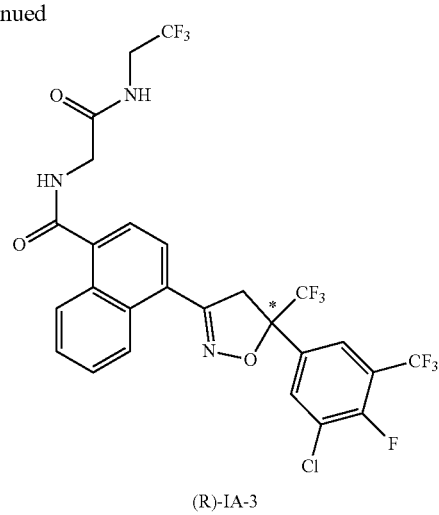

(R)-IA-3

1) The Compound of Formula IIA-3 (40.0 g, 1.0 eq.) and DCM (1.2 L, 30 volumes) were placed into a 2 L reactor; the solid was dissolved completely.
2) The mixture was cooled to 0° C. and some starting material precipitated out.
3) The catalyst of formula IIIb-13-1 (1.47 g, 3% mol) was added to the mixture and the mixture was cooled to −10° C.
4) Hydroxylamine (21.0 g, 5.0 eq., 50% in water) was added to a solution of NaOH (15.3 g, 6.0 eq., in 5 volumes of water) in another reactor and stirred for 30 minutes.
5) The hydroxylamine/NaOH solution was then added dropwise to the 2 L reactor over about 4 hours.
6) The resulting reaction mixture was stirred for 16 h at −10° C.
7) In-process samples were taken and analyzed by HPLC until the content of starting material was ≤1.0%.
8) When the reaction was complete, the mixture was warmed to 10° C. and 200 ml of water was added. The mixture was stirred for 10 minutes.
9) After mixing, the mixture was allowed to stand to separate the aqueous and organic layers and the organic layer was collected.
10) The organic layer was washed with 200 ml of 5% $KH_2PO_4$.
11) The two layers were allowed to separate and organic layer was collected.
12) The organic layer was then washed with 200 ml brine, the two layers allowed to separate and the organic layer was again collected.
13) The resulting organic layer was concentrated under vacuum at 25~30° C. to about 2 volumes.
14) Toluene (400 ml, 10 volumes) was charged to the vessel and concentration under vacuum was continued at 40~45° C. to about 3 volumes. The solvent exchange was repeated twice more using the same procedure.
15) When the solvent exchange was complete, the solution was heated to 55-60° C.
16) The mixture was then cooled to 40° C. over 1.5 hours and stirred at 40° C. for 3 hours.
17) The mixture was then cooled to 25° C. over 2 hours and stirred at 25° C. for 3 hours.
18) The mixture was finally cooled to 5~10° C. over 1 hour and stirred at 8° C. for 12 hours.
19) After this time, the mixture was filtered and the filter cake was washed with cold toluene (80 ml, 2 volumes).
20) The product was dried under vacuum at 70~75° C. for 12 h to yield a white solid (22.0 g, chiral purity: 98.0% by area using the chiral HPLC method described in Example 3, chemical purity: 97.1% by area (HPLC), yield: 48.8%). The $^1H$ NMR and LCMS spectra are consistent with the structure of the product.

Example 6: Preparation of (S)-IA-3 Using Chiral Phase Transfer Catalyst IIIa-13-1

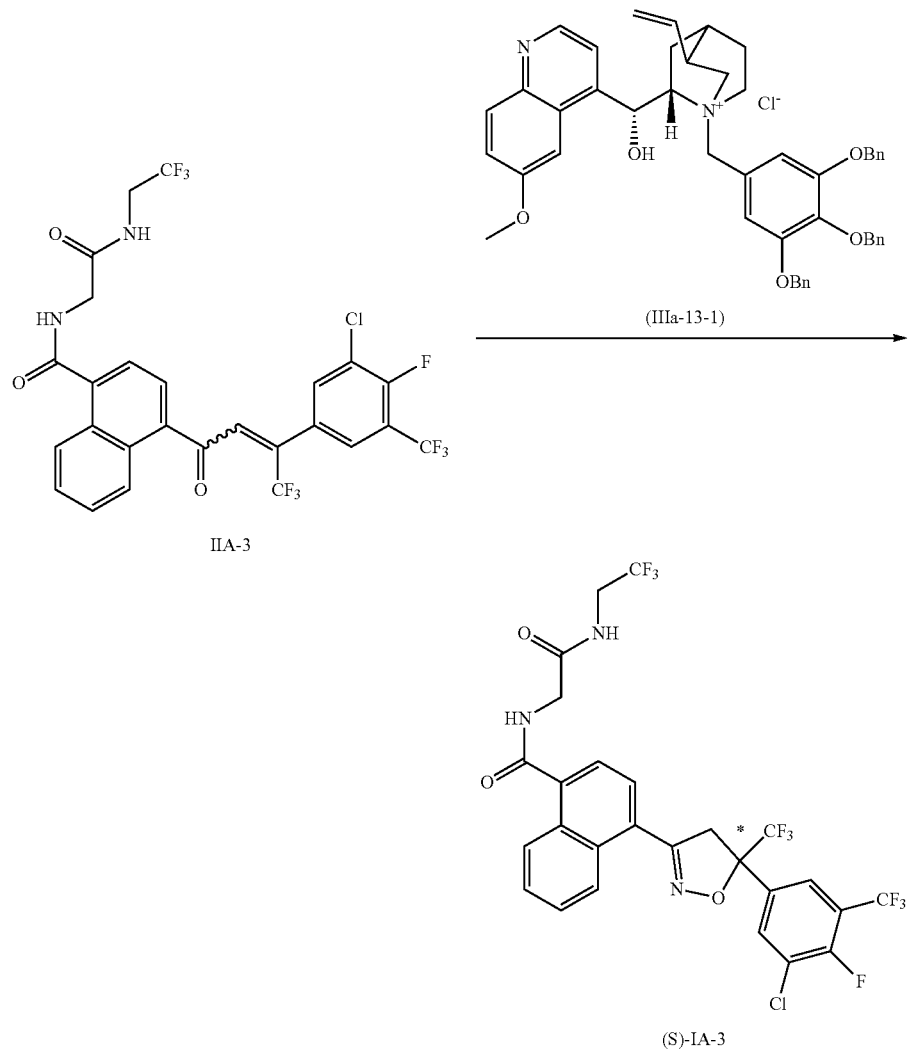

1) The compound of Formula IIA-3 (11.6 g, 1.0 eq.) and DCM 360 ml, 30 volumes) were placed into a 1 L reactor; the solid was dissolved completely.
2) The mixture was cooled to 0° C. and some starting material was precipitated out.
3) The catalyst (0.43 g, 3% mol) was added to the resulting mixture, and the mixture was cooled to −10° C.
4) Hydroxylamine (6.1 g, 5.0 eq., 50% in water) was added to a solution of NaOH (4.4 g, 6.0 eq., in 5 volumes of water) in another reactor, and the mixture was stirred for 30 minutes.
5) The hydroxylamine and NaOH solution was added dropwise to the 1 L reactor over about 2 hours, after which the mixture was stirred for 16 h at −10° C.
6) Samples were taken and analyzed by HPLC to monitor the extent of reaction until the content of starting material was ≤1.0%.
7) When the reaction was complete, the mixture was warmed to 10° C. and 50 ml of water was added. The mixture was stirred for 10 minutes.
8) The mixture was allowed to settle to separate the aqueous and organic layers and the organic layer was collected.
9) The organic layer was washed with 50 ml of 5% $KH_2PO_4$.
10) The mixture was allowed to separate and the organic layer was collected.
11) The organic layer was washed with 50 ml brine and the organic layer was again collected.
12) The organic layer was concentrated under vacuum at 25~30° C. to about 2 volumes.
13) Toluene (230 ml, 10 volumes) was charged and concentration under vacuum was continued at 40~45° C. to about 3 volumes. The solvent exchange was repeated twice more using the same procedure.
14) After the solvent exchange was complete, the solution was heated to 55-60° C.
15) The mixture was then cooled to 40° C. over 1.5 hours and stirred at 40° C. for 3 hours.
16) The mixture was cooled to 25° C. over 2 hours and stirred at 25° C. for 3 hours.

17) Finally, the mixture was cooled to 5~10° C. over 1 hour and stirred at 8° C. for 12 hours, after which the mixture was filtered.
18) The filter cake was washed with cold toluene (25 ml, 2 volumes).
19) The product was dried under vacuum at 85~90° C. for 24 h, resulting in the product as a white solid (6.8 g, chiral purity: 98.7% by area using the chiral HPLC method described in Example 3, chemical purity: 99.3% by area (HPLC), yield: 52.1%).

Example 7: Preparation of (S)-Afoxolaner Using Chiral Phase Transfer Catalyst (IIIa-13-1)

4) Hydroxylamine (64.9 g, 3.0 eq, 50% solution in water) was added to a solution of NaOH (52.5 g, 4.0 eq, in 5 v water) in a separate reactor and stirred for 30 minutes.
5) The resulting hydroxylamine/NaOH solution was then added dropwise to the 10 L reactor containing (IIA-1) over about 4 hours.
6) The resulting mixture was stirred for 12 hours at −10° C. and monitored for the extent of reaction until the amount of starting material was ≤1.0% by HPLC.
7) The mixture was then warmed to 10° C., 1 liter of water was added and the mixture was stirred for 10 minutes.
8) The mixture was allowed to settle to separate the two phases, and the organic layer was collected.

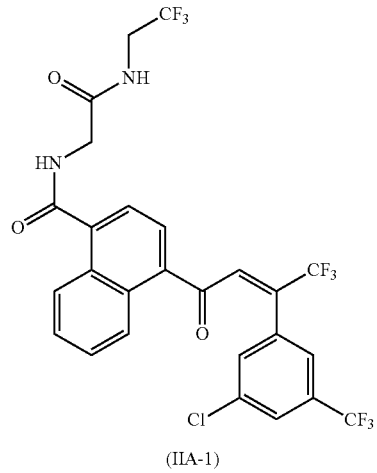

(IIA-1)

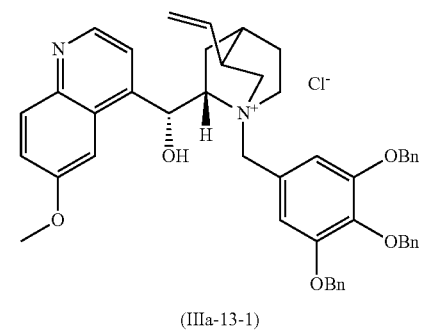

(IIIa-13-1)

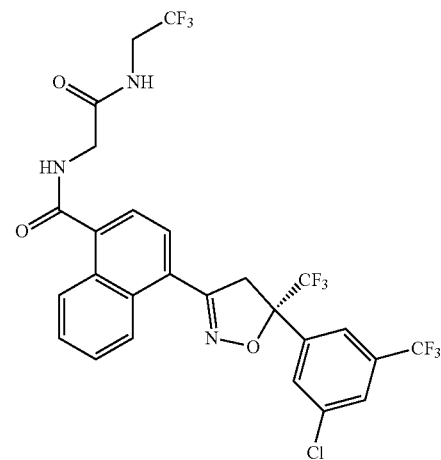

(S)-afoxolaner

1) Starting material (IIA-1) (200 g, 1.0 eq, 94.0%) and DCM (6 L, 30 volumes) were placed into a 10 L reactor, the solid was dissolved completely.
2) The mixture was cooled to 0° C., and some starting material precipitated out.
3) The catalyst (IIIa-13-1) (7.56 g, 3% mol, 95.0%) was added to the mixture and the resulting mixture cooled further to −10° C.

9) The organic layer was then washed with 2 liters of water, the layers were allowed to separate again and the organic layer was collected.
10) The organic layer was washed with 1 liter of brine, the layers allowed to separate and the organic layer was collected and dried over Na$_2$SO$_4$ (200 g).
11) The dried organic layer was concentrated under vacuum to about 2 volumes.

12) Toluene (2 L, 10 volumes) was charged to the concentrated mixture and concentration under vacuum was continued to about 5 volumes. Solvent exchange was repeated twice again.
13) The resulting solution was placed into a 2.0 L reactor and heated to 55-60° C.
14) Cyclohexane (300 ml, 1.5 volumes) was added at 55-60° C.
15) The mixture was then cooled to 40° C. over 1.5 hours and then stirred at 40° C. for 3 hours.
16) The mixture was then cooled to 25° C. over 2 hours and stirred at 25° C. for a further 3 hours.
17) The resulting mixture was cooled to 0~5° C. over 1 hour and stirred at 5° C. for 12 hours, at which time the mixture was filtered to isolate the product.
18) The filter cake was washed with cold toluene/Cyclohexane (3:1, 1000 ml, 5 volumes).
19) The product was obtained as a white solid. (171.5 g, chiral purity>99.0% by area using the chiral HPLC method described in Example 3, chemical purity>99.0% by area (HPLC), yield: 83.6%, assay purity: 92%). The $^1$H NMR and LCMS spectra are consistent with the structure of (S)-afoxolaner as the toluene solvate. FIG. 3 shows the $^1$H NMR spectra of (S)-afoxolaner in DMSO-$d_6$ and FIG. 4 shows the $^1$H NMR spectra of afoxolaner (racemic) for comparison. The chiral purity of the product was determined using the chiral HPLC method described in Example 3. FIG. 5 shows the chiral HPLC chromatogram of afoxolaner (racemic) and FIG. 6 shows the chiral HPLC chromatogram of the product (S)-afoxolaner showing one enantiomer.

Example 8: Alternate Process to Prepare (S)-Afoxolaner

An alternate process for the preparation of (S)-afoxolaner was conducted. Some of the key variations in the alternate process are noted below.

1. 1 kilogram of compound (IIA-1) (1 eq.) and 9 liters of DCM are charged to a reactor and stirred to dissolve the compound.
2. The mixture is cooled to about 0° C. and 50 grams (5 mole %) of the chiral phase transfer catalyst (IIIa-13-1) and 1 liter of DCM are charged and the resulting mixture is cooled to about −13° C.
3. A solution of 19% (w/w) hydroxylamine sulfate (294 g, 1.1 eq.) (made with 294 grams of (NH$_2$OH)H$_2$SO$_4$ and 141 grams of NaCl in 1112 mL of water) and 4.4 equivalents of NaOH as a 17.6% (w/w) solution (286 grams NaOH and 158 grams of NaCl in 1180 mL water) are charged to the reaction mixture simultaneously.
4. The resulting reaction mixture was aged about 20 hours at about −13° C. and then checked for reaction conversion by HPLC (target≤0.5% by area);
5. After completion of the reaction, water (3 vol.) was added at about 0° C. Then, a solution of 709 g of KH$_2$PO$_4$ in 4.2 liters of water are added to the mixture to adjust the pH (target 7-8) and the resulting mixture is stirred at about 20° C. for 30 minutes.
6. The layers are allowed to settle, the aqueous layer is removed and the organic layer is washed with 3 liters of water twice.

Crystallization of Toluene Solvate

1. After the extraction/washing step, the dichloromethane is removed by distillation under vacuum to about 1-2 volumes and toluene (about 5-10 volumes) is added.
2. The volume is adjusted by further distillation under vacuum and/or addition of more toluene to about 5-6 volumes. The mixture is distilled further while maintaining the volume to completely remove the dichloromethane reaction solvent.
3. The mixture is then cooled to about 10° C. and seeded with afoxolaner (racemic compound) and stirred at the same temperature for at least 2 hours;
4. The mixture is heated to about 55-65° C., aged for at least 17 hours and then the solid is filtered off. The filtered solid is washed with toluene;
5. The combined filtrate and wash is adjusted to a volume of about 5-6 volumes by distillation under vacuum and/or toluene addition;
6. The resulting mixture is cooled to about 10° C. and aged for at least 5 hours then filtered. The cake is washed with toluene.
7. The cake is dried at 50° C. under vacuum to obtain a toluene solvate of (S)-afoxolaner containing between about 6% and 8% toluene.

Re-Crystallization from Cyclohexane/Ethanol

The toluene solvate of (S)-afoxolaner was subsequently re-crystallized from a mixture of cyclohexane and ethanol to remove the associated toluene and to further purify the product.

1. 591 grams of the (S)-afoxolaner toluene solvate were charged to a vessel along with 709 mL of ethanol (1.2 vol.) and 1773 mL of cyclohexane (3 vol.) and the mixture heated to about 60° C.
2. To the resulting mixture was added an additional 6383 mL of cyclohexane with stirring.
3. The resulting mixture was cooled to about 30° C. and then heated again to 60° C. This process was repeated once.
4. The mixture was slowly cooled to 10° C. and stirred for at least 5 hours.
5. The resulting slurry was filtered and the cake washed with cyclohexane.
6. The cake was dried at 50° C. under vacuum to provide 453.7 grams of (S)-afoxolaner.

Example 9: Comparative Selectivity of Benzyloxy-Substituted Chiral Phase Transfer Catalyst (IIIa-13) with Other Cinchona Alkaloid-Based Chiral Phase Transfer Catalysts

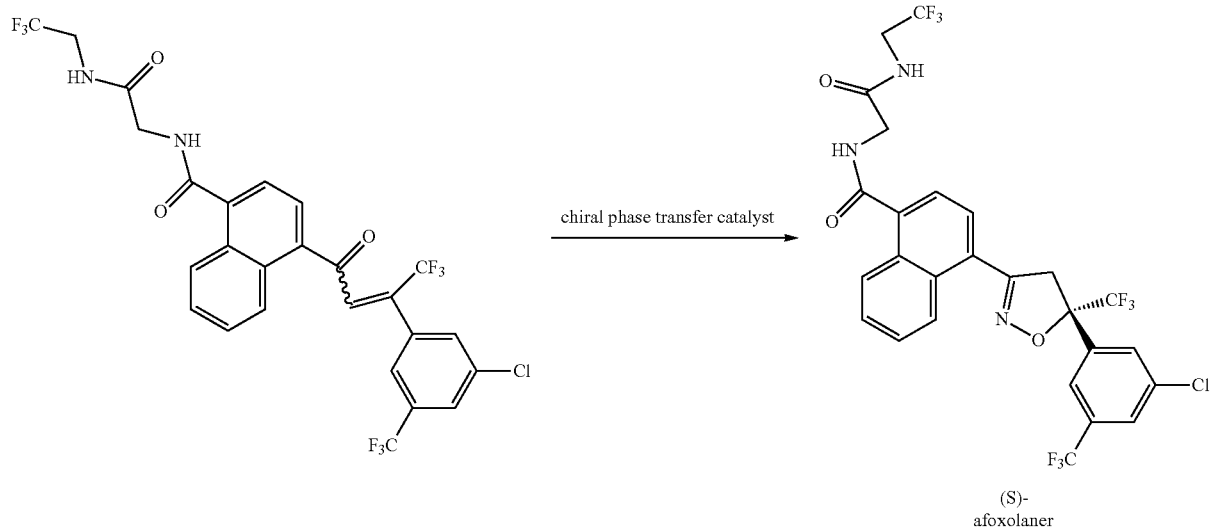 [SMILES: O=C(CNC(=O)c1ccc(C(=O)C=C(c2cc(Cl)cc(C(F)(F)F)c2)C(F)(F)F)c2ccccc12)NCC(F)(F)F ; O=C(CNC(=O)c1ccc(C2=NO[C@@](c3cc(Cl)cc(C(F)(F)F)c3)(C(F)(F)F)C2)c2ccccc12)NCC(F)(F)F]

The selectivity of the formation of (S)-afoxolaner from compound IIA-1 as shown above was studied with sixteen chiral phase transfer catalysts (PTC) of different structures. The reaction was conducted using conditions similar to those of example 7. The ratio of (S)-afoxolaner and (R)-afoxolaner in the reaction mixture was determined by chiral HPLC using the method described in Example 3. The results of the study are provided in Table 2 below.

TABLE 2

| No. | Chiral PTC | Ratio of (S)- to (R)-afoxolaner |
|---|---|---|
| 1 | (structure) | 91.5%:8.5% |
| 2 | (structure) | 62%:38% |

TABLE 2-continued
| No. | Chiral PTC | Ratio of (S)- to (R)-afoxolaner |
|---|---|---|
| 3 | 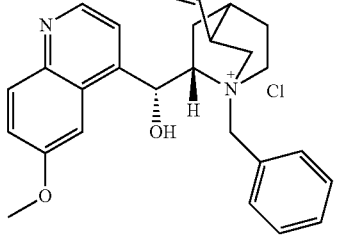 | 54%:46% |
| 4 | 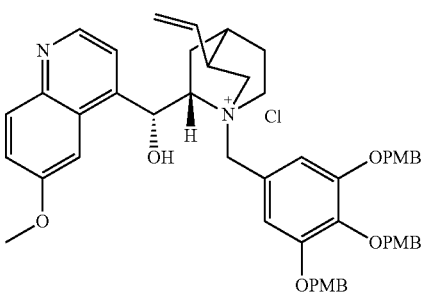<br>PMB = p-methoxybenzyl | 90%:10% |
| 5 | 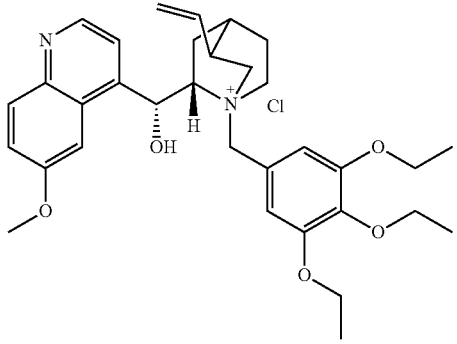 | 90%:10% |
| 6 | 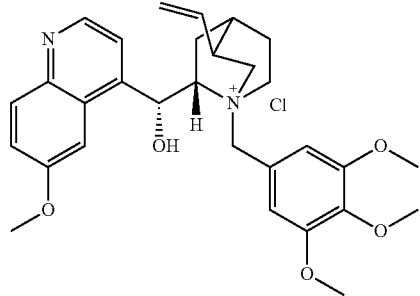 | 90%:10% |
| 7 | 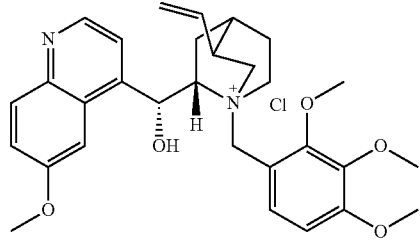 | 87%:13% |

TABLE 2-continued

| No. | Chiral PTC | Ratio of (S)- to (R)-afoxolaner |
|---|---|---|
| 8 | (cinchonidinium quaternary salt with 3,4,5-triisopropoxybenzyl group, Cl⁻) | 80%:20% |
| 9 | (cinchonidinium quaternary salt with 3,4,5-triethoxybenzyl group, Cl⁻) | 50%:50% |
| 10 | (cinchonidinium quaternary salt with 2-bromo-3,4,5-trimethoxybenzyl group, Cl⁻) | 70%:30% |
| 11 | (cinchonidinium quaternary salt with 2-chloro-3,4,5-trimethoxybenzyl group, Cl⁻) | 69%:31% |
| 12 | (cinchonidinium quaternary salt with 3,4-methylenedioxybenzyl group, Cl⁻) | 64%:35% |

TABLE 2-continued

| No. | Chiral PTC | Ratio of (S)- to (R)-afoxolaner |
|---|---|---|
| 13 | 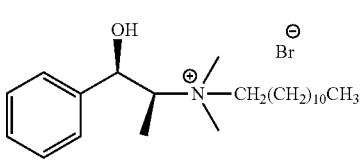 | 52%:48% |
| 14 | 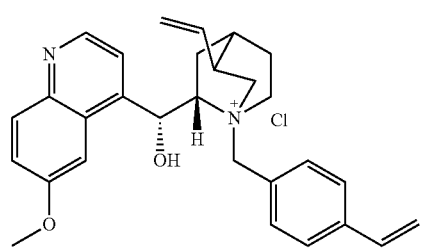 | 53%:46% |
| 15 | 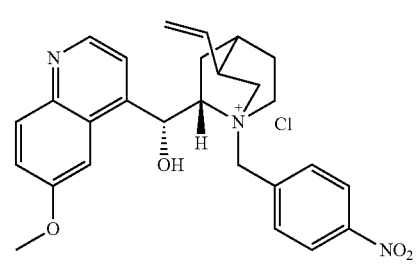 | 55%:44% |
| 16 | 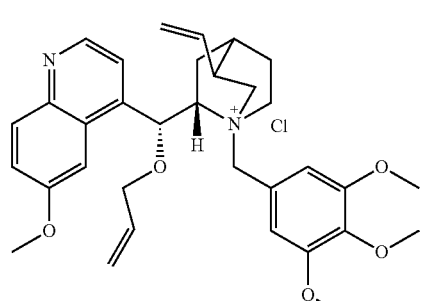 | 50%:50% |

As shown in the table, the catalyst in which the group R in the structure of formula (IIIa) is 3,4,5-tribenzyloxyphenyl results in a surprising improved selectivity for the (S)-enantiomer compared with other quinine-based phase transfer catalysts in which the group corresponding to R in formula (IIIa) is another group.

Example 10: Improvement of Chiral Purity of (S)-afoxolaner by Crystallization from Toluene A sample of reaction mixture containing a ratio (HPLC area) of 92.1:7.9, (S)-afoxolaner to (R)-afoxolaner, was concentrated to dryness and the residue was crystallized from toluene and from ethanol/cyclohexane using a process similar to that described in Example 8. The isolated crystalline solid was analyzed by chiral HPLC to determine the relative amounts of (S)-afoxolaner and (R)-afoxolaner (HPLC method: column—Chiralpak AD-3 150 mm×4.6 mm×3.0 μm, injection volume—10 μL, temperature—35° C., flow—0.8 mL/minute, mobile phase—89% hexane/10% isopropanol/1% methanol, detection—312 nm). The ratio of (S)-afoxolaner to (R)-afoxolaner in the solid isolated from the toluene crystallization was found to be 99.0:1.0 while the ratio of (S)-afoxolaner to (R)-afoxolaner in the solid crystallized from ethanol/cyclohexane was found to be 95.0:5.0.

The example shows that the crystallization (S)-afoxolaner from an aromatic solvent such as toluene results in a significant improvement of chiral purity of the product. This is very unexpected and surprising.

Example 11: Comparative Selectivity of Benzyloxy Vs. Alkoxy-Substituted Chiral Phase Transfer Catalyst of Formula (IIIa-13)

Three chiral phase transfer catalysts of Formula (IIIa-13), wherein the phenyl ring is substituted with three alkoxy groups and three benzyloxy groups (R=methyl, ethyl and benzyl); R'=OMe, W=vinyl and X=chloro were evaluated in the process to prepare of (S)-IA from compound IIA-1 as shown below.

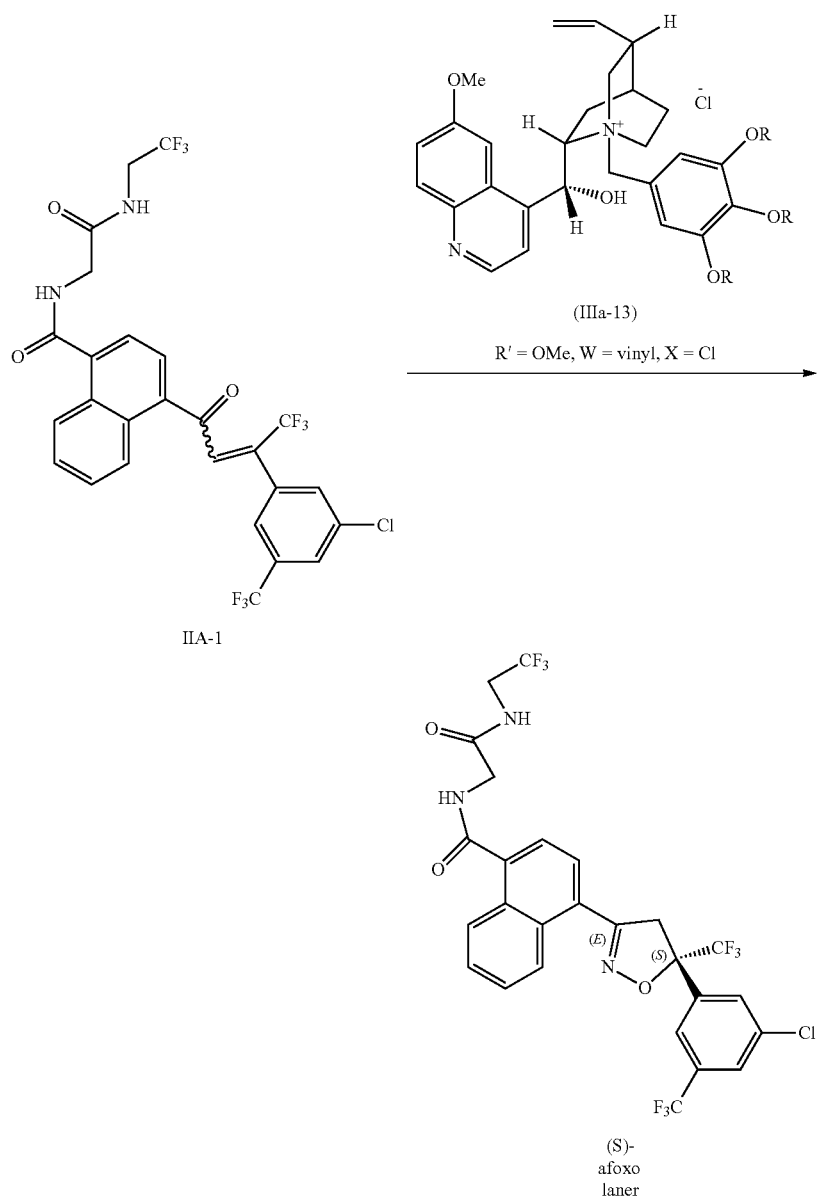

The amount of solvents and reagents and the reaction and isolation conditions were as described in Example 7 above. The same procedure was used for each catalyst tested. It was found that the selectivity of the tri-benzyloxy catalyst was surprisingly significantly better than the two alkoxy-substituted catalysts, as shown by the chiral purity of the product. Furthermore, it was found that using the tri-benzyloxy substituted phase transfer catalyst the resulting chemical purity was also much better. The superior selectivity of the benzyloxy-substituted catalyst is significant and surprising and cannot be predicted. Chiral phase transfer catalysts containing a phenyl substituted with benzyloxy and alkoxy groups were found to be superior to catalysts substituted with other groups such as electron-withdrawing groups and alkyl groups. The chiral purity and chemical purity of the product produced from the respective phase-transfer catalysts is shown in the Table 3 below:

TABLE 3

| Catalyst | Chiral Purity (S)-afoxolaner | Chemical Purity (area %) |
| --- | --- | --- |
| R = methyl | 86.4% | 97.8% |
| R = ethyl | 89.0% | 98.1 |
| R = benzyl | 99.1% | 99.6% |

Example 12: Crystallization of (S)-Afoxolaner to Make Crystalline Toluene Solvate The amount of (S)-afoxolaner shown in Table 4 in powder form was placed in a glass tube and numbered accordingly. The crystallization solvent (Table 4) was then added into the tube. The volume of crystallization solvent (see Table 4) was adjusted to obtain preferentially a suspension at room temperature and a clear solution at high temperature. The tube was then hermetically closed to prevent evaporation of the crystallization solvent and heated 1 h at high temperature (see Table 4) while the solution was vortexed at 400 rpm or stirred by a magnetic bar to dissolve the (S)-afoxolaner. To induce the crystallization of the product, the tube was then cooled at a rate and to a temperature given in Table 4. When crystals were suspected in the tube, the solution was then filtered under vacuum and the obtained solid was analyzed by X-Ray Powder Diffraction. When any crystals weren't suspected in the tube, further treatment mentioned on the Table 4 was applied on the solution before X-Ray Powder Diffraction. All Samples 1-5 were confirmed to be a crystalline toluene solvate of (S)-afoxolaner.

TABLE 4

| Sample | (S)-afoxolaner | Crystallization Solvent | High Temp | Cooling Rate | Cooling Temp | Further treatments |
|---|---|---|---|---|---|---|
| 1 | 8.0 mg | 20 µl of Toluene | 80° C. | 3°/h | 5° C. | Filtration 0.2 µm then drying 1 h at 50° C. |
| 2 | 10 mg | 200 µl of Toluene | 50° C. | 3°/h | 5° C. | Filtration 0.2 µm then drying 1 h at 50° C. |
| 3 | 10 mg | 200 µl of Toluene/ Cyclohexane (50/50 v/v) | 50° C. | 3°/h | 5° C. | Filtration 0.2 µm then drying 1 h at 50° C. |
| 4 | 10 mg | 200 µl of Toluene/ Cyclohexane (75/25 v/v) | 50° C. | 3°/h | 5° C. | Filtration 0.2 µm then drying 1 h at 50° C. |
| 5 | 30 mg | 600 µl of Toluene/ Cyclohexane (75/25 v/v | 50° C. | 3°/h | 5° C. | — |

The solid obtained from sample 2 in Table 4 was analyzed by Thermogravimetric Analysis (TGA) on a TA Instruments TGA Q500 instrument with the following parameters: atmosphere: nitrogen with 60 mL/nm flow, standard pam: TA 901670-901 not hermetic, standard lid: TA 901671-901, rate: 10° C./minute. The TGA analysis showed a loss of mass of about 10.5% from room temperature to 160° C., being particularly important in the temperature range of 70° C. to 90° C. A large loss of mass above 280° C. was associated with the decomposition of the compound. The TGA trace is shown in FIG. 7.

Analysis of the solid from sample 2 by Differential Scanning Calorimetry (DSC) was conducted on a TA Instruments Q200 apparatus using the following parameters: atmosphere: nitrogen with 60 mL/nm flow, standard pan: TA 901670-901 not hermetic, standard lid: TA 901671-901, rate: 10° C./minute. The thermal profile shows a large and narrow endothermic peak between 70° C. and 90° C. The DSC profile is shown in FIG. 7.

The solid isolated from sample 2 was analyzed by X-Ray Powder Diffraction using the following equipment and conditions: Apparatus: Bruker D8-Advance diffractometer, type: Bragg-Brentano; source CuKα$_1$, λ=1.5406 Å and CuKα$_1$, λ$_2$=1.54439 Å; generator: 35 kV-40 mA; detector: Lynx Eye; Anton Paar TTK450 chamber; Si sample holder; Angle range: 2° to 400 in 2-theta Bragg; variable divergence slit: 4 mm (V4); step size: 0.041°; step time: 1 s. FIG. 8 shows the X-Ray Powder Diffraction pattern of the solid form. Table 6 below provides the degrees 2-theta peaks identified from the analysis.

TABLE 6

| Angle 2-Theta ° | d value Angstrom | Intensity Count | Intensity % |
|---|---|---|---|
| 4.859 | 18.17219 | 2531 | 100 |
| 8.516 | 10.37469 | 1375 | 54.3 |
| 8.823 | 10.01388 | 457 | 18.1 |
| 9.735 | 9.07796 | 298 | 11.8 |
| 10.778 | 8.20182 | 729 | 28.8 |
| 11.644 | 7.59373 | 272 | 10.7 |
| 12.161 | 7.27189 | 566 | 22.4 |
| 12.746 | 6.93963 | 1029 | 40.7 |
| 14.591 | 6.06596 | 654 | 25.8 |
| 15.136 | 5.84883 | 450 | 17.8 |
| 16.694 | 5.30627 | 538 | 21.3 |
| 16.999 | 5.21182 | 930 | 36.7 |
| 17.616 | 5.03058 | 493 | 19.5 |
| 18.411 | 4.81508 | 1113 | 44 |
| 18.838 | 4.70694 | 1403 | 55.4 |
| 19.54 | 4.53941 | 725 | 28.6 |
| 19.894 | 4.45942 | 1073 | 42.4 |
| 20.937 | 4.23955 | 383 | 15.1 |
| 21.484 | 4.13274 | 645 | 25.5 |
| 21.859 | 4.06265 | 1141 | 45.1 |
| 22.236 | 3.99476 | 1497 | 59.1 |
| 22.985 | 3.86627 | 657 | 26 |
| 23.431 | 3.79365 | 998 | 39.4 |
| 24.540 | 3.62465 | 466 | 18.4 |
| 25.291 | 3.51867 | 1218 | 48.1 |
| 25.643 | 3.4711 | 1367 | 54 |
| 26.359 | 3.37852 | 393 | 15.5 |
| 27.143 | 3.28268 | 625 | 24.7 |
| 28.472 | 3.13235 | 417 | 16.5 |
| 29.223 | 3.05358 | 425 | 16.8 |
| 29.776 | 2.99809 | 425 | 16.8 |
| 30.638 | 2.91563 | 449 | 17.7 |
| 32.865 | 2.72303 | 314 | 12.4 |
| 33.120 | 2.70265 | 300 | 11.9 |
| 33.782 | 2.65114 | 358 | 14.1 |
| 34.529 | 2.5955 | 402 | 15.9 |
| 37.046 | 2.42474 | 348 | 13.7 |
| 38.405 | 2.342 | 364 | 14.4 |
| 39.648 | 2.27137 | 358 | 14.1 |

Example 13: Single Crystal X-Ray Diffraction

A single crystal X-ray diffraction analysis was conducted on a crystal of toluene solvate produced by crystallization of (S)-afoxolaner made by the process of the invention according to Examples 7 and 8. The crystal structure of (S)-afoxolaner was solved and refined to a final R factor of 5.5%. The structure was found to be a triclinic which contains two independent molecules of (S)-afoxolaner and two toluene molecules. The crystal structure was found to be strongly disordered as shown in FIG. 9. Table 7 below describes some information describing the crystal and molecular structure. According to the molecular simulation program Cerius2, the absolute configuration of the toluene solvate prepared by the process of the invention is (S). The structure of the molecular structure obtained from the Cerius2 software is shown in FIG. 10.

TABLE 7

Crystal Structure Parameters

| | |
|---|---|
| Chemical Formula | $C_{33}H_{25}ClF_9N_3O_3$ |
| Volume | 1561.42 Å$^3$ |
| Crystal System | Triclinic |
| Space Group | P1 |
| a | 8.2010 Å |
| b | 10.7031 Å |
| c | 18.6462 Å |
| α | 75.6862° |
| β | 84.2126° |
| γ | 80.592° |
| Density (g/cm$^3$) | 1.497 |
| R indices | 5.5% |
| Absolute Structure Parameter | −0.03 |
| Molecules per cell | 2 |
| Theta range for data collection | 1.98° to 26.44° |

The invention is further described by the following numbered paragraphs:

1. A process for the preparation of an isoxazoline compound of the formula (I) below, which is enriched in one enantiomer:

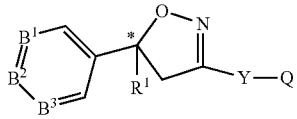

wherein:
B$^1$, B$^2$, B$^3$, are each independently C—R or N;
each R is independently H, halogen, cyano, —NO$_2$, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino or alkoxycarbonyl;
R$^1$ is C$_1$-C$_3$alkyl or C$_1$-C$_3$haloalkyl;
Y is an optionally substituted phenylene, naphthylene, indanylene, a 5- or 6-membered heteroarylene or an 8-10-membered fused heterobicyclylene, wherein the optional substituents are selected from the group consisting of halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN or —NO$_2$ and NH$_2$—C(=S)—;
Q is T-NR$^2$R$^3$, the group (—CH$_2$—)(—CH$_2$—)N—R$^3$, OH, NH$_2$, alkoxy, haloalkoxy, alkylamino, haloalkylamino, dialkylamino, halodialkylamino, thiol, alkylthio, haloalkylthio, alkylsulfinyl, haloalkylsulfinyl, alkylsulfonyl, haloalkylsulfonyl, or an optionally substituted 5- or 6-membered carbocyclyl, heterocyclyl or heteroaryl ring;
T is (CH$_2$)$_n$, CH(CH$_3$), CH(CN), C(=O) or C(=S);
R$^2$ is H, alkyl, alkenyl, alkynyl, cycloalkyl, alkylcycloalkyl, cycloalkylalkyl, alkylcarbonyl or alkoxycarbonyl;
R$^3$ is H, OR$^7$, NR$^8$R$^9$ or Q$^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from R$^4$; or
R$^2$ and R$^3$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —NO$_2$ and alkoxy;
each R$^4$ is independently halogen; alkyl, cycloalkyl, alkoxy, alkylthio, haloalkylthio, alkylsulfinyl, haloalkylsulfinyl, alkylsulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —NH$_2$, —CN or —NO$_2$; or Q$^2$;
each R$^5$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —CN or —NO$_2$;
each R$^6$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN, —NO$_2$, phenyl or pyridinyl;
R$^7$ is H; or alkyl, alkenyl, alkynyl, cycloalkyl, alkylcycloalkyl or cycloalkylalkyl, each optionally substituted with one of more halogen;
R$^8$ is H, alkyl, alkenyl, alkynyl, cycloalkyl, alkylcycloalkyl, cycloalkylalkyl, alkylcarbonyl or alkoxycarbonyl;
R$^9$ is H; Q$^3$; or alkyl, alkenyl, alkynyl, cycloalkyl, alkylcycloalkyl or cycloalkylalkyl, each optionally substituted with one or more substituents independently selected from R$^4$; or
R$^8$ and R$^9$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —NO$_2$ and alkoxy;
Q$^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from R$^5$;
Q$^2$ is independently a phenyl ring or a 5- or 6-membered heterocyclic ring, each ring optionally substituted with one or more substituents independently selected from R$^6$;
Q$^3$ is a phenyl ring or a 5- or 6-membered heterocyclic ring, each ring optionally substituted with one or more substituents independently selected from R$^6$; and
n is 0, 1 or 2;
wherein the asterisk represents that the carbon atom is a chiral quaternary carbon atom;

comprising reacting a compound of formula (II):

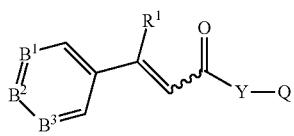
(II)

wherein $B^1$, $B^2$, $B^3$, $R^1$, Y and Q are as defined for formula (I), with hydroxylamine in the presence of water, a base and a chiral phase transfer catalyst of formula (IIIa) or (IIIb):

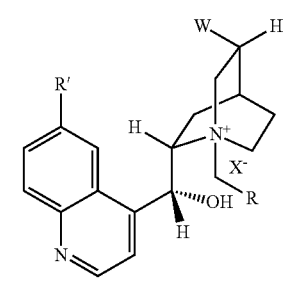
(IIIa)

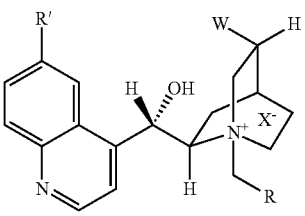
(IIIb)

wherein R is aryl or heteroaryl substituted with one or more aralkoxy groups, amino, alkylamino or dialkylamino; R' is hydrogen or $C_1$-$C_3$alkoxy, W is ethyl or vinyl and $X^-$ is an anion; and isolating the compound.

2. The process of paragraph 1, wherein the compound of formula (I) enriched in one enantiomer is isolated by crystallizing the compound from an aromatic solvent or a mixture of solvents comprising an aromatic solvent.

3. The process of paragraph 2, wherein the aromatic solvent is selected from the group consisting of toluene, ethylbenzene, xylenes, chlorobenzene, o-dichlorobenzene, fluorobenzene, anisole and mesitylene, or a mixture thereof.

4. The process of paragraph 3, wherein the aromatic solvent is toluene.

5. The process of any of paragraphs 1 to 4, wherein prior to isolating the compound of formula (I) enriched in an enantiomer, the process further comprises crystallizing racemic compound of formula (I) and removing the solid.

6. The process according to any one of paragraphs 1 to 5, wherein Y is

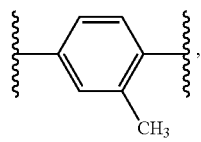
Y-1

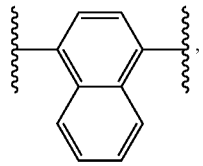
Y-2

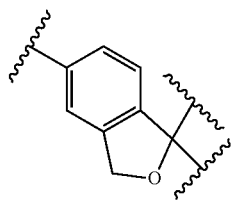
Y-3

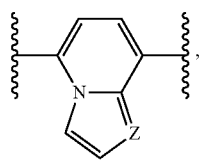
Y-4

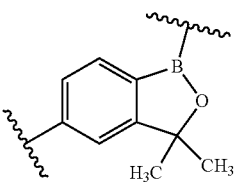
Y-5 or

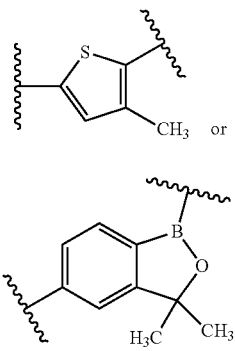
Y-6 wherein Z is N or CH.

7. The process according to paragraph 1 or 6, wherein Q is —C(O)NHCH$_2$C(O)NHCH$_2$CF$_3$, —C(O)CH$_2$S(O)$_2$CH$_3$, —C(O)NHCH$_2$CH$_2$SCH$_3$ or (—CH$_2$—)(—CH$_2$—)N(CO)CH$_2$S(O)$_2$CH$_3$.

8. The process according to any one of paragraphs 1 to 7, wherein $X^-$ in the chiral phase transfer catalyst of formula (IIIa) or (IIIb) is a halogen counter ion.

9. The process according to paragraph 8, wherein $X^-$ is a chloride counter ion.

10. The process according to any one of paragraphs 1 to 9, wherein R in the chiral phase transfer catalyst of formula (IIIa) or (IIIb) is a phenyl group that is substituted by 1, 2, 3, 4 or 5 aralkoxy groups.

11. The process according to paragraph 10, wherein the aralkoxy group is a benzyloxy group.

12. The process according to paragraph 10, wherein R is substituted with 3 aralkoxy groups.

13. The process according to paragraph 12, wherein R is 3,4,5-tris(benzyloxy)phenyl.

14. A process for the preparation of an isoxazoline compound of Formula IA, wherein $X^1$, $X^2$ and $X^3$ are each independently H, chloro, fluoro or CF$_3$, which is enriched in the (S)-enantiomer:

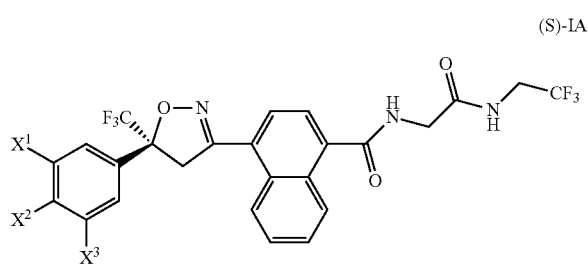

comprising reacting a compound of formula (IIA):

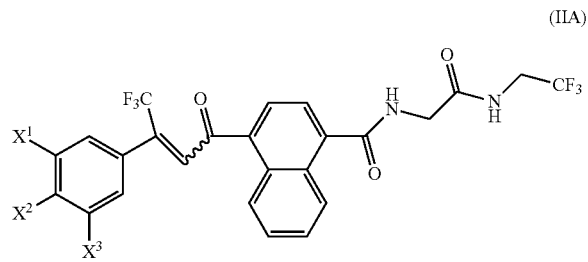

wherein $X^1$, $X^2$ and $X^3$ are H, chloro, fluoro or $CF_3$, with hydroxylamine in the presence of water, an organic solvent that is not miscible with water, a base and a chiral phase transfer catalyst of formula (IIIa):

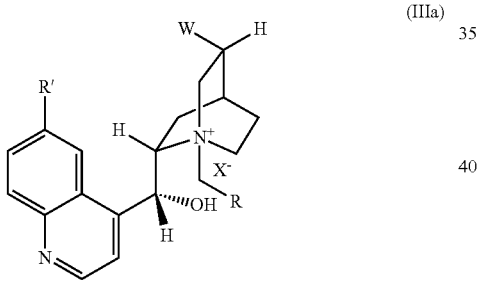

wherein R is aryl or heteroaryl optionally substituted with one or more $C_1$-$C_3$alkoxy, amino, $C_1$-$C_3$alkylamino, $C_1$-$C_3$dialkylamino or aralkoxy groups, R' is hydrogen or $C_1$-$C_3$alkoxy, W is ethyl or vinyl and $X^-$ is an anion; and isolating the compound of formula (S)-IA.

15. The process according to paragraph 14, wherein the compound of formula (S)-IA is isolated by crystallizing the compound from an aromatic solvent or a mixture of solvents comprising an aromatic solvent.
16. The process according to paragraph 15, wherein the aromatic solvent is selected from the group consisting of toluene, ethylbenzene, xylenes, chlorobenzene, o-dichlorobenzene, fluorobenzene, anisole and mesitylene, or a combination thereof.
17. The process according to paragraph 16, wherein the aromatic solvent is toluene.
18. The process of any one of paragraphs 14-17, wherein prior to isolating the compound of formula (S)-IA, the process further comprises crystallizing racemic compound of formula IA and removing the solid.
19. The process according to paragraph 14, wherein R in the chiral phase transfer catalyst of formula (IIIa) is phenyl substituted by 1, 2 or 3 methoxy or ethoxy groups, and R' is hydrogen or methoxy.
20. The process according to paragraph 14, wherein R in the chiral phase transfer catalyst of formula (IIIa) is phenyl substituted by 1, 2 or 3 benzyloxy groups, and R' is hydrogen or methoxy.
21. The process according to paragraph 14, wherein R in the chiral phase transfer catalyst of formula (IIIa) is 3,4,5-tris(benzyloxy)phenyl.
22. The process according to paragraph 14, wherein $X^1$ and $X^3$ are independently chloro or $CF_3$ and $X^2$ is H or fluoro.
23. The process according to paragraph 14, wherein $X^1$ chloro; $X^3$ is $CF_3$ and $X^2$ is H.
24. The process according to paragraph 14, wherein $X^1$ and $X^3$ are chloro; and $X^2$ is H.
25. The process according to paragraph 14, wherein $X^1$ and $X^3$ are chloro and $X^2$ is fluoro.
26. The process according to paragraph 14, wherein $X^1$ is chloro; $X^3$ is $CF_3$ and $X^2$ is fluoro.
27. A chiral phase transfer catalyst of formula (IIIa):

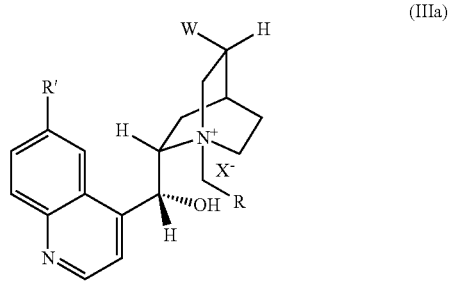

wherein R is aryl or heteroaryl substituted with one or more aralkoxy groups, R' is hydrogen or $C_1$-$C_3$alkoxy, W is ethyl or vinyl and $X^-$ is an anion.
28. The chiral phase transfer catalyst of paragraph 27, wherein R is phenyl.
29. The chiral phase transfer catalyst of paragraph 27 or 28, wherein $X^-$ is a halogen counter ion.
30. The chiral phase transfer catalyst of paragraph 27, wherein R is phenyl substituted by one or more benzyloxy groups.
31. The chiral phase transfer catalyst of paragraph 30, wherein R is 3,4,5-tris(benzyloxy)phenyl.
32. The chiral phase transfer catalyst of paragraph 27, wherein W is vinyl and $X^-$ is chloride.
33. The chiral phase transfer catalyst of paragraph 27, wherein:
R is phenyl substituted by one or more benzyloxy groups;
R' is hydrogen or methoxy;
W is vinyl; and
X is halogen.
34. The chiral phase transfer catalyst of paragraph 33, wherein R' is methoxy.
35. The chiral phase transfer catalyst of paragraph 27, wherein:
R is phenyl substituted by one or more benzyloxy groups;
R' is hydrogen or methoxy;
W is ethyl; and
X is halogen.
36. The chiral phase transfer catalyst of paragraph 35, wherein R' is methoxy.

37. The chiral phase transfer catalyst of paragraph 27, wherein the chiral phase transfer catalyst has the formula (IIIa-13-1), (IIIa-13-2), (IIIa-13-3) or (IIIa-13-4):

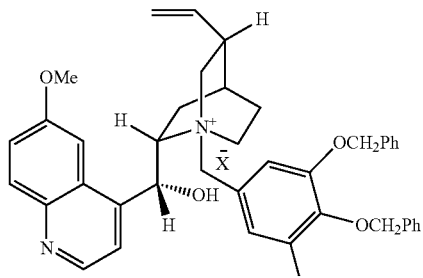
(IIIa-13-1)

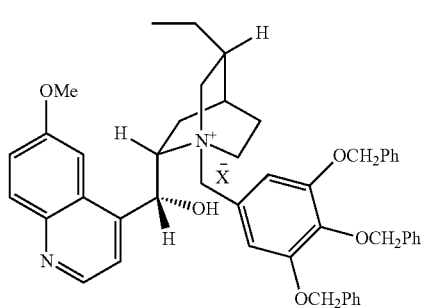
(IIIa-13-2)

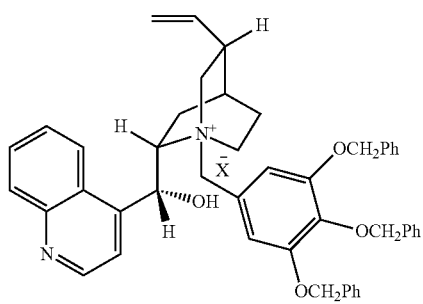
(IIIa-13-3)

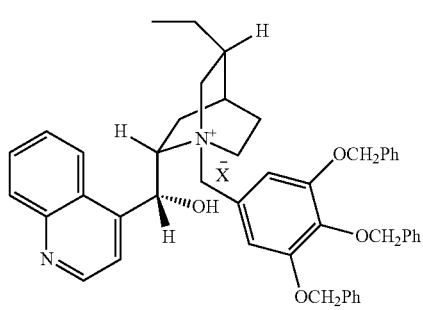
(IIIa-13-4)

wherein X⁻ is a halogen counter ion.

38. The chiral phase transfer catalyst of paragraph 37, wherein X⁻ is chloride.

39. A crystalline toluene solvate of (S)-afoxolaner having the formula:

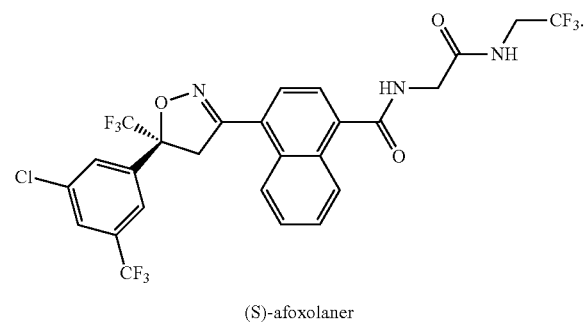 [SMILES: O=C(CNC(=O)c1ccc(C2=NO[C@@](c3cc(Cl)cc(C(F)(F)F)c3)(C(F)(F)F)C2)c2ccccc12)NCC(F)(F)F]
(S)-afoxolaner

40. The crystalline toluene solvate of paragraph 39, which is characterized by an X-ray powder diffraction pattern comprising two or more of the 2-theta peaks selected from the group consisting of:

| Angle 2-Theta ° |
| --- |
| 4.859, |
| 22.236, |
| 18.838, |
| 8.516, |
| 25.643, |
| 25.291, |
| 21.859, |
| 18.411, |
| 19.894 and |
| 12.746 |

±0.2 2-theta, as determined on a diffractometer using Cu-Kα radiation.

41. The crystalline toluene solvate of paragraph 39, which is characterized by an X-ray powder diffraction pattern comprising three or more peaks selected from the group consisting of:

| Angle 2-Theta ° |
| --- |
| 4.859, |
| 22.236, |
| 18.838, |
| 8.516, |
| 25.643, |
| 25.291, |
| 21.859, |
| 18.411, |
| 19.894 and |
| 12.746 |

±0.2 2-theta.

42. The crystalline toluene solvate of paragraph 39 characterized by an X-ray powder diffraction pattern substantially as shown in FIG. 8.

43. The crystalline toluene solvate of paragraph 39 which is characterized by a differential scanning calorimetry (DSC) thermogram having an endotherm at a temperature of about 83° C. to about 87° C., corresponding to the toluene solvate.

44. The crystalline toluene solvate of paragraph 39 which is characterized by a differential scanning calorimetry (DSC) thermogram having an endotherm at a temperature of about 84.7° C., corresponding to the toluene solvate.

45. The crystalline toluene solvate of paragraph 39, which is characterized by a differential scanning calorimetry thermogram substantially as shown in FIG. 7.

46. The crystalline toluene solvate of paragraph 39 characterized by a thermogravimetric analysis (TGA) thermogram characterized by weight loss of about 10.5% from about about 26° C. at about 160° C.

47. The crystalline toluene solvate of paragraph 39 characterized by thermogravimetric analysis thermogram substantially as shown in FIG. 7.

48. The crystalline toluene solvate of paragraph 39 characterized by unit cell parameters substantially equal to the following:

| | |
|---|---|
| Cell Volume | 1561.42 Å$^3$ |
| Symmetry Cell System | Triclinic |
| Symmetry Space Group Name | P1 |
| Cell Length a | 8.201 Å |
| Cell Length b | 10.7031 Å |
| Cell Length c | 18.6462 Å |
| Cell Angle α | 75.6862° |
| Cell Angle β | 84.2126° |
| Cell Angle γ | 80.592° |
| Density (g/cm$^3$) | 1.497 |

49. The crystalline toluene solvate of paragraph 39 characterized by unit cell parameters substantially equal to the following cell:

| | |
|---|---|
| Cell Volume | 1561.42 Å$^3$ |
| Symmetry Cell System | Triclinic |
| Symmetry Space Group Name | P1 |
| Cell Length a | 8.201 Å |
| Cell Length b | 10.7031 Å |
| Cell Length c | 18.6462 Å |
| Cell Angle α | 75.6862° |
| Cell Angle β | 84.2126° |
| Cell Angle γ | 80.592° |
| Density (g/cm3) | 1.497 |
| R indices | 5.5% |
| Absolute Structure Parameter | −0.03 |

50. The crystalline toluene solvate of paragraph 39 characterized by having two or more of the following characteristics:
  i) an X-ray powder diffraction pattern comprising at least three 2-theta values selected from the group consisting of

| Angle 2-Theta ° |
|---|
| 4.859, |
| 22.236, |
| 18.838, |
| 8.516, |
| 25.643, |
| 25.291, |
| 21.859, |
| 18.411, |
| 19.894 and |
| 12.746 |

±0.2 2-theta;
  ii) an X-ray powder diffraction pattern substantially in accordance with the X-ray powder diffraction spectrum shown in FIG. 8;
  iii) a differential scanning calorimetry (DSC) thermogram having an endotherm at a temperature of between about 83° C. to about 87° C.;
  iv) a differential scanning calorimetry thermogram substantially as shown in FIG. 7; and
  v) a thermogravimetric analysis (TGA) diagram substantially the same as that shown in shown in FIG. 7.

51. The crystalline toluene solvate of paragraph 39, wherein the molar ratio of (S)-afoxolaner to toluene is about 1:1.

52. The crystalline toluene solvate of paragraph 39, wherein the crystalline (S)-afoxolaner toluene solvate is isolated.

53. The crystalline toluene solvate of paragraph 39, wherein at least 90% of (S)-afoxolaner by weight is a crystalline toluene solvate form.

54. The crystalline toluene solvate of paragraph 39, wherein at least 80% of (S)-afoxolaner by weight is a crystalline toluene solvate form.

55. The crystalline toluene solvate of paragraph 39, wherein at least 70% of (S)-afoxolaner by weight is a crystalline toluene solvate form.

56. The crystalline toluene solvate of paragraph 39, wherein at least 60% of (S)-afoxolaner by weight is a crystalline toluene solvate form.

57. A pesticidal or parasiticidal composition comprising the crystalline toluene solvate according to paragraph 39, and at least one agriculturally or pharmaceutically acceptable carrier or excipient.

58. The pesticidal or parasiticidal composition of paragraph 57 comprising the crystalline toluene solvate according to paragraph 39, wherein said crystalline toluene solvate is in admixture with one or more distinct polymorphic forms and/or an amorphous compound of (S)-afoxolaner.

59. The pesticidal or parasiticidal of paragraph 57, wherein wherein at least 80% of (S)-afoxolaner is a crystalline toluene solvate form.

60. The pesticidal or parasiticidal composition of paragraph 57, wherein the composition comprises at least 95% by weight of the crystalline toluene solvate of claim 36 based on the total weight of compound of (S)-afoxolaner in the composition.

61. The pesticidal or parasiticidal composition of paragraph 60, wherein the composition comprises at least 98% by weight of the crystalline toluene solvate of claim 39 based on the total weight of compound of (S)-afoxolaner in the composition.

62. A process for preparing the crystalline toluene solvate of paragraph 39 said process comprising crystallizing (S)-afoxolaner from toluene, optionally in the presence of a second solvent.

63. The process of paragraph 62 comprising crystallizing (S)-afoxolaner from a mixture of toluene and cyclohexane.

64. The process of paragraph 63 wherein the mixture of toluene and cyclohexane comprises from a ratio of from about 50:50 to about 99:1 (v/v) toluene to cyclohexane.

65. The process of paragraph 62 comprising:
  a) providing a solution of (S)-afoxolaner in toluene, optionally in the presence of a second solvent;
  b) obtaining the crystalline solvate of (S)-afoxolaner from the solution of step a); and
  c) isolating the crystalline toluene solvate of (S)-afoxolaner.

66. The process of paragraph 65, wherein the solution of (S)-afoxolaner in toluene, optionally in the presence of a second solvent, is obtained by combining solid (S)-afoxolaner and toluene, optionally in the presence of a second solvent, and heating the combination.

67. The process of paragraph 66, wherein the combination is heated to a temperature of between about 50° C. to about 80° C.

68. The process of paragraph 65, wherein the crystalline toluene solvate of (S)-afoxolaner is obtained by cooling the solution of step a).
69. The process of paragraph 68, wherein the solution of step a) is cooled to a temperature of less than about 20° C.
70. The process of claim 68, wherein the solution of step a) is cooled to a temperature of less than about 15° C.
71. The process of paragraph 68, wherein the solution of step a) is cooled to a temperature of about 10° C.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:
1. A crystalline solvated solid form of an isoxazoline compound of formula (I) with an aromatic solvent:

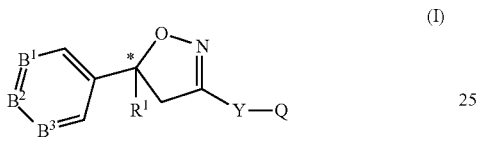

(I)

wherein:
$B^1$, $B^2$, $B^3$, are each independently C—R or N;
each R is independently H, halogen, cyano, —$NO_2$, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino or alkoxycarbonyl;
$R^1$ is $C_1$-$C_3$alkyl or $C_1$-$C_3$haloalkyl;
Y is Y-1 or Y-2:

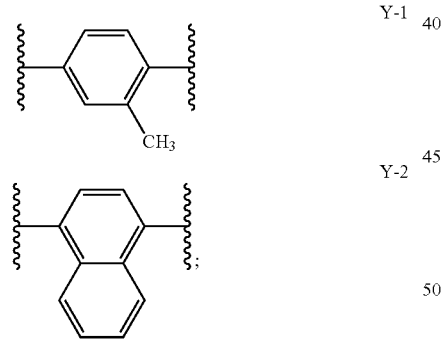

Q is T-$NR^2R^3$, OH, $NH_2$, alkoxy, haloalkoxy, alkylamino, haloalkylamino, dialkylamino, halodialkylamino, thiol, alkylthio, haloalkylthio, alkylsulfinyl, haloalkylsulfinyl, alkylsulfonyl, haloalkylsulfonyl, or an optionally substituted 5- or 6-membered carbocyclyl, heterocyclyl or heteroaryl ring;
T is $(CH_2)_n$, $CH(CH_3)$, CH(CN), C(=O) or C(=S);
$R^2$ is H, alkyl, alkenyl, alkynyl, cycloalkyl, alkylcycloalkyl, cycloalkylalkyl, alkylcarbonyl or alkoxycarbonyl;
$R^3$ is H, $OR^7$, $NR^8R^9$ or $Q^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from $R^4$; or
$R^2$ and $R^3$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;
each $R^4$ is independently halogen; alkyl, cycloalkyl, alkoxy, alkylthio, haloalkylthio, alkylsulfinyl, haloalkylsulfinyl, alkyl sulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —$NH_2$, —CN or —$NO_2$; or $Q^2$;
each $R^5$ is independently halogen, alkoxy, haloalkoxy, alkylthio, haloalkylthio, alkylsulfinyl, haloalkylsulfinyl, alkyl sulfonyl, haloalkylsulfonyl, alkylamino, dialkylamino, alkoxycarbonyl, —CN or —$NO_2$;
each $R^6$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN, —$NO_2$, phenyl or pyridinyl;
$R^7$ is H; or alkyl, alkenyl, alkynyl, cycloalkyl, alkylcycloalkyl or cycloalkylalkyl, each optionally substituted with one of more halogen;
$R^8$ is H, alkyl, alkenyl, alkynyl, cycloalkyl, alkylcycloalkyl, cycloalkylalkyl, alkylcarbonyl or alkoxycarbonyl;
$R^9$ is H; $Q^3$; or alkyl, alkenyl, alkynyl, cycloalkyl, alkylcycloalkyl or cycloalkylalkyl, each optionally substituted with one or more substituents independently selected from $R^4$; or
$R^8$ and $R^9$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;
$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^5$;
$Q^2$ is independently a phenyl ring or a 5- or 6-membered heterocyclic ring, each ring optionally substituted with one or more substituents independently selected from $R^6$;
$Q^3$ is a phenyl ring or a 5- or 6-membered heterocyclic ring, each ring optionally substituted with one or more substituents independently selected from $R^6$; and
n is 0, 1 or 2;
wherein the asterisk represents that the carbon atom is a chiral quaternary carbon atom.
2. The crystalline solvated solid form of claim 1, wherein: Y is Y-2.

3. The crystalline solvated solid form of claim 1, wherein Q is —C(O)NHCH$_2$C(O)NHCH$_2$CF$_3$, —C(O)CH$_2$S(O)$_2$CH$_3$, or —C(O)NHCH$_2$CH$_2$SCH$_3$.

4. The crystalline solvated solid form of claim 1, wherein B$^1$, B$^2$, B$^3$, are each independently C—R; and each R is independently H, halogen or haloalkyl.

5. The crystalline solvated solid form of claim 1, wherein R$^1$ is CF$_3$.

6. The crystalline solvated solid form of claim 1, wherein:
Y is Y-2;
R$^1$ is CF$_3$;
B$^1$, B$^2$, B$^3$, are each independently C—R; each R is H, halogen or CF$_3$; and
Q is —C(O)NHCH$_2$C(O)NHCH$_2$CF$_3$.

7. The crystalline solvated solid form of claim 6, wherein B$^1$ is C—Cl; B$^2$ is C—H or C—F and B$^3$ is C-CF$_3$.

8. The crystalline solvated solid form of claim 1, wherein the aromatic solvent is toluene.

9. The crystalline solvated solid form of claim 6, wherein the crystalline solvated solid form is a crystalline toluene solvate of (S)-afoxolaner having the formula:

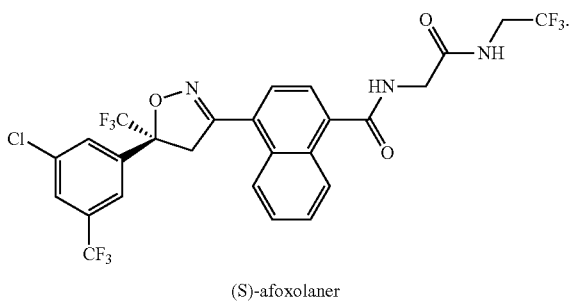 [SMILES: O=C(CNC(=O)c1ccc(C2=NO[C@@](c3cc(Cl)cc(C(F)(F)F)c3)(C(F)(F)F)C2)c2ccccc12)NCC(F)(F)F]

(S)-afoxolaner

10. The crystalline toluene solvate of claim 9, which is characterized by an X-ray powder diffraction pattern comprising two or more of the 2-theta peaks selected from the group consisting of:

| Angle 2-Theta ° |
|---|
| 4.859, |
| 22.236, |
| 18.838, |
| 8.516, |
| 25.643, |
| 25.291, |
| 21.859, |
| 18.411, |
| 19.894 and |
| 12.746 |

±0.2 2-theta, as determined on a diffractometer using Cu-Kα radiation.

11. The crystalline toluene solvate of claim 9, which is characterized by an X-ray powder diffraction pattern comprising three or more peaks selected from the group consisting of:

| Angle 2-Theta ° |
|---|
| 4.859, |
| 22.236, |

| Angle 2-Theta ° |
|---|
| 18.838, |
| 8.516, |
| 25.643, |
| 25.291, |
| 21.859, |
| 18.411, |
| 19.894 and |
| 12.746 |

±0.2 2-theta.

12. The crystalline toluene solvate of claim 9 characterized by an X-ray powder diffraction pattern substantially as shown in FIG. 8.

13. The crystalline toluene solvate of claim 9 which is characterized by a differential scanning calorimetry (DSC) thermogram having an endotherm at a temperature of about 83° C. to about 87° C., corresponding to the toluene solvate.

14. The crystalline toluene solvate of claim 9 which is characterized by a differential scanning calorimetry (DSC) thermogram having an endotherm at a temperature of about 84.7° C., corresponding to the toluene solvate.

15. The crystalline toluene solvate of claim 9, which is characterized by a differential scanning calorimetry thermogram substantially as shown in FIG. 7.

16. The crystalline toluene solvate of claim 9 characterized by a thermogravimetric analysis (TGA) thermogram characterized by weight loss of about 10.5% from about about 26° C. at about 160° C.

17. The crystalline toluene solvate of claim 9 characterized by thermogravimetric analysis thermogram substantially as shown in FIG. 7.

18. The crystalline toluene solvate of claim 9 characterized by unit cell parameters substantially equal to the following:

| | |
|---|---|
| Cell Volume | 1561.42 Å$^3$ |
| Symmetry Cell System | Triclinic |
| Symmetry Space Group Name | P1 |
| Cell Length a | 8.201 Å |
| Cell Length b | 10.7031 Å |
| Cell Length c | 18.6462 Å |
| Cell Angle α | 75.6862° |
| Cell Angle β | 84.2126° |
| Cell Angle γ | 80.592° |
| Density (g/cm$^3$) | 1.497. |

19. The crystalline toluene solvate of claim 9 characterized by unit cell parameters substantially equal to the following cell:

| | |
|---|---|
| Cell Volume | 1561.42 Å$^3$ |
| Symmetry Cell System | Triclinic |
| Symmetry Space Group Name | P1 |
| Cell Length a | 8.201 Å |
| Cell Length b | 10.7031 Å |
| Cell Length c | 18.6462 Å |
| Cell Angle α | 75.6862° |
| Cell Angle β | 84.2126° |
| Cell Angle γ | 80.592° |
| Density (g/cm3) | 1.497 |
| R indices | 5.5% |
| Absolute Structure Parameter | −0.03. |

20. The crystalline toluene solvate of claim 9 characterized by having two or more of the following characteristics:
   i) an X-ray powder diffraction pattern comprising at least three 2-theta values selected from the group consisting of

| Angle 2-Theta ° |
|---|
| 4.859, |
| 22.236, |
| 18.838, |
| 8.516, |
| 25.643, |
| 25.291, |
| 21.859, |
| 18.411, |
| 19.894 and |
| 12.746 |

±0.2 2-theta;
   ii) an X-ray powder diffraction pattern substantially in accordance with the X-ray powder diffraction spectrum shown in FIG. 8;
   iii) a differential scanning calorimetry (DSC) thermogram having an endotherm at a temperature of between about 83° C. to about 87° C.;
   iv) a differential scanning calorimetry thermogram substantially as shown in FIG. 7; and
   v) a thermogravimetric analysis (TGA) diagram substantially the same as that shown in shown in FIG. 7.

21. The crystalline toluene solvate of claim 9, wherein the molar ratio of (S)-afoxolaner to toluene is about 1:1.

22. The crystalline toluene solvate of claim 9, wherein the crystalline (S)-afoxolaner toluene solvate is isolated.

23. The crystalline toluene solvate of claim 9, wherein at least 90% of (S)-afoxolaner by weight is a crystalline toluene solvate form.

24. The crystalline toluene solvate of claim 9, wherein at least 80% of (S)-afoxolaner by weight is a crystalline toluene solvate form.

25. The crystalline toluene solvate of claim 9, wherein at least 70% of (S)-afoxolaner by weight is a crystalline toluene solvate form.

26. The crystalline toluene solvate of claim 9, wherein at least 60% of (S)-afoxolaner by weight is a crystalline toluene solvate form.

27. A pesticidal or parasiticidal composition comprising the crystalline solvated solid form according to claim 1, and at least one agriculturally or pharmaceutically acceptable carrier or excipient.

28. The pesticidal or parasiticidal composition of claim 27, wherein the crystalline solvated solid form is a crystalline toluene solvate of (S)-afoxolaner, and wherein said crystalline toluene solvate of (S)-afoxolaner is in admixture with one or more distinct polymorphic forms of (S)-afoxolaner and/or an amorphous form of (S)-afoxolaner.

29. The pesticidal or parasiticidal composition of claim 28, wherein at least 80% of (S)-afoxolaner is a crystalline toluene solvate form.

30. The pesticidal or parasiticidal composition of claim 28, wherein the composition comprises at least 95% by weight of the crystalline toluene solvate of (S)-afoxolaner based on the total weight of (S)-afoxolaner in the composition.

31. The pesticidal or parasiticidal composition of claim 30, wherein the composition comprises at least 98% by weight of the crystalline toluene solvate of (S)-afoxolaner based on the total weight of (S)-afoxolaner in the composition.

* * * * *